(12) United States Patent
Takemoto et al.

(10) Patent No.: US 7,169,931 B2
(45) Date of Patent: Jan. 30, 2007

(54) CYCLIC COMPOUNDS EXHIBITING THROMBOPOIETIN RECEPTOR AGONISM

(75) Inventors: Hiroshi Takemoto, Osaka (JP); Masami Takayama, Osaka (JP); Yutaka Yoshida, Osaka (JP)

(73) Assignee: Shionogi & Co., Ltd., Osaka (JP)

( * ) Notice: Subject to any disclaimer, the term of this patent is extended or adjusted under 35 U.S.C. 154(b) by 438 days.

(21) Appl. No.: 10/470,002

(22) PCT Filed: Jan. 25, 2002

(86) PCT No.: PCT/JP02/00546

§ 371 (c)(1), (2), (4) Date: Jul. 25, 2003

(87) PCT Pub. No.: WO02/059099

PCT Pub. Date: Aug. 1, 2002

(65) Prior Publication Data

US 2004/0082626 A1    Apr. 29, 2004

(30) Foreign Application Priority Data

Jan. 26, 2001 (JP) ............... 2001-017779
Jul. 24, 2001 (JP) ............... 2001-223414

(51) Int. Cl.
 C07D 277/46    (2006.01)
 A61K 31/426    (2006.01)

(52) U.S. Cl. .................... 548/195; 514/371

(58) Field of Classification Search ........... 548/195
See application file for complete search history.

(56) References Cited

U.S. PATENT DOCUMENTS

| 5,189,049 | A |   | 2/1993  | Frehel et al.         |         |
|-----------|---|---|---------|-----------------------|---------|
| 5,314,889 | A |   | 5/1994  | Boigegrain et al.     |         |
| 5,973,126 | A | * | 10/1999 | Ueno et al.           | 534/656 |
| 6,084,101 | A | * | 7/2000  | Ueno et al.           | 546/309 |
| 6,365,748 | B1|   | 4/2002  | Radisson              |         |

FOREIGN PATENT DOCUMENTS

| EP | 1 207 155 A1 | 5/2002 |
| EP | 1 253 142 A1 | 10/2002 |
| JP | 10-72492     | 3/1998 |
| JP | 10-287634    | 10/1998 |
| JP | 11-1477      | 1/1999 |
| JP | 11-152276    | 6/1999 |
| WO | WO 96/40750  | 12/1996 |
| WO | WO 97/25915  | 7/1997 |
| WO | WO 97/32863  | 9/1997 |
| WO | WO 00/35446  | 6/2000 |

OTHER PUBLICATIONS

CA Registry No. 353515-94-3, entered into Registry file on STN on Aug. 29, 2001.*
CA Registry No. 326886-83-3, entered into Registry file on STN on Mar. 13, 2001.*
CA Registry No. 326886-82-2, entered into Registry file on STN on Mar. 13, 2001.*
CA Registry No. 326886-81-1, entered into Registry file on STN on Mar. 13, 2001.*
CA Registry No. 326886-80-0, entered into Registry file on STN on Mar. 13, 2001.*
CA Registry No. 326886-79-7, entered into Registry file on STN on Mar. 13, 2001.*
CA Registry No. 326886-78-6, entered into Registry file on STN on Mar. 13, 2001.*
Vigon et al.; "Molecular Cloning and Characterization of MPL, the Human Homolog of the V-MPL Oncogene: Identification of a Member of the Hematopoietic Growth Factor Receptor Superfamily"; Proc. Natl. Acad. Sci. vol. 89, pp. 5640-5644, (1992).

* cited by examiner

Primary Examiner—Laura L. Stockton
(74) Attorney, Agent, or Firm—Finnegan, Henderson, Farabow, Garrett & Dunner, L.L.P.

(57) ABSTRACT

Pharmaceutical compositions containing as an active ingredient compounds of the general formula (I), prodrugs of the same, pharmaceutically acceptable salts of both, or solvates of them and exhibiting thrombopoietin receptor agonism:

$$X^1\text{—}Y^1\text{-}Z^1 \qquad (I)$$

wherein $X^1$ is optionally substituted aryl, optionally substituted heteroaryl or the like; $Y^1$ is —$NR^4CO$—$(CH_2)_{0-2}$— or the like (wherein $R^4$ is hydrogen atom or the like); and $Z^1$ is a cyclic group fused the same or different two ring selected from optionally substituted carbocyclic group and optionally substituted heterocyclic group.

13 Claims, No Drawings

CYCLIC COMPOUNDS EXHIBITING THROMBOPOIETIN RECEPTOR AGONISM

TECHNICAL FIELD

The present invention relates to a pharmaceutical composition exhibiting thrombopoietin receptor agonism.

BACKGROUND ART

Thrombopoietin, polypeptide cytokine composed of 332 amino acids, activates the production of platelets by stimulating the differentiation and proliferation of megakaryocytes through the receptor and is expected as a medicine for hemopathy accompanied with the unusual number of platelets, for example, thrombocytopenia. DNA sequences encoding the thrombopoietin receptor have been described in Proc. Natl. Acad. Sci., 89, 5640–5644 (1992). Low molecular peptides having an affinity for the thrombopoietin receptor is also known (JP98/72492A and WO96/40750), but these peptide derivatives are not generally practical for oral administration.

1,4-Benzodiazepine derivatives as a low molecule compound having an affinity to the thrombopoietin receptor is described in JP99/1477A and JP99/152276A.

As the compound having a similar structure of the present invention compound, indoline derivatives having an anticholecystokinin actvity and an antigastrin activity are described in JP91/279374A, and benzothiazole derivatives are described without referring to its activity in Pharma Library Collection, Otava Chemical Collection and the like, but the affinity for thrombopoietin receptor is not described therein.

DISCLOSURE OF INVENTION

The object of the present invention is to prepare pharmaceutical compositions exhibiting thrombopoietin receptor agonism and provide orally administrable platelet production modifiers.

In the above situation, the inventors of the present invention have found that the following compounds exhibit strong thrombopoietin receptor agonism to achieve the present invention.

The present invention relates to:
1) A pharmaceutical composition exhibiting thrombopoietin receptor agonism which contains as an active ingredient a compound of the general formula (I):

$$X^1\text{—}Y^1\text{-}Z^1 \qquad (I)$$

wherein $X^1$ is optionally substituted aryl, optionally substituted aralkyl, optionally substituted heteroaryl, or optionally substituted heteroarylalkyl;
$Y^1$ is $-NR^A CO-(CR^C R^D)_{0-2}-$, $-NR^A CO-(CH_2)_{0-2}-V-$, $-NR^A CO-CR^C=CR^D-$, $-V-(CH_2)_{1-5}-NR^A CO-(CH_2)_{0-2}-$, $-V-(CH_2)_{1-5}-CONR^A-(CH_2)_{0-2}-$, $-CONR^A-(CH_2)_{0-2}-$, $-(CH_2)_{0-2}-NR^A-SO_2-(CH_2)_{0-2}-$, $-(CH_2)_{0-2}-SO_2-NR^A-(CH_2)_{0-2}-$, $-NR^A-(CH_2)_{0-2}-$, $-NR^A-CO-NR^A-$, $-NR^A-CS-NR^A-$, $-N=C(-SR^A)-NR^A-$, $-NR^A CSNR^A CO-$, $-N=C(-SR^A)-NR^A CO-$, $-NR^A-(CH_2)_{1-2}-NR^A-CO-$, $-NR^A CONR^A NR^B CO-$, or $-N=C(-NR^A R^A)-NR^A-CO-$ wherein $R^A$ is each independently hydrogen atom or lower alkyl; $R^B$ is hydrogen atom or phenyl; $R^C$ and $R^D$ are each independently hydrogen atom, halogen atom, optionally substituted lower alkyl, optionally substituted lower alkyloxy, optionally substituted lower alkylthio, optionally substituted lower alkenyl, optionally substituted lower alkynyl, optionally substituted aryl, optionally substituted heteroaryl, optionally substituted cycloalkyl, optionally substituted aralkyl, optionally substituted heteroarylalkyl, optionally substituted non-aromatic heterocyclic group, or optionally substituted amino; V is oxygen atom or sulfur atom;

$Z^1$ is fused cyclic group formed by fusing the same or different two rings selected from optionally substituted carbocyclic group and optionally substituted heterocyclic group;

its prodrug, or their pharmaceutically acceptable salt, or solvate thereof.

In more details, it relates to the following 2) to 26).

2) A pharmaceutical composition exhibiting thrombopoietin receptor agonism of 1), wherein $X^1$ is optionally substituted heteroaryl.

3) A pharmaceutical composition exhibiting thrombopoietin receptor agonism of 1), wherein $X^1$ is a group represented by the formula:

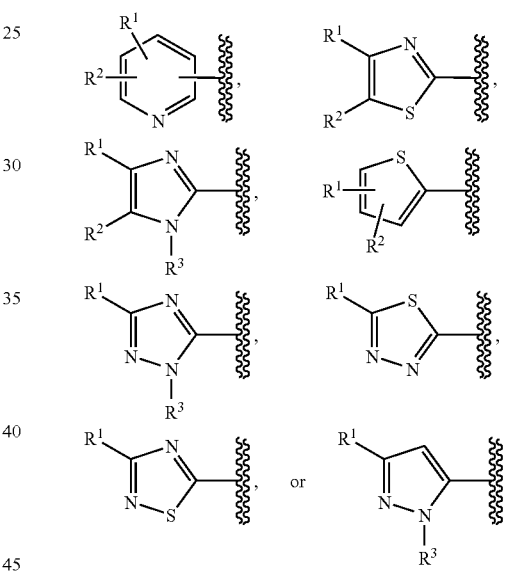

wherein $R^1$ and $R^2$ are each independently hydrogen atom, optionally substituted lower alkyl, carboxy, lower alkyloxycarbonyl, halogen atom, optionally substituted aminocarbonyl, optionally substituted heteroaryl, or optionally substituted aryl;
$R^3$ is hydrogen atom or optionally substituted lower alkyl.

4) A pharmaceutical composition exhibiting thrombopoietin receptor agonism of 1), wherein $X^1$ is a group represented by the formula:

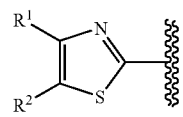

wherein $R^1$ and $R^2$ are as defined in 3).

5) A pharmaceutical composition exhibiting thrombopoietin receptor agonism of any one of 1) to 4), wherein $Y^1$ is —NHCO—, —CONH—, —NHCH₂—, —NHCO—CH=CH—, or —NHSO₂—.

6) A pharmaceutical composition exhibiting thrombopoietin receptor agonism of any one of 1) to 4), wherein $Y^1$ is —NHCO—.

7) A pharmaceutical composition exhibiting thrombopoietin receptor agonism of any one of 1) to 6), wherein $Z^1$ is a group represented by the formula:

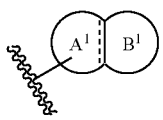

wherein $A^1$ ring and $B^1$ ring are each independently optionally substituted C5–C7 cycloalkane, optionally substituted C5–C7 cycloalkene, optionally substituted benzene ring, or optionally substituted 5- to 7-membered heterocyclic group containing any one or more selected from oxygen atom, sulfur atom and nitrogen atom in said ring;

a broken line (---) represents the presence or absence of a bond.

8) A pharmaceutical composition exhibiting thrombopoietin receptor agonism of any one of 1) to 7), wherein $Z^1$ is a group represented by the formula:

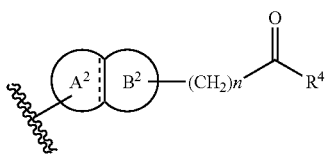

wherein A2 ring and B2 ring are each independently the following cyclic group optionally substituted with one or more substituent(s) selected from substituent A group, cyclic group consists of C5–C7 cycloalkane, C5–C7 cycloalkene, benzene ring, and 5- to 7-membered heterocyclic group containing any one or more selected from oxygen atom, sulfur atom and nitrogen atom in said ring, substituent A group consists of lower alkyl, halogen atom, halo(lower)alkyl, hydroxy, lower alkyloxy, halo(lower)alkyloxy, methylene and oxo;

$R_4$ is hydroxy, lower alkyloxy, or optionally substituted amino;

n is an integer of 0 to 4;

a broken line (---) represents the presence or absence of a bond.

9) A pharmaceutical composition exhibiting thrombopoietin receptor agonism of any one of 1) to 8), wherein $Z^1$ is the following fused cyclic group substituted with a group represented by the formula: —(CH₂)ₙCOR⁴ wherein n and $R^4$ are as defined in 8) and optionally with lower alkyl, halogen atom, halo(lower)alkyl, hydroxy, lower alkyloxy, halo(lower)alkyloxy, methylene and/or oxo, fused cyclic group consists of naphthyl, dihydronaphthyl, tetrahydronaphthyl, indanyl, and benzothienyl.

10) A pharmaceutical composition exhibiting thrombopoietin receptor agonism of any one of 1) to 9), which is a platelet production modifier.

11) Use of a compound of any one of 1) to 9), for preparation of a medicine for modifying platelet production.

12) A method for modifying platelet production of a mammal, including a human, which comprises administration to said mammal of a compound of any one of 1) to 9) in a therapeutically effective amount.

13) A compound represented by the general formula (II):

$$X^2—Y^2\text{-}Z^2 \qquad (II)$$

wherein $X^2$ is optionally substituted 5-member heteroaryl or optionally substituted pyridyl;

$Y^2$ is —NR$^A$CO—(CR$^C$R$^D$)₀₋₂—, —NR$^A$CO—(CH₂)₀₋₂—V—, —NR$^A$CO—CR$^C$=CR$^D$—, —V—(CH₂)₁₋₅— —NR$^A$CO—(CH₂)₀₋₂—, —V—(CH₂)₁₋₅—CONR$^A$—(CH₂)₀₋₂—, —CONR$^A$—(CH₂)₀₋₂—, —(CH₂)₀₋₂—NR$^A$—SO₂—(CH₂)₀₋₂—, —(CH₂)₀₋₂—SO₂—NR$^A$—(CH₂)₀₋₂—, —NR$^A$—(CH₂)₀₋₂—, —NR$^A$—CO—NR$^A$—, —NR$^A$—CS—NR$^A$—, —N=C(—SR$^A$)—NR$^A$—, —NR$^A$CSNR$^A$CO—, —N=C(—SR$^A$)—NR$^A$CO—, —NR$^A$—(CH₂)₁₋₂—NR$^A$—CO—, —NR$^A$CONR$^A$NR$^B$CO—, or —N=C(—NR$^A$R$^A$)—NR$^A$—CO— wherein $R^A$ is each independently hydrogen atom or lower alkyl; $R^B$ is hydrogen atom or phenyl; $R^C$ and $R^D$ are each independently hydrogen atom, halogen atom, optionally substituted lower alkyl, optionally substituted lower alkyloxy, optionally substituted lower alkylthio, optionally substituted lower alkenyl, optionally substituted lower alkynyl, optionally substituted aryl, optionally substituted heteroaryl, optionally substituted cycloalkyl, optionally substituted aralkyl, optionally substituted heteroarylalkyl, optionally substituted non-aromatic heterocyclic group, or optionally substituted amino; V is oxygen atom or sulfur atom;

$Z^2$ is a group represented by the formula:

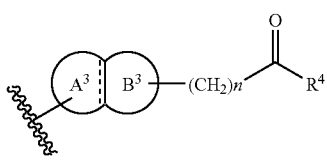

wherein $A^3$ ring and $B^3$ ring are each independently the following optionally substituted cyclic group, cyclic group consists of C5–C7 cycloalkane, C5–C7 cycloalkene, benzene ring, and 5- to 7-membered heterocyclic group containing any one or more selected from oxygen atom, sulfur atom and nitrogen atom in said ring;

$R^4$ is hydroxy, lower alkyloxy, or optionally substituted amino;

n is an integer of 0 to 4;

a broken line (---) represents the presence or absence of a bond;

provided that when B3 ring contains nitrogen atom in said ring, the nitrogen atom is not substituted with a group represented by the formule: (CH₂)ₙC(=O)R⁴;

its prodrug, or their pharmaceutically acceptable salt, or solvate thereof.

14) A compound described in 13), wherein $X^2$ is a group represented by the formula:

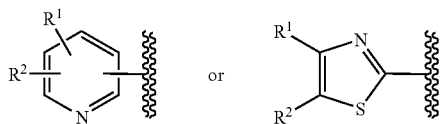

wherein $R^1$ and $R^2$ are each independently hydrogen atom, optionally substituted lower alkyl, carboxy, lower alkyloxycarbonyl, halogen atom, optionally substituted aminocarbonyl, optionally substituted heteroaryl, or optionally substituted aryl, its prodrug, or their pharmaceutically acceptable salt, or solvate thereof.

15) A compound described in 13), wherein $X^2$ is a group represented by the formula:

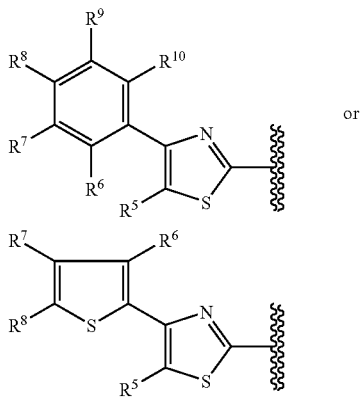

wherein $R^5$ is hydrogen atom, optionally substituted lower alkyl, carboxy, lower alkyloxycarbonyl, halogen atom, or optionally substituted aminocarbonyl;

$R^6$, $R^7$, $R^8$, $R^9$, and $R^{10}$ are each independently hydrogen atom, alkyl optionally substituted with one or more substituent(s) selected from substituent group B, cycloalkyl, alkyloxy optionally substituted with one or more substituent(s) selected from substituent group B, alkylthio, halogen atom, phenyl optionally substituted with one or more substituent(s) selected from substituent group C, heteroaryl optionally substituted with one or more substituent(s) selected from substituent group C, or nonaromatic heterocyclic group optionally substituted with one or more substituent(s) selected from substituent group C, substituent group B consists of cycloalkyl, hydroxy, alkyloxy, halogen atom, carboxy, lower alkyloxycarbonyl, aryloxycarbonyl, optionally substituted amino, phenyl optionally substituted with one or more substituent(s) selected from substituent group C, non-aromatic heterocyclic group, and heteroaryl, substituent group C consists of hydroxy, alkyl, halogen atom, halo(lower)alkyl, carboxy, lower alkyloxycarbonyl, alkyloxy, optionally substituted amino, non-aromatic heterocyclic group, and heteroaryl;

$R^5$ and $R^6$ taken together may form —$CH_2$—, —$CH_2CH_2$—, —$CH_2CH_2CH_2$—, —$OCH_2$—, or —$SCH_2$—;

$R^7$ and $R^8$ taken together may form —$(CH_2)_3$— or —$(CH_2)_4$—;

its prodrug, or their pharmaceutically acceptable salt, or solvate thereof.

16) A compound of any one of 13) to 15), wherein $Y^2$ is —NHCO—, —CONH—, or —NHSO$_2$—;

its prodrug, or their pharmaceutically acceptable salt, or solvate thereof.

17) A compound of any one of 13) to 16), wherein $A^3$ ring and $B^3$ ring of $Z^2$ are each independently selected from benzene, cyclopentane, cyclohexane, cyclopentene, cyclohexene, pyrole, pyrrolidine, furan, tetrahydrofuran, thiophen, oxazole, thiazole, pyridine, dihydropyran, tetrahydropyran, oxepine, and oxepane;

its prodrug, or their pharmaceutically acceptable salt, or solvate thereof.

18) A compound of any one of 13) to 17), wherein $Z^2$ is the following fused cyclic group substituted with a group represented by the formula: $(CH_2)_nCOR^4$ wherein n and $R^4$ are as defined in 13), and optionally with lower alkyl, halogen atom, halo(lower)alkyl, hydroxy, loweralkyloxy, halo(lower)alkyloxy, methylene and/or oxo, fused cyclic group consists of naphthyl, dihydronaphthyl, tetrahydronaphthyl, indanyl, and benzothienyl.

its prodrug, or their pharmaceutically acceptable salt, or solvate thereof.

19) A compound of the general formula (III):

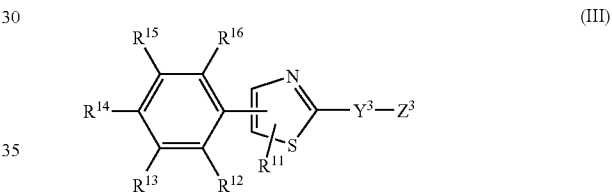

wherein $R^{11}$ is hydrogen atom, optionally substituted lower alkyl, carboxy, lower alkyloxycarbonyl, halogen atom, or optionally substituted aminocarbonyl;

$R^{12}$, $R^{13}$, $R^{14}$, $R^{15}$, and $R^{16}$ are each independently hydrogen atom, alkyl optionally substituted with one or more substituent(s) selected from substituent group B, cycloalkyl, alkyloxy optionally substituted with one or more substituent(s) selected from substituent group B, alkylthio, halogen atom, phenyl optionally substituted with one or more substituent(s) selected from substituent group C, heteroaryl optionally substituted with one or more substituent(s) selected from substituent group C, or nonaromatic heterocyclic group optionally substituted with one or more substituent(s) selected from substituent group C;

substituent group B consists of cycloalkyl, hydroxy, alkyloxy, halogen atom, carboxy, lower alkyloxycarbonyl, aryloxycarbonyl, optionally substituted amino, phenyl optionally substituted with one or more substituent(s) selected from substituent group C, non-aromatic heterocyclic group, and heteroaryl, substituent group C consists of hydroxy, alkyl, halogen atom, halo(lower)alkyl, carboxy, lower alkyloxycarbonyl, alkyloxy, optionally substituted amino, non-aromatic heterocyclic group, and heteroaryl;

$R^{11}$ and $R^{12}$ taken together may form —$CH_2$—, —$CH_2CH_2$—, —$CH_2CH_2CH_2$—, —$OCH_2$—, or —$SCH_2$—;

$R^{13}$ and $R^{14}$ taken together may form —$(CH_2)_3$— or —$(CH_2)_4$—;

$Y^3$ is —NHCO— or —CONH—;
$Z^3$ is a group represented by the following formula optionally substituted with lower alkyl, halogen atom, hydroxy, methylene, or oxo:
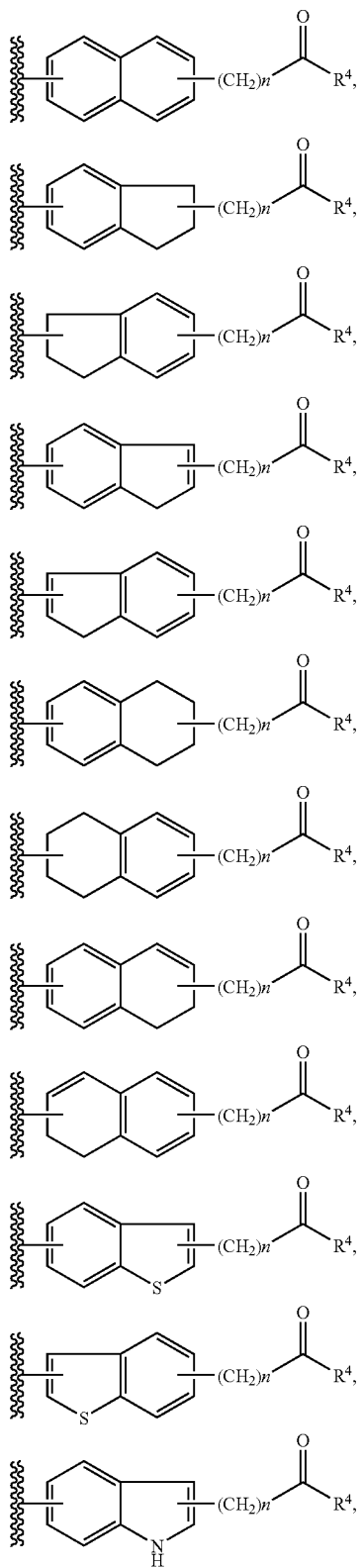
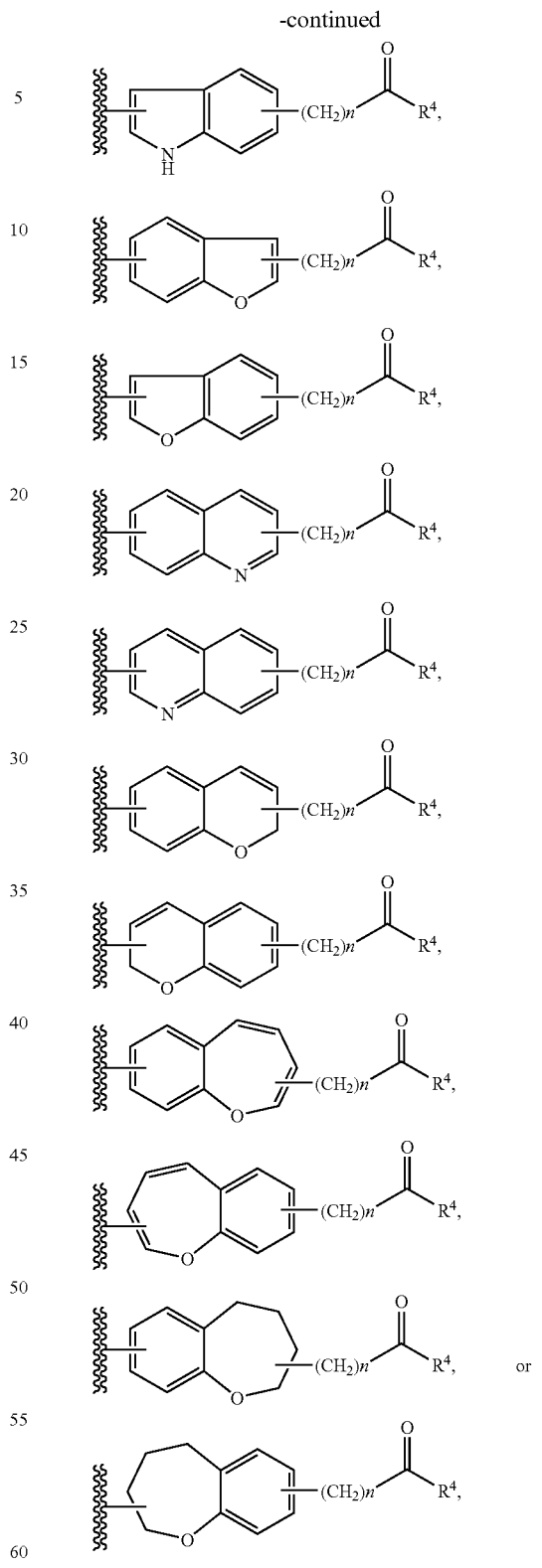
wherein $R^4$ is hydroxy, lower alkyloxy, or optionally substituted amino; n is an integer of 0 to 4;
its prodrug, or their pharmaceutically acceptable salt, or solvate thereof.

20) A compound of the general formula (IV):

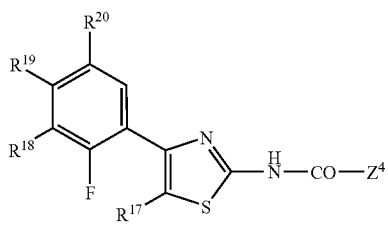

wherein $R^{17}$ is hydrogen atom, C1–C3 alkyl, trifluoromethyl, or halogen atom;

$R^{18}$, $R^{19}$, and $R^{20}$ are each independently hydrogen atom, alkyl optionally substituted with one or more substituent(s) selected from substituent group B, cycloalkyl, alkyloxy optionally substituted with one or more substituent(s) selected from substituent group B, alkylthio, halogen atom, phenyl optionally substituted with one or more substituent(s) selected from substituent group C, heteroaryl optionally substituted with one or more substituent(s) selected from substituent group C, or nonaromatic heterocyclic group optionally substituted with one or more substituent(s) selected from substituent group C;

substituent group B consists of cycloalkyl, hydroxy, alkyloxy, halogen atom, carboxy, lower alkyloxycarbonyl, aryloxycarbonyl, optionally substituted amino, phenyl optionally substituted with one or more substituent(s) selected from substituent group C, non-aromatic heterocyclic group, and heteroaryl, substituent group C consisits of hydroxy, alkyl, halogen atom, halo(lower)alkyl, carboxy, lower alkyloxycarbonyl, alkyloxy, optionally substituted amino, non-aromatic heterocyclic group, and heteroaryl;

$Z^4$ is a group represented by the following formula optionally substituted with lower alkyl, halogen atom, hydroxy, methylene, or oxo:

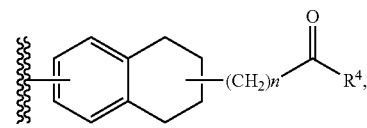

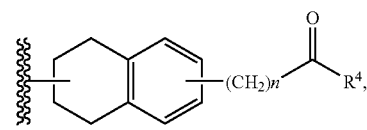

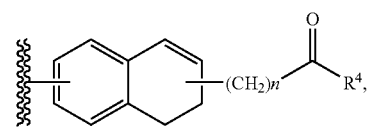

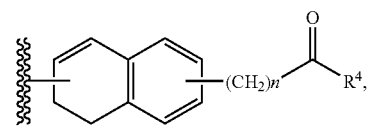

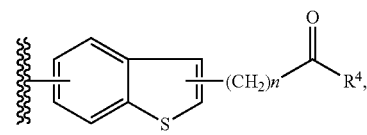

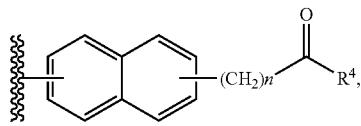

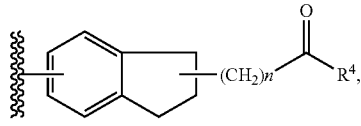

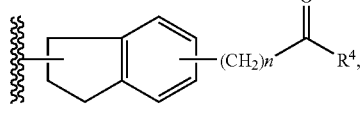

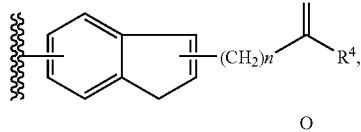

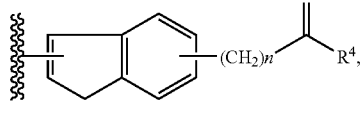

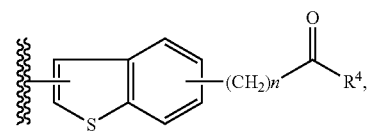

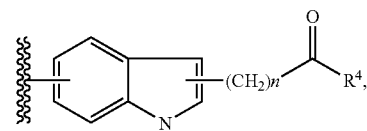

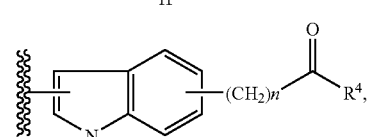

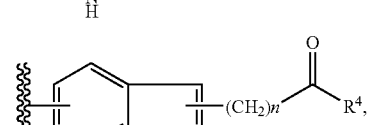

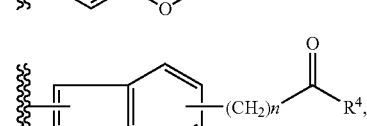

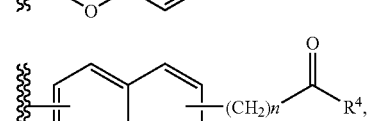

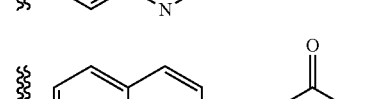

-continued

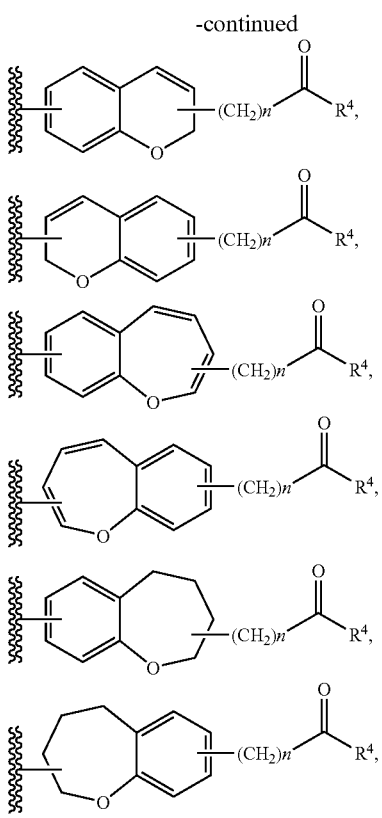

wherein R⁴ is hydroxy, lower alkyloxy, or optionally substituted amino; n is an integer of 0 to 4;

its prodrug, or their pharmaceutically acceptable salt, or solvate thereof.

21) A compound of the general formula (V):

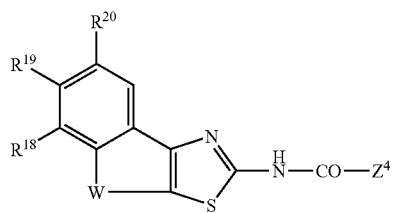

(V)

wherein $R^{18}$, $R^{19}$, and $R^{20}$ are each independently hydrogen atom, alkyl optionally substituted with one or more substituent(s) selected from substituent group B, cycloalkyl, alkyloxy optionally substituted with one or more substituent(s) selected from substituent group B, alkylthio, halogen atom, phenyl optionally substituted with one or more substituent(s) selected from substituent group C, heteroaryl optionally substituted with one or more substituent(s) selected from substituent group C, or nonaromatic heterocyclic group optionally substituted with one or more substituent(s) selected from substituent group C;

substituent group B consists of cycloalkyl, hydroxy, alkyloxy, halogen atom, carboxy, lower alkyloxycarbonyl, aryloxycarbonyl, optionally substituted amino, phenyl optionally substituted with one or more substituent(s) selected from substituent group C, non-aromatic heterocyclic group, and heteroaryl, substituent group C consisits of hydroxy, alkyl, halogen atom, halo(lower)alkyl, carboxy, lower alkyloxycarbonyl, alkyloxy, optionally substituted amino, non-aromatic heterocyclic group, and heteroaryl;

$Z^4$ is a group represented by the following formula optionally substituted with lower alkyl, halogen atom, hydroxy, methylene, or oxo:

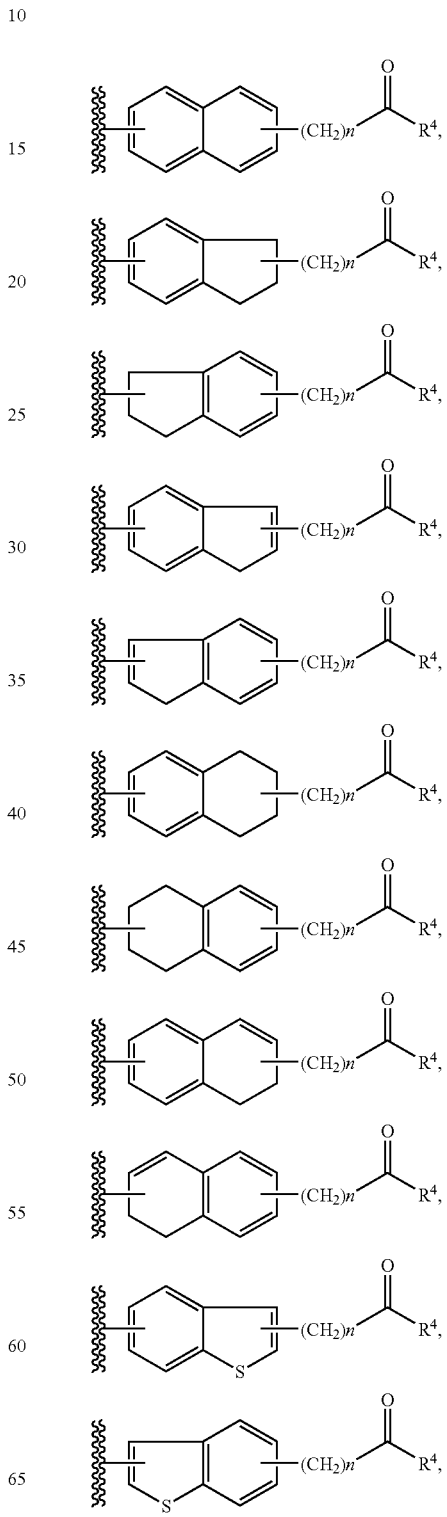

-continued

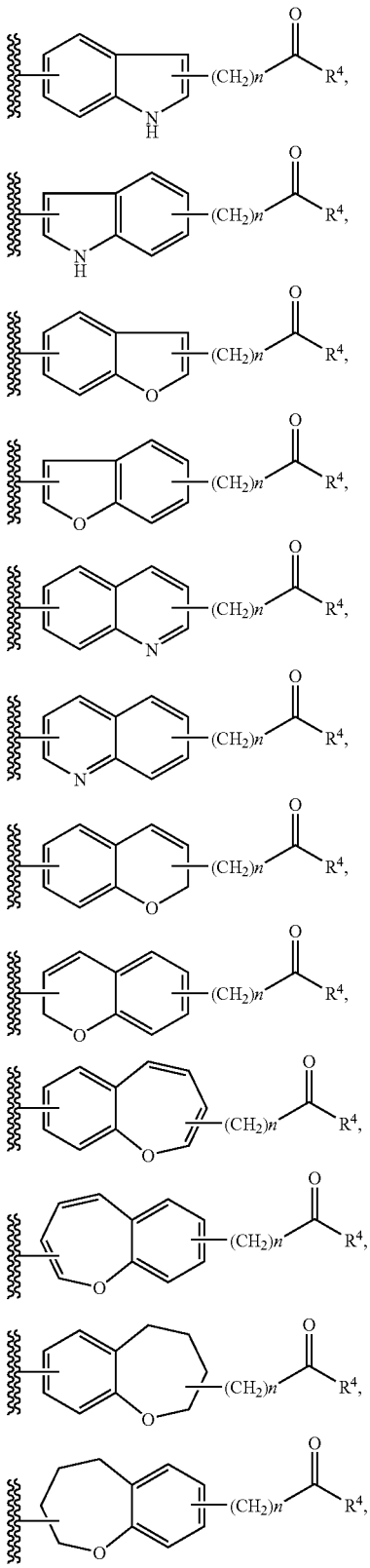

wherein $R^4$ is hydroxy, lower alkyloxy, or optionally substituted amino; n is an integer of 0 to 4;

W is —(CH$_2$—, —CH$_2$CH$_2$—, —CH$_2$CH$_2$CH$_2$—, —OCH$_2$—, or —SCH$_2$—;

its prodrug, or their pharmaceutically acceptable salt, or solvate thereof.

22) A pharmaceutical composition containing as an active ingredient a compound of any one of 13) to 21).

23) A pharmaceutical composition exhibiting thrombopoietin receptor agonism which contains as an active ingredient a compound of any one of 13) to 21).

24) A platelet production modifier containing as an active ingredient a compound of any one of 13) to 21).

25) Use of a compound of any one of 13) to 21), for preparation of a medicine for modifying platelet production.

26) A method for modifying platelet production of a mammal, including a human, which comprises administration to said mammal of a compound of any one of 13) to 21) in a therapeutically effective amount.

In the present specification, the term "halogen" means fluoro, chloro, bromo, and iodo. Preferable are fluoro, chloro and bromo.

In the present specification, the term "alkyl" employed alone or in combination with other terms means a straight- or branched chain monovalent hydrocarbon group having 1 to 15 carbon atom(s). Examples of alkyl include methyl, ethyl, n-propyl, isopropyl, n-butyl, isobutyl, sec-butyl, tert-butyl, n-pentyl, isopentyl, neo-pentyl, n-hexyl, isohexyl, n-heptyl, n-octyl, n-nonanyl, n-decanyl, n-undecanyl, n-dodecanyl, n-tridecanyl, n-tetradecanyl, n-pentadecanyl, and the like. C1 to C10 alkyl is preferred. C1 to C6 alkyl is more preferred.

In the present specification, the term "lower alkyl" employed alone or in combination with other terms means a straight- or branched chain monovalent hydrocarbon group having 1 to 8 carbon atom(s). Examples of lower alkyl include methyl, ethyl, n-propyl, isopropyl, n-butyl, isobutyl, secbutyl, tert-butyl, n-pentyl, isopentyl, neo-pentyl, n-hexyl, isohexyl, n-heptyl, n-octyl, and the like. C1 to C6 alkyl is preferred. C1 to C3 alkyl is more preferred.

In the present specification, the term "cycloalkane" employed alone or in combination with other terms means a cycloalkane having the designating carbon atom(s). Examples of cycloalkane include cyclopropane, cyclobutane, cyclopentane, cyclohexane, cycloheptane, cyclooctane.

In the present specification, the term "cycloalkyl" employed alone or in combination with other terms means a cycloalkyl having 3 to 8 carbon atoms. Examples of cycloalkyl include cyclopropyl, cyclobutyl, cyclopentyl, cyclohexyl, cycloheptyl, cyclooctyl. C5 to C6 cycloalkyl is preferred.

In the present specification, the term "cycloalkenyl" means a mono cycloalkenyl having 3 to 8 carbon atoms. Examples of cycloalkenyl include cyclopropenyl, cyclobutenyl, cyclopentenyl, cyclohexenyl, cycloheptenyl, cyclooctenyl. C5 to C6 cycloalkenyl is preferred.

The term "lower alkenyl" in the present specification means a straight- or branched chain monovalent hydrocarbon group having 2 to 8 carbon atoms and one or more double bond. Examples of lower alkenyl include vinyl, allyl, 1-propenyl, 2-propenyl, a variety of butenyl isomers and the like. C2 to C6 alkenyl is preferred. C2 to C4 alkenyl is more preferred.

In the present specification, the term "cycloalkene" employed alone or in combination with other terms means a cycloalkene having the designating carbon atom(s).

Examples of cycloalkene include cyclopropene, cyclobutene, cyclopentene, cyclohexene, cycloheptene, cyclooctene.

The term "lower alkynyl" used in the present specification means a straight or branched chain monovalent hydrocarbon group having 2 to 8 carbon atoms and one or more triple bond. Examples of lower alkynyl include ethynyl, 1-propynyl, 2-propynyl, 1-butynyl, 2-butynyl, 3-butynyl, 1-pentynyl, 2-pentynyl, a variety of pentynyl isomers and the like. C2 to C6 alkynyl is preferred. C2 to C4 alkynyl is more preferred.

In the present specification, the term "aryl" employed alone or in combination with other terms means monocyclic or condensed ring aromatic hydrocarbons. Examples of aryl include phenyl, 1-naphtyl, 2-naphtyl, anthryl, and the like.

In the present specification, the term "carbocyclic group" employed alone or in combination with other terms means a ring derived from the above mentioned "cycloalkyl", the above mentioned "aryl", and the above mentioned "cycloalkenyl"

Preferable are cyclopentane, cyclohexane, cyclopentene, cyclohexene, benzene ring, and the like as carbocyclic group for $Z^1$, The term "aralkyl" herein used means the above mentioned "lower alkyl" substituted with one or more of the above mentioned "aryl" at any possible position. Examples of the aralkyl are benzyl, phenethyl (e.g., 2-phenethyl and the like), phenylpropyl (e.g., 3-phenylpropyl and the like), naphthylmethyl (e.g., 1-naphthylmethyl, 2-naphthylmethyl, and the like), anthrylmethyl (e.g., 9-anthrylm ethyl and the like), and the like. Benzyl and phenylethy are preferred.

In the present specification, the term "non-aromatic heterocyclic group" employed alone or in combination with other terms means a 5- to 7-membered non-aromatic ring group which contains one or more hetero atoms selected from the group consisting of oxygen, sulfur, and nitrogen atoms in the ring and a condensed ring group formed by condensing two or more of the 5- to 7-membered non-aromatic ring. Examples of the non-aromatic heterocyclic group are pyrrolidinyl (e.g., 1-pyrrolidinyl, 2-pyrrolidinyl), pyrrolinyl (e.g., 3-pyrrolinyl), imidazolidinyl (e.g., 2-imidazolidinyl), imidazolinyl (e.g., imidazolinyl), pyrazolidinyl (e.g., 1-pyrazolidinyl, 2-pyrazolidinyl), pyrazolinyl (e.g., pyrazolinyl), piperidinyl (e.g., piperidino, 2-piperidinyl), piperazinyl (e.g., 1-piperazinyl), indolynyl (e.g., 1-indolynyl), isoindolinyl (e.g., isoindolinyl), morpholinyl (e.g., morpholino, 3-morpholinyl), tetrahydrofuranyl, dihydropyranyl, tetrahydropyranyl, tetrahydrothienyl, dihydrothiopyranyl, tetrahydrothiofurany, oxepinyl, dihydrooxepinyl, tetrahydrooxepinyl, oxepanyl, and the like.

Preferable are morpholino, piperazino, pyrrolidino, teterahydrofuranyl, tetrahydropyranyl, and the like as "non-aromatic heterocyclic group" for $R^{12}$, $R^{13}$, $R^{14}$, $R^{15}$, $R^{16}$, $R^{18}$, $R^{19}$, and $R^{20}$.

Preferable are morpholino, piperazino, piperidino, teterahydrofuranyl, tetrahydropyranyl, and the like as "non-aromatic heterocyclic group" for substituent group B.

Preferable are morpholino, piperazino, piperidino, pyrrolidino, teterahydrofuranyl, tetrahydropyranyl, and the like as "non-aromatic heterocyclic group" for substituent group C.

In the present specification, the term "heteroaryl" employed alone or in combination with other terms means a 5- to 6-membered aromatic heterocyclic group which contains one or more hetero atoms selected from the group consisting of oxygen, sulfur, and nitrogen atoms in the ring and may be fused with above mentioned "cycloalkyl", above mentioned "aryl", above mentioned "non-aromatic heterocyclic group", and other heteroaryl at any possible position. The heteroaryl, monocyclic or fused ring, may be bonded at any possible position. Examples of the heteroaryl are pyrrolyl (e.g., 1-pyrrolyl, 2-pyrrolyl, 3-pyrrolyl), furyl (e.g., 2-furyl, 3-furyl), thienyl (e.g., 2-thienyl 3-thienyl), imidazolyl (e.g., 2-imidazolyl, 4-imidazolyl), pyrazolyl (e.g., 1-pyrazolyl, 3-pyrazolyl), isothiazolyl (e.g., 3-isothiazolyl), isoxazolyl (e.g., 3-isoxazolyl), oxazolyl (e.g., 2-oxazolyl), thiazolyl (e.g., 2-thiazolyl), pyridyl (e.g., 2-pyridyl, 3-pyridyl, 4-pyridyl), pyrazinyl (e.g., 2-pyrazinyl), pyrimidinyl (e.g., 2-pyrimidinyl, 4-pyrimidinyl), pyridazinyl (e.g., 3-pyridazinyl), tetrazolyl (e.g., 1H-tetrazolyl), oxadiazolyl (e.g., 1,3,4-oxadiazolyl), thiadiazolyl (e.g., 1,3,4-thiadiazolyl), indolizinyl (e.g., 2-indolizinyl, 6-indolizinyl), isoindolyl (2-isoindolyl), indolyl (e.g., 1-indolyl, 2-indolyl, 3-indolyl), indazolyl (e.g., 3-indazolyl), puriyl (e.g., 8-puriyl), quinolizinyl (e.g., 2-quinolizinyl), isoquinolyl (e.g., 3-isoquinolyl), quinolyl (e.g., 3-quinolyl, 5-quinolyl), phthalazinyl (e.g., 1-phthalazinyl), naphthyridinyl (e.g., 2-naphthyridinyl), quinolanyl (2-quinolanyl), quinazolinyl (e.g., 2-quinazolinyl), cinnolinyl (e.g., 3-cinnolinyl), pteridinyl (e.g., 2-pteridinyl), carbazolyl (e.g., 2-carbazolyl, 4-carbazolyl), phenanthridinyl (e.g., 2-phenanthridinyl, 3-phenanthridinyl), acridinyl (e.g., 1-acridinyl, 2-acridinyl), dibenzofuranyl (e.g., 1-dibenzofuranyl, 2-dibenzofuranyl), benzimidazolyl (e.g., 2-benzimidazolyl), benzisoxazolyl (e.g., 3-benzisoxazolyl), benzoxazolyl (e.g., 2-benzoxazolyl), benzoxadiazolyl (e.g., 4-benzoxadiazolyl), benzisothiazolyl (e.g., 3-benzisothiazolyl), benzothiazolyl (e.g., 2-benzothiazolyl), benzofuryl (e.g., 3-benzofuryl), benzothienyl (e.g., 2-benzothienyl), 4,5-dihydronaphtho[1,2-d]thiazolyl, 4H-chromeno[4,3-d]thiazolyl, 4H-thiochromeno[4,3-d]thiazolyl, 4,5-dihydrothiazo[5,4-c]quinolyl, 8H-indeno[1,2-d]thiazolyl, 5,6-dihydro-4H-3-thia-1-aza-benzo[e]azurenyl and the like.

Preferable are thiazolyl, isoxazolyl, thienyl, carbazolyl, benzothiazolyl, pyridyl, pyrazolyl, and the like as "heteroaryl" for $X^1$. More preferable are thiazolyl, pyridyl, and the like.

Preferable are pyridyl, thienyl, furyl, pyrimidinyl, imidazolyl, thiazolyl, oxazolyl, triazolyl, and the like as "heteroaryl" for $R^1$ and $R^2$.

Preferable are pyridyl, thienyl, furyl, pyrimidinyl, imidazolyl, thiazolyl, oxazolyl, triazolyl, and the like as "heteroaryl" for $R^{12}$, $R^{13}$, $R^{14}$, $R^{15}$, $R^{16}$, $R^{18}$, $R^{19}$, and $R^{20}$.

Preferable are pyridyl, pyrazolyl, pyrimidinyl, imidazolyl, oxazolyl, thiazolyl, furyl, thienyl, and the like as "heteroaryl" for substituent group B.

Preferable are pyridyl, pyrazolyl, imidazolyl, and the like as "heteroaryl" for substituent group C.

In the present specification, the term "heterocyclic group" employed alone or in combination with other terms means the ring derived from the above mentioned "non-aromatic heterocyclic group" and the above mentioned "heteroaryl".

Examples of "heterocyclic group" for $Z^1$ include teterahydrofuranyl, tetrahydrothienyl, pyrrolidinyl, furyl, thienyl, pyrrolyl, oxazolyl, thiazolyl, pyridyl, dihydropyranyl, teterahydropyranyl, dihydrothiopyranyl, teterahydrothiofuranyl, oxepinyl, dihydrooxepinyl, teterahydrooxepinyl, oxepanyl, and the like.

In the present specification, the term "5- to 7-membered heterocyclic group which contains one or more hetero atoms selected from the group consisting of oxygen, sulfur, and nitrogen atoms in the ring" means the above mentioned "non-aromatic heterocyclic group" and the above mentioned "heteroaryl" which contains one or more hetero atoms selected from the group consisting of oxygen, sulfur, and nitrogen atoms in the ring.

In the present specification, the term "fused cyclic group formed by fusing the same or different two ring selected from optionally substituted carbocyclic group and optionally substituted heterocyclic group" includes the following fused cyclic groups and the like. These fused cyclic groups can be bonded to $Y^1$ at any possible position.

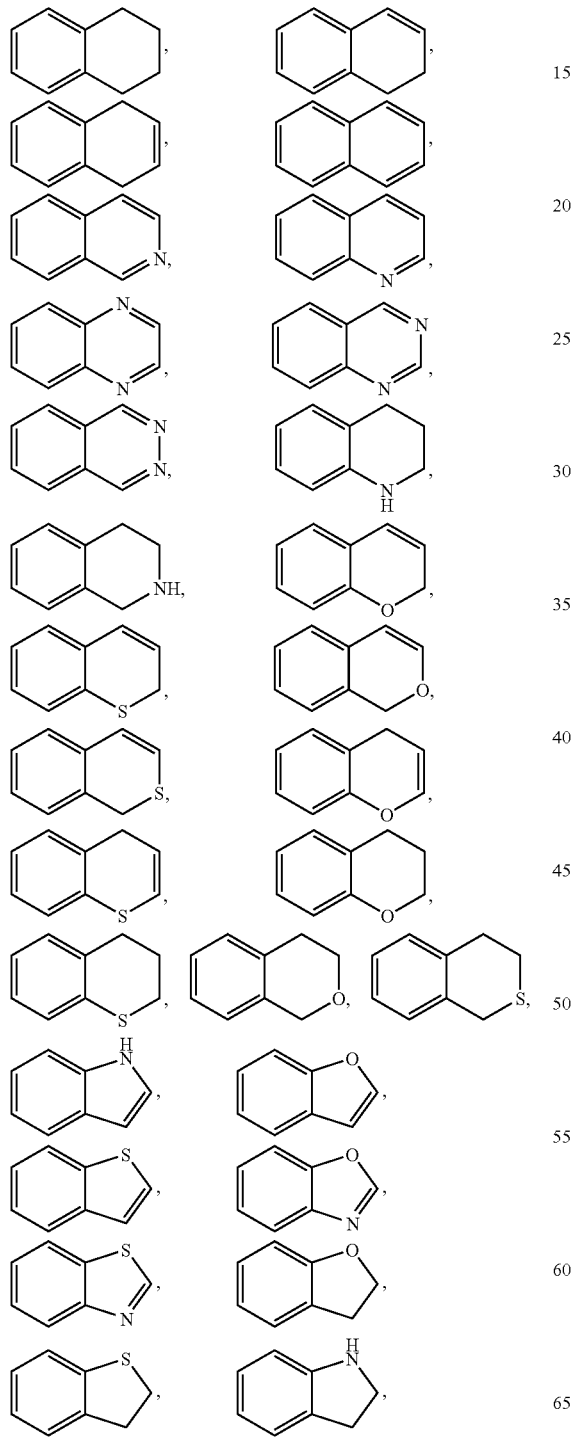

-continued

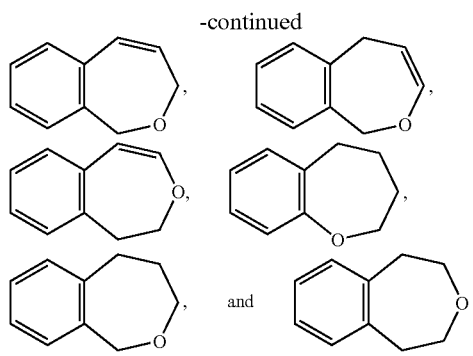

In the present specification, the term "5-membered heteroaryl" means a 5-membered aromatic heterocyclic group which contains one or more hetero atoms selected from the group consisting of oxygen, sulfur, and nitrogen atoms. Examples of the 5-membered heteroaryl are thienyl, furyl, pyrrolyl, imidazolyl, pyrazolyl, isothiazolyl, isoxazolyl, thiazolyl, oxazolyl, 1,2,3-triazolyl, 1,2,4-triazolyl, 1,2,4-thiadiazolyl, 1,3,4-thiadiazolyl, 1,2,4-oxadiazolyl, 1,3,4-oxadiazolyl, and the like. Preferable is thiazolyl.

The term "heteroarylalkyl" herein used means the above mentioned "lower alkyl" substituted with one or more the above mentioned "heteroaryl" at any possible position. Examples of the heteroarylalkyl are thienylmethyl (e.g., 2-thienylmethyl), thienylethyl (e.g., 2-(thiophen-2-yl)ethyl), furylmethyl (e.g., 2-furylmethyl), furylethyl (e.g., 2-(furan-2-yl)ethyl), pyrrolylmethyl (e.g., 2-pyrrolylmethyl), pyrrolylethyl (e.g., 2-(pyrrol-2-yl)ethyl), imidazolylmethyl (e.g., 2-imidazolylmethyl, 4-imidazolylmethyl), imidazolylethyl (e.g., 2-(imidazol-2-yl)ethyl), pyrazolylmethyl (e.g., 3-pyrazolylmethyl), pyrazolylethyl (e.g., 2-(pyrazol-3-yl)ethyl), thiazolylmethyl (e.g., 2-thiazolylmethyl), thiazolylethyl (e.g., 2-(thiazol-2-yl)ethyl), isothiazolylmethyl (e.g., 3-thiazolylmethyl), isoxazolylmethyl (e.g., 3-isoxazolylmethyl), oxazolylmethyl (e.g., 2-oxazolylmethyl), oxazolylethyl (e.g., 2-(oxazol-2-yl)ethyl), pyridylmethyl (e.g., 2-pyridylmethyl, 3-pyridylmethyl, 4-pyridylmethyl), pyridylethyl (e.g., 2-pyridylethyl) and the like.

The term "alkyloxy" herein used are methyloxy, ethyloxy, n-propyloxy, isopropyloxy, n-butyloxy, isobutyloxy, sec-butyloxy, tert-butyloxy, n-pentyloxy, n-hexyloxy, n-heptyloxy, n-octyloxy, n-nonanyloxy, n-decanyloxy, and the like. Methyloxy, ethyloxy, n-propyloxy, isopropyloxy and n-butyloxy are preferred.

The term "lower alkyloxy" herein used are methyloxy, ethyloxy, n-propyloxy, isopropyloxy, n-butyloxy, isobutyloxy, sec-butyloxy, tert-butyloxy, and the like. Methyloxy, ethyloxy, n-propyloxy, isopropyloxy and n-butyloxy are preferred.

The term "lower alkylthio" herein used are methylthio, ethylthio, and the like.

The term "lower alkyloxycarbonyl" herein used are methyloxycarbonyl, ethyloxycarbonyl, n-propyloxycarbonyl, isopropyloxycarbonyl, n-butyloxycarbonyl, t-butyloxycarbonyl, n-pentyloxycarbonyl and the like.

The term "aryloxycarbonyl" herein used are phenyloxycarbonyl, 1-naphthyloxycarbonyl, 2-naphthyloxycarbonyl, and the like.

In the present specification, the term "acyl" employed alone or in combination with other terms includes alkylcarbonyl in which alkyl group is the above mentioned "lower alkyl" and arylcarbonyl in which aryl group is the above mentioned "aryl". Examples of the acyl are acetyl, propyonyl, benzoyl, and the like. "Lower alkyl" and "aryl" may be substituted respectively with substituents mentioned below.

In the present specification, the term "halo(lower)alkyl" employed alone or in combination with other terms includes the above mentioned "lower alkyl" which is substituted with the above mentioned "halogen" at 1 to 8 positions, preferably, at 1 to 5. Examples of the halo(lower)alkyl include trifluoromethyl, trichloromethyl, difluoroethyl, trifluoroethyl, dichloroethyl, trichloroethyl, and the like. Preferable is trifluoromethyl.

The term "halo(lower)alkyloxy" herein used are trifluoromethyloxy, trichloromethyloxy, difluoroethyloxy, trifluoroethyloxy, dichloroethyloxy, trichloroethyloxy, and the like. Preferable is trifluoromethyloxy.

Examples of the term "acyloxy" herein used are acetyloxy, propionyloxy, benzoyloxy and the like.

Examples of the term "lower alkylsilyl" herein used are triethylsilyl, t-butyldimethylsilyl, and the like.

Example of the term "methylene" herein used is methylidene, and chloromethylene is excluded.

In the present specification, the term "optionally substituted amino" employed alone or in combination with other terms includes amino substituted with one or two of the above mentioned "lower alkyl", "aryl", "aralkyl", "heteroaryl", "heteroarylalkyl" or "acyl". Examples of the optionally substituted amino include amino, methylamino, dimethylamino, ethylmethylamino, diethylamino, benzylamino, acetylamino, benzoylamino and the like. Preferable are amino, methylamino, dimethylamino, ethylmethylamino, diethylamino and acetylamino.

Examples of the term "optionally substituted aminocarbonyl" herein used are aminocarbonyl, methylaminocarbonyl, dimethylaminocarbonyl, ethylmethylaminocarbonyl, diethylaminocarbonyl and the like. Preferable are aminocarbonyl, methylaminocarbonyl, and dimethylaminocarbonyl.

In the present specification, the term "optionally substituted ureide" includes ureide substituted with one or more of the above mentioned "lower alkyl", "aryl", "aralkyl", "heteroaryl", "heteroarylalkyl" or "acyl".

The substituents of "optionally substituted lower alkyl" include cycloalkyl, lower alkenyl, lower alkyliden, hydroxy, lower alkyloxy, mercapto, lower alkylthio, halogen, nitro, cyano, carboxy, lower alkyloxycarbonyl, halo(lower)alkyl, halo(lower)alkyloxy, optionally substituted amino, optionally substituted aminocarbonyl, acyl, acyloxy, optionally substituted non-aromatic heterocyclic group, aryloxy (e.g., phenyloxy), aralkyloxy (e.g., benzyloxy), lower alkylsulfonyl, guanidino, azo group, optionally substituted ureide, =N—O— (acyl) and the like. These substituents are able to locate at one or more of any possible positions.

Preferable are halogen atom, and halo(lower)alkyl, as substituents of "optionally substituted lower alkyl" for $R^C$ and $R^D$.

Preferable are lower alkyloxycarbonyl and halogen atom as substituents of "optionally substituted lower alkyl" for $R^1$, $R^2$, and $R^5$.

Preferable are cycloalkyl, lower alkenyl, lower alkylidenel and the like as substituents of "optionally substituted lower alkyl" for $R^3$.

The substituents of "optionally substituted lower alkyloxy" and "optionally substituted lower alkylthio" include cycloalkyl, lower alkenyl, lower alkyliden, hydroxy, lower alkyloxy, mercapto, lower alkylthio, halogen, nitro, cyano, carboxy, lower alkyloxycarbonyl, halo(lower)alkyl, halo(lower)alkyloxy, optionally substituted amino, optionally substituted aminocarbonyl, acyl, acyloxy, optionally substituted non-aromatic heterocyclic group, aryloxy (e.g., phenyloxy), aralkyloxy (e.g., benzyloxy), lower alkylsulfonyl, guanidino, azo group, optionally substituted ureide, =N—O-(acyl) and the like. These substituents are able to locate at one or more of any possible positions.

The substituents of "optionally substituted lower alkenyl" and "optionally substituted lower alknyl" include cycloalkyl, lower alkenyl, lower alkyliden, hydroxy, lower alkyloxy, mercapto, lower alkylthio, halogen, nitro, cyano, carboxy, lower alkyloxycarbonyl, halo(lower)alkyl, halo(lower)alkyloxy, optionally substituted amino, optionally substituted aminocarbonyl, acyl, acyloxy, optionally substituted non-aromatic heterocyclic group, aryloxy (e.g., phenyloxy), aralkyloxy (e.g., benzyloxy), lower alkylsulfonyl, guanidino, azo group, optionally substituted ureide, and the like. These substituents are able to locate at one or more of any possible positions.

The substituents of "optionally substituted aryl", "optionally substituted phenyl", "optionally substituted heteroaryl", "optionally substituted 5-membered heteroaryl", "optionally substituted pyridyl", "optionally substituted non-aromatic heterocyclic group", "optionally substituted cycloalkyl", "optionally substituted aralkyl", and "optionally substituted heteroarylalkyl" herein used are optionally substituted alkyl, cycloalkyl, lower alkenyl, lower alkynyl, hydroxy, alkyloxy, aralkyloxy, mercapto, lower alkylthio, halogen, nitro, cyano, carboxy, lower alkyloxycarbonyl, halo(lower)alkyl, halo(lower)alkyloxy, optionally substituted amino, optionally substituted aminocarbonyl, acyl, acyloxy, optionally substituted aryl (which is substituted by halogen atom, carboxy, alkyl, or alkyloxy, and the like), optionally substituted heteroaryl (which is substituted by halogen atom, carboxy, alkyl, or alkyloxy, and the like), optionally substituted non-aromatic heterocyclic group, optionally substituted aralkyl, lower alkylsulfonyl, guanidino, azo group, —N=N-(optionally substituted phenyl) or optionally substituted ureide and the like. These substituents are able to locate at one or more of any possible positions.

The examples of substituents of "optionally substituted aryl" and "optionally substituted aralkyl" for $X^1$ are lower alkyl, hydroxy lower alkyl, hydroxy, lower alkyloxy, lower alkylthio, halogen, nitro, cyano, carboxy, lower halo(lower)alkyl, halo(lower)alkyloxy, aralkyloxy, optionally substituted amino, optionally substituted aminocarbonyl, aryl, heteroaryl, non-aromatic heterocyclic group, —N=N-(phenyl), and the like. Preferable substituents are lower alkyl, hydroxy, lower alkyloxy, lower alkylthio, halogen, halo(lower)alkyl, halo(lower)alkyloxy, aralkyloxy, —N=N-(phenyl), alkylendioxy, and the like.

The examples of "optionally substituted aryl" for $X^1$ are phenyl, 3-methylphenyl, 4-methylphenyl, 3,4-dimethylphenyl, 4-ethylphenyl, 4-t-buylphenyl, 4-n-buylphenyl, 4-n-hexylphenyl, 4-n-octylphenyl., 3,5-di-t-butyl-4-hydroxyphenyl, 4-ethyloxyphenyl, 4-fluorophenyl, 3,4-dichlorophenyl, 3,5-dichlorophenyl, 4-iodophenyl, 4-trifluoromethylphenyl, 4-methylthiophenyl, 4-phenylmethyloxyphenyl, 4-phenyazophenyl, 4-phenylphenyl, 2-naphtyl, benzodioxoryl (e.g., 1,3-benzodioxoryl), and the like.

The substituents of "optionally substituted aryl" for $R^1$ and $R^2$ are halogen atom, optionally substituted alkyl, cycloalkyl, lower alkenyl, lower alkynyl, hydroxy, alkyloxy, mercapto, lower alkylthio, nitro, cyano, carboxy, lower alkyloxycarbonyl, halo(lower)alkyl, halo(lower)alkyloxy, optionally substituted amino, optionally substituted aminocarbonyl, acyl, formyl, acyloxy, optionally substituted aryl, optionally substituted heteroaryl (e.g., pyridyl, imidazolyl), non-aromatic heterocyclic group (e.g., morpholino, piperazinyl), aralkyl, and the like. Preferable are optionally substituted alkyl by one or more substituent(s) selected from substituent group B, cycloalkyl, optionally substituted alkyloxy by one or more substituent(s) selected from substituent group B, alkylthio, halogen atom, optionally substituted phenyl by one or more substituent(s) selected from substituent group C, optionally substituted heteroaryl by one or more substituent(s) selected from substituent group C, optionally substituted non-aromatic heterocyclic group by one or more substituent(s) selected from substituent group C, and the like.

Substituent group B consists of hydroxy, alkyloxy, halogen atom, carboxy, lower alkyloxycarbonyl, aryloxycarbonyl, optionally substituted amino, optionally substituted phenyl by one or more substituent(s) selected from substituent group C, non-aromatic heterocyclic group, and heteroaryl. Substituent group C consists of hydroxy, alkyl, halogen atom, halo(lower)alkyl, carboxy, lower alkyloxycarbonyl, alkyloxy, optionally substituted amino, non-aromatic heterocyclic group, and heteroaryl.

The aryl may be fused with C5–C7 cycloalkane (e.g., cyclopentane, cyclohexane) and non-aromatic heterocyclic group (e.g., tetrahydrofuranyl, 1,3-dioxolyl, 1,4-dioxynyl, pyrrolidinyl) to form indanyl, 1,2,3,4-tetrahydronaphthalene, 1,2,3,4-tetrahydroquinoline, 2,3-dihydrobenzo[1,4]dioxyine, benzo[1,3]dioxsole, 2,3-dihydrobenzofuran, 2,3-dihydro-1H-indole.

The substituents of "optionally substituted heteroaryl" and "optionally substituted heteroarylalkyl" for $X^1$ include optionally substituted alkyl, lower alkenyl (e.g., =CH—CH$_3$), lower alknyl, hydroxy, lower alkyloxy, mercapto, lower alkylthio, halogen, nitro, cyano, carboxy, lower alkyloxycarbonyl, halo(lower)alkyl, halo(lower)alkyloxy, optionally substituted amino, optionally substituted aminocarbonyl, acyl (e.g., optionally substituted aryloxycarbonyl by halogen atom nitro, cyano, and the like) acyloxy, optionally substituted aryl, optionally substituted heteroaryl (e.g., 2-pyridyl, 3-pyridyl, 4-pyridyl, 3-thienyl, 5-methylpyridin-2-yl, 3-quinolyl, 5-chlorothiophen-2-yl, 5-bromothiophen-2-yl), non-aromatic heterocyclic group, aralkyl, =N—O— (acyl) and the like. Preferable are optionally substituted lower alkyl, lower alkenyl, lower alkyloxycarbonyl, optionally substituted phenyl, heteroaryl, =N—O—(acyl) and the like.

In the case of heteroatom is nitrogen atom, the nitrogen atom may be substituted by alkyl, oxo, and the like.

The substituents of "optionally substituted 5-membered heteroaryl" for $X^2$ include optionally substituted lower alkyl, lower alkenyl (e.g., =CH—CH$_3$), lower alkynyl, hydroxy, lower alkyloxy, mercapto, lower alkylthio, halogen, nitro, cyano, carboxy, lower alkyloxycarbonyl, halo(lower)alkyl, halo(lower)alkyloxy, optionally substituted amino, optionally substituted aminocarbonyl, acyl (e.g., aryloxycarbonyl optionally substituted with halogen, nitro, cyano and the like), acyloxy, optionally substituted phenyl, aryl, optionally substituted heteroaryl (e.g., 2-pyridyl, 3-pyridyl, 4-pyridyl, 3-thienyl, 5-methylpyridine-2-yl, 3-quinolyl, 5-chlorothiophene-2-yl, 5-bromothiophene-2-yl), non-aromatic heterocyclic group, aralkyl, =N—O-(acyl), and the like. Preferable are optionally substituted alkyl by one or more substituent(s) selected from substituent group B, cycloalkyl, optionally substituted alkyloxy by one or more substituent(s) selected from substituent group B, alkylthio, halogen atom, optionally substituted phenyl by one or more substituent(s) selected from substituent group C, optionally substituted heteroaryl by one or more substituent(s) selected from substituent group C, or optionally substituted non-aromatic heterocyclic group by one or more substituent(s) selected from substituent group C, and the like. Substituent group B consists of hydroxy, alkyloxy, halogen atom, carboxy, lower alkyloxycarbonyl, aryloxycarbonyl, optionally substituted amino, optionally substituted phenyl by one or more substituent(s) selected from substituent group C, non-aromatic heterocyclic group, and heteroaryl, Substituent group C consists of hydroxy, alkyl, halogen atom, halo (lower)alkyl, carboxy, lower alkyloxycarbonyl, alkyloxy, optionally substituted amino, non-aromatic heterocyclic group, and heteroaryl, The substituents of "optionally substituted heteroaryl" for $R^1$ and $R^2$ include halogen atom, optionally substituted alkyl, cycloalkyl, lower alkenyl, lower alkynyl, hydroxy, lower alkyloxy, mercapto, lower alkylthio, nitro, cyano, carboxy, lower alkyloxycarbonyl, halo(lower)alkyl, halo (lower)alkyloxy, optionally substituted amino, optionally substituted aminocarbonyl, acyl, formyl, acyloxy, optionally substituted aryl, optionally substituted heteroaryl (e.g., pyridyl, imidazolyl), non-aromatic heterocyclic group (e.g., morpholino, piperazinyl), aralkyl, and the like. Preferable are optionally substituted alkyl by one or more substituent(s) selected from substituent group B, cycloalkyl, optionally substituted alkyloxy by one or more substituent(s) selected from substituent group B, alkylthio, halogen atom, optionally substituted phenyl by one or more substituent(s) selected from substituent group C, optionally substituted heteroaryl by one or more substituent(s) selected from substituent group C, optionally substituted non-aromatic heterocyclic group by one or more substituent(s) selected from substituent group C, and the like, Substituent group B consists of cycloalkyl, hydroxy, alkyloxy, halogen atom, carboxy, lower alkyloxycarbonyl, aryloxycarbonyl, optionally substituted amino, optionally substituted phenyl by one or more substituent(s) selected from substituent group C, non-aromatic heterocyclic group, and heteroaryl. Substituent group C consists of hydroxy, alkyl, halogen atom, halo(lower)alkyl, carboxy, lower alkyloxycarbonyl, alkyloxy, optionally substituted amino, non-aromatic heterocyclic group, and heteroaryl.

The substituents of "optionally substituted carbocyclic group", "optionally substituted heterocyclic group", "optionally substituted C5–C7 cycloalkane", "optionally substituted C5–C7 cycloalkene", "optionally substituted benzene ring", and "optionally substituted 5- to 7-membered heterocyclic group" herein used are a group represented by the formula: —$(CH_2)_n COR^4$ wherein n is an integer of 0 to 4; $R^4$ is hydroxy, lower alkyloxy, or optionally substituted amino; lower alkyl, halogen atom, halo(lower)alkyl, hydroxy, lower alkyloxy, halo(lower)alkyloxy, methylene, oxo, and the like. These substituents are able to locate at one or more of any possible positions.

In the present specification, the term "$(\alpha)_{\beta\text{-}\gamma}$" means that the number of α present is β to γ. For examples, $(CR^C R^D)_{0\text{-}2}$, $(CH_2)_{0\text{-}2}$, and $(CH_2)_{1\text{-}5}$ mean that $CR^C R^D$ is present 0 to 2, $CH_2$ is present 0 to 2, $CH_2$ is present 1 to 5, respectively.

In the present specification, the term "platelet production modifier" includes a medicine for hemopathy accompanied with the unusual number of platelet. For example the hemopathy is thrombocytopenia (after bone marrow transplantation, after chemotherapy, anaplastic anemia, bone marrow dysplasia syndrome, acquired thrombopenia of intractable sudden thrombocy topenic purpura and the like, congenital thrombopenia of thrombopoietin deficiency and the like) and the like. For example this medicine can be used as a treating agent for decreace platelet number caused by administrating an antitumor agent, or as a preventing agent for the platelet number decreace caused by administrating an antitumor agent.

In the present specification, the term "modifying platelet production" includes 1) increasing the number of platelet decreased by administrating an antitumor agent and the like, 2) maintaining the number of platelet which may be decreased by administrating an antitumor agent and the like, and 3) reducing the ratio of the platelet number decrease caused by administrating an antitumor agent and the like.

The pharmaceuticl composition exhibiting thrombopoietin receptor agonism includes a thrombopoietin receptor agonistic agent.

BEST MODE FOR CARRYING OUT THE INVENTION

Compounds (I) of the invention can be synthesized by the following methods A to B and the similar process.

(Method A)

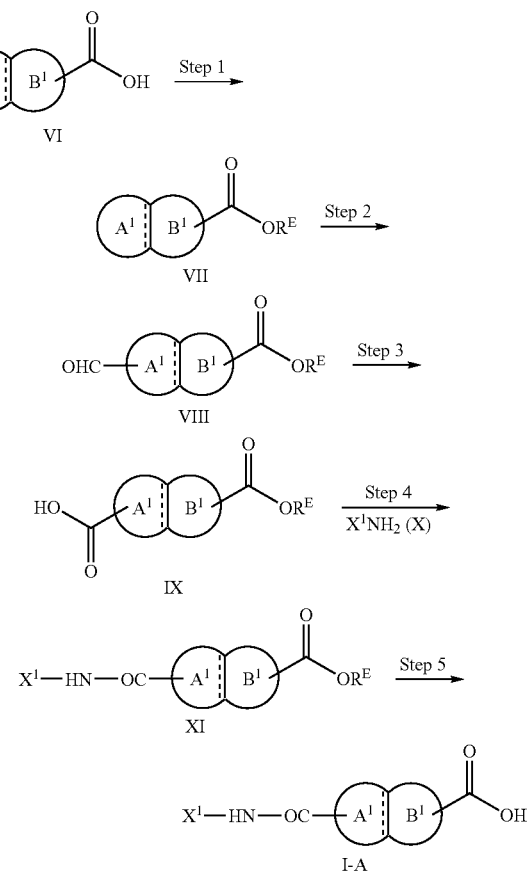

wherein $A^1$, $B^1$, and $X^1$ are as defined above; $R^E$ is a protecting group of hydroxy.

(Step 1)

This step is a process for protecting carboxylic acid with $R^E$. $R^E$ is a protecting group such as methyl and ethyl, which can be removed on basic condition. It can be prepared by usual esterification condition.

(Step 2)

This step is a process for introducing formyl. It can be prepared by usual Vilsmeier reaction.

(Step 3)

This step is a process for oxidizing aldehyde to carboxylic acid. It can be prepared by usual oxidation reaction.

(Step 4)

This step is a process for preparing amide derivative (XI) from carboxylic acid derivative (IX) and amine derivative ($X_1$—$NH_2$) by the method such as active esterification, acid chloride, and mixed acid anhydride. This step is reacted in a solvent such as tetrahydrofuran, dioxane, dichloromethane, toluene, and benzene. The active esterification can be carried out by using 1-hydroxybenzotriazole, hydroxysuccinimide, dimethylaminopyridine, and the like and a condensation reagent such as dicyclohexylcarbodiimide and 1-ethyl-3-(3-dimethylaminopropyl)carbodiimide hydrochloride salt. The acid halide method can be carried out by converting free carboxylic acid to acid chloride with thionyl chloride or oxalyl chloride. The mixed acid anhydride method can be carried out by converting carboxylic acid to mixed acid anhydride with ethylchloroformate, isobutylchloroformate or the like. Triethylamine, pyridine or the like are used as base in these reaction if necessary.

(Step 5)

This step is a process for removing protecting group $R^E$. The protecting group $R^E$ is removed under suitable reaction condition by the method as described in Protective Groups in Organic Synthesis, Theodora W Green (John Wiley & Sons).

(Method B)

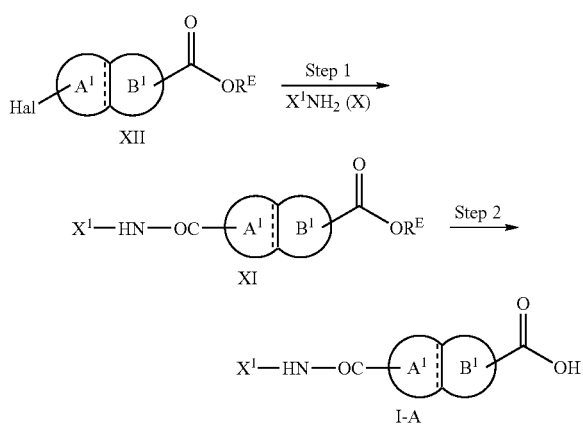

wherein $A^1$, $B^1$, $X^1$, and $R^E$ are as defined above; Hal is halogen atom.

(Step 1)

This step is a process for inserting carbon monooxide to compound (XII) and a process for coupling the obtained compound with amine derivative (X). It can be prepared by the method as described in Bioorganic and Med. Chem. Lett., 10, 443–447 (2000).

(Step 2)

This step is a process for preparing compound (I-A) in a manner similar to Step 5 of Method A.

In the synthesis of a compound (I) wherein $Y^1$ is —N(-alkyl)-CO—; $X^1$ is optionally substituted thiazole represented by the formula or the like;

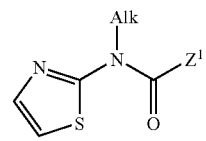

wherein $Z^1$ is as defined above; Alk is lower alkyl, depending the alkylation condition, the following compound may be obtained.

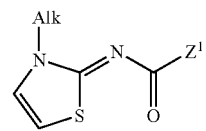

wherein $Z^1$ and Alk are as defined above.

In the case of compound of the general formula (I), (II), (III), (IV), or (V) has a double bond, the compound includes a cis isomer, a trans isomer, and their mixture.

The term "solvate" includes, for example, solvates with organic solvents, hydrates, and the like.

The term "compound of the present invention" herein used includes a pharmaceutically acceptable salt or hydrate thereof. The salt is exemplified by a salt with alkali metals (e.g., lithium, sodium, potassium, and the like), alkaline earth metals (e.g., magnesium, calcium, and the like), ammonium, organic bases, amino acids, mineral acids (e.g., hydrochloric acid, hydrobromic acid, phosphoric acid, sulfuric acid, and the like), or organic acids (e.g., acetic acid, citric acid, maleic acid, fumaric acid, benzenesulfonic acid, p-toluenesulfonic acid, and the like). These salts can be formed by the usual method. These hydrates can coordinate with any water molecules.

Prodrug is a derivative of the compound having a group which can be decomposed chemically or metabolically, and such prodrug is a compound according to the present invention which becOMes pharmaceutically active by means of solvolysis or by placing the compound in vivo under a physiological condition. The method of both selection and manufacture of appropriate prodrug derivatives is described in, for example. Design of Prodrugs, Elsevier, Amsterdam, 1985). For instance, prodrugs such as an ester derivative which is prepared by reacting a basal acid compound with a suitable alcohol, or an amide derivative which is prepared by reacting a basal acid compound with a suitable amine are exemplified when the compounds according to present invention have a carboxylic group. Particularly preferred esters as prodrugs are methyl, ethyl, n-propyl, isopropyl, n-butyl, isobutyl, tert-butyl, morpholinoethyl, and N,N-diethylglycolamido, and the like. For instance, prodrugs such as an acyloxy derivative which is prepared by reacting a basal hydroxy compound with a suitable acyl halide or a suitable acid anhydride, or an amide derivative which is prepared by reacting a basal acid compound with a suitable amine are exemplified when the compounds according to present invention have a hydroxy group. Particularly preferred acyloxy derivatives as prodrugs —$OCOC_2H_5$, —OCO(t-Bu), —$OCOC_{15}H_{31}$, —OCO(m-COONa—Ph), —COCH$_2$CH$_2$COONa, —OCOCH(NH$_2$)CH$_3$, —OCOCH$_2$N(CH$_3$)$_2$, and the like. For instance, prodrugs such as an amide derivative which is prepared by reacting a basal amino compound with a suitable acid halide or a suitable acid anhydride are exemplified when the compounds according to present invention have an amino group. Particularly preferred amide as prodrugs are —NHCO(CH$_2$)$_{20}$CH$_3$, —NHCOCH(NH$_2$)CH$_3$, and the like.

The compound of the present invention is not restricted to any particular isomers but includes all possible isomers and racemic modifications.

The present invention compounds show excellent thrombopoietin receptor agonism as described in examples mentioned later, and may be used as a pharmaceutical composition (platelet production modifier) for hemopathy accompanied with the unusual number of platelet, for example thrombocytopenia (an acquired thrombocytopenia such as after bone marrow transplantation, after chemotherapy, apastic anemia, osteomyelodysplasia syndrome, intractable sudden thrombocy topenic purpura, and congenital thrombocytopenia such as thrombopoietin deficiency) and the like. And the present compounds may be used as a treating and/or preventing agent against disorder of the platelet number by administration of an antitumor agent.

When the compound of the present invention is administered to a person for the treatment of the above diseases, it can be administered orally as powder, granules, tablets, capsules, pilulae, and liquid medicines, or parenterally as injections, suppositories, percutaneous formulations, insufflation, or the like. An effective dose of the compound is formulated by being mixed with appropriate medicinal admixtures such as excipient, binder, penetrant, disintegrators, lubricant, and the like if necessary. Parenteral injections are prepared by sterilizing the compound together with an appropriate carrier.

The dosage varies with the conditions of the patients, administration route, their age, and body weight. In the case of oral administration, the dosage can generally be between 0.1 to 100 mg/kg/day, and preferably 1 to 20 mg/kg/day for adult.

The following examples are provided to further illustrate the present invention and are not to be construed as limiting the scope thereof.

Abbreviations described below are used in the following examples.
Me:methyl
Et:ethyl
n-Pr:n-propyl
i-Pr:isopropyl
c-Pr:cyclopropyl
n-Bu:n-butyl
i-Bu:isobutyl
sec-Bu:sec-butyl
t-Bu:tert-butyl
i-Bu:isobutyl
n-Pen:n-pentyl
c-Pen:cyclopentyl
n-Hex:n-hexyl
c-Hex:cyclohexyl
i-Hex:isohexyl
Ph:phenyl
Bn:benzyl
Bz:benzoyl
Py:pyridyl
Th:thienyl
Ac:acetyl
Z:benzyloxycarbonyl
DMF:N,N-dimethylformamide
THF:tetrahydrofuran

EXAMPLE

Example 1

Preparation of Compound (A-1)

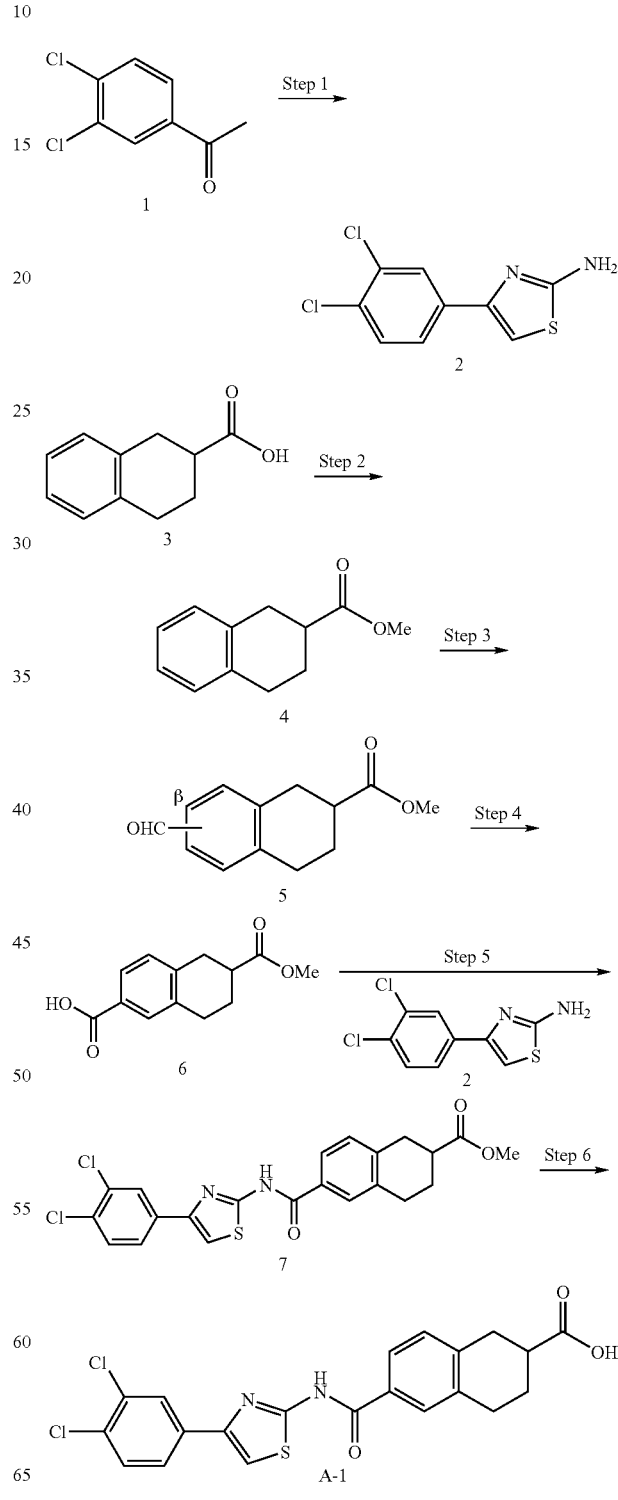

(Step 1)

To a solution of 3',4'-dichloroacetophenone (1) (5.67 g) in 10% methanol-chloroform was added bromine (1.52 mL), and the reaction mixture was stirred at room temperature until a color of bromine was disappeared. The solvent was evaporated under reduced pressure and the residue was dissolved in ethanol again. To the reaction mixture was added thiourea (2.28 g) and the mixture was heated under reflux for 2 h. The solvent was evaporated under reduced pressure and to the residue were added ethyl acetate and water, and the resulting crystal was filtered. To the obtained crystal were added ethyl acetate and a saturated aqueous sodium bicarbonate solution, and the layer was separated. The organic layer was dried and evaporated under reduced pressure to give a compound (2) (3.38 g).

$^1$H NMR (CDCl$_3$, δ ppm): 7.89 (d, 1H, J=2.2 Hz), 7.69 (dd, 1H, J=8.5 Hz, 2.2 Hz), 7.43 (d, 1H, J=8.2 Hz), 6.74 (s, 1H), 5.06 (bs, 2H).

(Step 2)

To a solution of 1,2,3,4-tetrahydronaphthalene-2-carboxylic acid (2.0 g) in methanol (11.1 mL) was added slowly thionyl chloride (1.62 mL) at room temperature, and the reaction mixture was stirred at the same temperature. The solvent was evaporated under reduced pressure and the residue was dissolved in ethyl acetate. The organic layer was washed with a saturated aqueous sodium bicarbonate solution and brine, dried, and evaporated to give a compound (4) (2.29 g) as a brown oil.

$^1$H NMR (CDCl$_3$, δ ppm) 7.03–7.14 (m, 4H), 3.73 (s, 3H), 3.03 (s, 1H), 3.00 (s, 1H), 2.68–2.90 (m, 3H), 2.20 (m, 1H), 1.86 (m, 1H).

(Step 3)

To a solution of compound (4) (2.29 g) in methylene chloride (20 mL) were added tin tetrachloride (2.6 mL) and dichloromethyl methyl ether (2 mL), and the reaction mixture was stirred at room temperature for 1 h. The reaction mixture was poured into ice-water and extracted with chloroform. The organic layer was washed with a saturated aqueous sodium bicarbonate solution and brine, dried, and evaporated. The residue was purified by silica gel column chromatography to give a mixture (5) (611 mg) of isomers at β position of aldehyde as a colorless oil.

$^1$H NMR (CDCl$_3$, δ ppm) 9.94 (s, 1H), 7.59–7.61 (m, 2H), 7.25 (m, 1H), 3.47 3H), 3.10 (s, 1H), 3.08 (s, 1H), 2.70–3.00 (m, 3H), 2.25 (m, 1H), 1.90 (m, 1H).

(Step 4)

To a solution of a mixture (5) (468 mg) in t-butanol/water (5/1, 11.1 mL) were added sodium chlorite (1.14 g), sodium phosphate dibasic (1.48 g), and 2-methyl-2-butene (5.7 mL), and the reaction mixture was stirred at room temperature for 30 min. The reaction mixture was poured into water and extracted with ethyl acetate. The organic layer was washed with a saturated aqueous sodium bicarbonate solution and brine, dried, and evaporated to give a mixture (6) (146 mg) of isomers at β position of carboxylic acid as a white crystal.

$^1$H NMR (CDCl$_3$, δ ppm) 7.81–7.86 (m, 2H), 7.20 (d, 1H, J=8.5 Hz), 3.74 (s, 3H), 3.09 (s, 1H), 3.06 (s, 1H), 2.70–3.00 (m, 3H), 2.25 (m, 1H), 1.90 (m, 1H).

(Step 5)

To a solution of compound (6) in tetrahydrofuran (2 mL) were added oxalyl chloride (20 mL) and one drop of DMF, and the reaction mixture was stirred at room temperature for 30 min. After the solvent was evaporated, to a solution of said acid chloride in dioxane (2 mL) were added a compound (2) (56 mg) and pyridine (16.2 mL), and the reaction mixture was heated under reflux for 1 h. After the solvent was evaporated, the residue was purified by column chromatography to give a compound (7) (27.8 mg) as a white crystal.

$^1$H NMR (CDCl$_3$, δ ppm) 10.70 (bs, 1H), 7.78 (d, 1H, J=2.0 Hz), 7.54–7.59 (m, 2H), 7.52(dd, 1H, J=8.5, 2.0 Hz), 7.36 (d, 1H, J=8.5 Hz), 7.20 (s, 1H), 7.10 (d, 1H, J=8.5 Hz), 3.75 (s, 3H), 3.03 (s, 1H), 3.00 (s, 1H), 2.70–2.87 (m, 3H), 2.25 (m, 1H), 1.85 (m, 1H).

(Step 6)

To a solution of compound (7) (23.1 mg) in tetrahydrofuran/methanol (1/1, 2 mL) was added a 1 mol/L aqueous sodium hydroxide solution (1 mL), and the reaction mixture was stirred for 1 h. After the organic layer was evaporated, 1 mol/L hydrochloric acid was added to the residue, which became to be acidic. The resulting precipitate was filtered, washed with water, and dried to give a compound (A-1) (18.7 mg) as a white crystal.

$^1$H NMR (DMSO-d$_6$, δ ppm) 12.70 (s, 1H), 12.30 (bs, 1H), 8.21 (d, 1H, J=2.0 Hz), 7.94 (dd, 1H, J=8.5, 2.0 Hz), 7.90 (s, 2H), 7.85 (dd, 1H, J=8.0, 1.6 Hz). 7.72 (d, 1H, J=8.5 Hz), 7.28 (d, 1H, J=8.0 Hz), 2.80–3.10 (m, 4H), 2.70 (m, 1H), 2.12 (m, 1H), 1.79 (m, 1H).

By using a various dicarboxylic acid monoesters instead of a compound (6), compounds (A-2) to (A-23) were synthesized in a manner similar to Example 1. Their physical data were shown in Tables 1 to 4.

TABLE 1

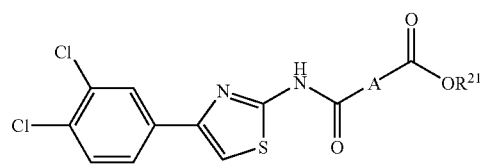

| Compound No. | A | R$^{21}$ | $^1$H-NMR (DMSO d-6) |
|---|---|---|---|
| A-2 | 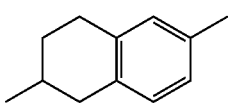 | H | 12.40(bs, 1H), 8.15(d, 1H, J=2.0 Hz), 7.89(dd, 1H, J=8.5, 2.0 Hz), 7.85(s, 1H), 7.69(s, 1H), 7.64–7.74(m, 2H), 7.22(d, 1H, J=7.3 Hz), 2.70–3.10(m, 5H), 2.15(m, 1H), 1.80(m, 1H) |

TABLE 1-continued

Structure: 3,4-dichlorophenyl-thiazol-2-yl-NH-C(=O)-A-C(=O)-OR²¹

| Compound No. | A | R²¹ | ¹H-NMR (DMSO d-6) |
|---|---|---|---|
| A-3 | 7-methyl-tetrahydronaphthalen-2-yl | H | 12.60(s, 1H), 12.30(bs, 1H), 8.21(d, 1H, J=2.0 Hz), 7.94(dd, 1H, J=8.5, 2.0 Hz), 7.92(s, 1H), 7.89(s, 1H), 7.85(d, 1H, J=8.5 Hz), 7.72(d, 1H, J=8.5 Hz), 7.25(d, 1H, J=8.5 Hz), 2.80–3.10(m, 4H), 2.75(m, 1H), 2.10(m, 1H), 1.80(m, 1H) |
| A-4 | 6-methyl-2-fluoro-tetrahydronaphthalen-2-yl | H | 13.50(bs, 1H), 12.70(s, 1H), 8.22(d, 1H, J=2.0 Hz), 7.85–8.00(m, 2H), 7.97 (s, 1H), 7.92(s, 1H), 7.73(d, 1H, J=8.5 Hz), 7.32(d, 1H, J=8.2 Hz), 3.10–3.50 (m, 2H), 2.90–3.00(m, 2H), 2.00–2.30 (m, 2H) |
| A-5 | 6-methyl-2-fluoro-tetrahydronaphthalen-2-yl | CH₃ | 10.30(bs, 1H), 7.86(d, 1H, J=2.0 Hz), 7.65–7.70(m, 2H), 7.58(dd, 1H, J=8.5, 2.0 Hz), 7.42(d, 1H, J=8.5 Hz), 7.21(s, 1H), 7.18(d, 1H, J=8.9 Hz), 3.88(s, 3H), 3.42(dd, 1H, J=37.2, 18.0 Hz), 3.22(dd, 1H, J=18.0, 17.1 Hz), 3.07(m, 1H), 2.90(m, 1H), 2.00–2.45(m, 2H) (CDCl₃) |
| A-6 | 7-methyl-4-oxo-tetrahydronaphthalen-2-yl | H | 13.00(s, 1H), 12.60(bs, 1H), 8.61(d, 1H, J=2.0 Hz), 8.27(dd, 1H, J=8.0, 2.0 Hz), 8.22(d, 1H, J=2.0 Hz), 7.95(dd, 1H, J=8.5, 2.0 Hz), 7.93(s, 1H), 7.73(d, 1H, J=8.5 Hz), 7.60(d, 1H, J=8.0 Hz), 3.18–3.30(m, 3H), 2.80–2.90(m, 2H) |
| A-7 | 7-methyl-4-oxo-tetrahydronaphthalen-2-yl | CH₃ | 10.40(bs, 1H), 8.57(d, 1H, J=2.0 Hz), 8.21(dd, 1H, J=8.0, 2.0 Hz), 7.90(d, 1H, J=2.0 Hz), 7.63(dd, 1H, J=8.5, 2.0 Hz), 7.49(d, 1H, J=8.0 Hz), 7.46(d, 1H, J=8.5 Hz), 7.22(s, 1H), 3.74(s, 3H), 3.20–3.38(m, 3H), 2.85–3.10(m, 2H) (CDCl₃) |

TABLE 2

| Compound No. | A | R²¹ | ¹H-NMR (DMSO d-6) |
|---|---|---|---|
| A-8 | 7-methyl-4-hydroxy-tetrahydronaphthalen-2-yl (2S,4-OH) | CH₃ | 12.75(s, 1H), 8.25(s, 1H), 8.21(d, 1H, J=2.0 Hz), 7.94(dd, 2H, J=8.0, 2.0 Hz), 7.91(s, 1H), 7.72(d, 1H, J= 8.0 Hz), 7.29(d, 1H, J=8.0 Hz), 5.50 (bs, 1H), 4.74(dd, 1H, J=10.0, 5.8 Hz), 3.67(s, 3H), 2.90–3.10(m, 3H), 2.40(m, 1H), 1.70(m, 1H) |
| A-9 | 7-methyl-4-fluoro-tetrahydronaphthalen-2-yl | H | 12.83(s, 1H), 12.55(bs, 1H), 8.18–8.26(m, 2H), 8.08(m, 1H), 7.95(dd, 1H, J=8.5, 2.0 Hz), 7.92(d, 1H, J = 1.2 Hz), 7.73(d, 1H, J=8.5 Hz), 7.43 (m, 1H), 5.80(m, 1H), 3.20(m, 1H), 2.80–3.05(m, 3H), 2.05(m, 1H) |

TABLE 2-continued

| Compound No. | A | $R^{21}$ | $^1$H-NMR (DMSO d-6) |
|---|---|---|---|
| A-10 | | H | 12.84(s, 1H), 12.50(bs, 1H), 8.51(s, 1/2H), 8.22(s, 1H), 8.03(s, 1/2H), 7.89–8.00(m, 3H), 7.72(d, 1H, J=8.6 Hz), 7.40(d, 1/2H, J=8.6 Hz), 7.37 (d, 1/2H, J=8.4 Hz), 6.00(s, 1/2H), 5.91(s, 1/2H), 5.20(s, 1/2H), 2.50–3.20(m, 4H), 2.17(s, 3/2H) |
| A-11 | | CH$_3$ | 9.81(bs, 1H), 8.60(d, 1H, J=1.8 Hz), 8.25(dd, 1H, J=8.5, 1.8 Hz), 7.97(d, 1H, J=2.0 Hz), 7.68(dd, 1H, J=8.2, 2.0 Hz), 7.51(d, 1H, J=8.0 Hz), 7.50 (d, 1H, J=8.3 Hz), 7.25(s, 1H), 5.38 (dd, 1H, J=47.0, 3.9 Hz), 3.73(s, 3H), 3.40–3.70(m, 3H) (CDCl$_3$) |
| A-12 | | H | 13.10(bs, 2H), 10.90(s, 1H), 9.01(s, 1H), 8.24(d, 1H, J=1.8 Hz), 8.10–8.22(m, 3H), 7.97(dd, 1H, J=8.5, 1.8 Hz), 7.95(s, 1H), 7.74(d, 1H, J=8.5 Hz), 7.47(s, 1H) |
| A-13 | | CH$_3$ | 10.40(bs, 1H), 8.20–8.27(m, 2H), 7.86(s, 1H), 7.56–7.63(m, 2H), 7.41 (d, 1H, J=8.5 Hz), 7.23(s, 1H), 3.70 (s, 3H), 3.50(m, 1H), 2.90–3.15(m, 3H), 2.79(m, 1H) (CDCl$_3$) |
| A-14 | | H | 13.00(s, 1H), 12.30(s, 1H), 8.44(d, 1H, J=1.5 Hz), 8.36(dd, 1H, J=8.0, 1.5 Hz), 8.22(d, 1H, J=2.0 Hz), 7.95 (dd, 1H, J=8.5, 2.0 Hz), 7.94(s, 1H), 7.76(d, 1H, J=8.0 Hz), 7.73(d, 1H, J=8.5 Hz), 3.45(m, 1H), 2.70–3.10(m, 4H) |

TABLE 3

| Compound No. | A | $R^{21}$ | $^1$H-NMR (DMSO d-6) |
|---|---|---|---|
| A-15 | | CH$_3$ | 9.90(bs, 1H), 7.91(d, 1H, J=2.0 Hz), 7.76(s, 1H), 7.71(d, 1H, J=8.0 Hz), 7.62(dd, 1H, J=8.5, 2.0 Hz), 7.45(d, 1H, J=8.5 Hz), 7.30(d, 1H, J=8.0 Hz), 7.21(s, 1H), 3.72(s, 3H), 3.15–3.30(m, 2H), 2.96(m, 1H), 2.64–2.80 (m, 2H), 2.53(d, 2H, J=7.4 Hz) (CDCl$_3$) |
| A-16 | | H | 12.60(s, 1H), 12.20(s, 1H), 8.21(d, 1H, J=2.0 Hz), 7.91–8.00(m, 3H), 7.90(s, 1H), 7.72 (d, 1H, J=8.5 Hz), 7.37(d, 1H, J=8.0 Hz), 3.05–3.20(m, 2H), 2.60–2.85(m, 3H), 2.44 (d, 2H, J=7.0 Hz) |
| A-17 | | H | 13.30(bs, 1H), 13.00(s, 1H), 8.88(s, 1H), 8.71(s, 1H), 8.29(d, 1H, J=8.5 Hz), 8.16–8.26(m, 3H), 8.10(d, 1H, J=8.9 Hz), 7.97 (dd, 1H, J=1.7, 8.2 Hz), 7.96(s, 1H), 7.74(d, 1H, J=8.2 Hz) |
| A-18 | | CH$_3$ | 10.30(bs, 1H), 8.66(s, 1H), 8.46(s, 1H), 8.18 (dd, 1H, J=8.5, 1.7 Hz), 8.07(d, 1H, J=8.5 Hz), 8.02(dd, 1H, J=8.5, 1.7 Hz), 7.97(d, 1H, J=8.5 Hz), 7.84(d, 1H, J=1.9 Hz), 7.57 (dd, 1H, J=8.2, 1.9 Hz), 7.39(d, 1H, J=8.2 Hz), 7.23(s, 1H), 4.02(s, 3H) (CDCl$_3$) |

TABLE 3-continued

| Compound No. | A | R²¹ | ¹H-NMR (DMSO d-6) |
|---|---|---|---|
| A-19 | 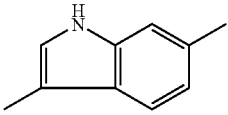 | $CH_3$ | 12.40(s, 1H), 12.30(bs, 1H), 8.79(d, 1H, J=3.4 Hz), 8.33(d, 1H, J=8.5 Hz), 8.21(d, 1H, J=2.0 Hz), 8.15(d, 1H, J=1.5 Hz), 7.94(dd, 1H, J=8.5, 2.0 Hz), 7.85(s, 1H), 7.82(dd, 1H, J=8.5, 1.5 Hz), 7.72(d, 1H, J=8.5 Hz), 3.88(s, 3H) |
| A-20 | 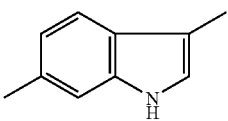 | $CH_3$ | 12.80(s, 1H), 12.40(d, 1H, J=2.7 Hz), 8.33 (s, 1H), 8.32(d, 1H, J=2.7 Hz), 8.23(d, 1H, J=2.0 Hz), 8.11(d, 1H, J=8.2 Hz), 8.00(dd, 1H, J=8.2, 1.5 Hz), 7.96(dd, 1H, J=8.5, 2.0 Hz), 7.91(s, 1H), 7.73(d, 1H, J=8.5 Hz), 3.85(s, 3H) |
| A-21 | 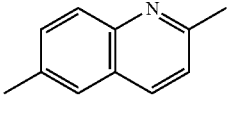 | H | 12.90(bs, 1H), 8.83(s, 1H), 8.48(d, 1H, J=8.5 Hz), 8.32–8.43(m, 2H), 8.23(d, 1H, J=2.0 Hz), 8.20(d, 1H, J=8.5 Hz), 7.96(dd, 1H, J=8.5, 2.0 Hz), 7.90(s, 1H), 7.72(d, 1H, J=8.5 Hz) |
| A-22 | 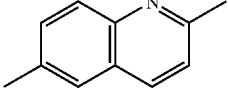 | $CH_3$ | 10.50(bs, 1H), 8.49(d, 1H, J=2.0 Hz), 8.41 (d, 1H, J=8.5 Hz), 8.38(d, 1H, J=8.5 Hz), 8.31(d, 1H, J=8.5 Hz), 8.22(dd, 1H, J=8.5, 2.0 Hz), 7.81(d, 1H, J=2.0 Hz), 7.53(dd, 1H, J=8.5, 2.0 Hz), 7.35(d, 1H, J=8.5 Hz), 7.24 (s, 1H), 4.13(s, 3H) (CDCl₃) |

TABLE 4

| Compound No. | A | R²¹ | ¹H-NMR (DMSO d-6) |
|---|---|---|---|
| A-23 | 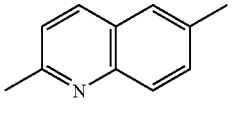 | $CH_3$ | 11.40(s, 1H), 8.70(d, 1H, J=2.0 Hz), 8.54(d, 1H, J=8.5 Hz), 8.45 (d, 1H, J=8.5 Hz), 8.43(dd, 1H, J=8.5, 2.0 Hz), 8.29(d, 1H, J=8.5 Hz), 8.05(d, 1H, J=2.0 Hz), 7.73 (dd, 1H, J=8.5, 2.0 Hz), 7.51(d, 1H, J=8.5 Hz), 7.28(s, 1H), 4.04 (s, 3H) (CDCl₃) |

Example 2

By using a various aminothiazoles instead of a compound (2), compounds (B-1) to (B-32) were synthesized in a manner similar to Example 1. Their physical data were shown in Tables 5, 6, 7, 8, and 9.

TABLE 5

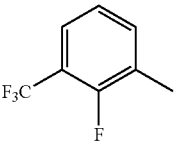

| Compound No. | R¹ | R² | ¹H-NMR (DMSO d-6) |
|---|---|---|---|
| B-1 | 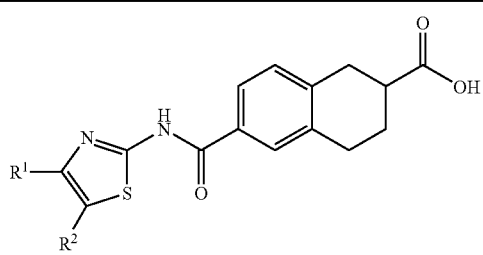 | H | 12.70(bs, 2H), 8.37–8.42(m, 1H), 7.74–7.91(m, 4H), 7.52–7.57(m, 1H), 7.29(d, 1H, J=7.7 Hz), 2.87–3.08(m, 4H), 2.69–2.77(m, 1H), 2.11–2.16(m, 1H), 1.79–1.99(m, 1H) |

TABLE 5-continued

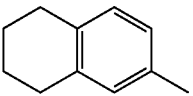

| Compound No. | R¹ | R² | ¹H-NMR (DMSO d-6) |
|---|---|---|---|
| B-2 | 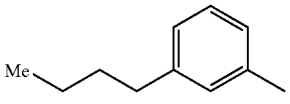 | H | 12.57(bs, 1H), 7.83–7.90(m, 2H), 7.63–7.66(m, 2H), 7.56(s, 1H), 7.28(d, 1H, J=7.9 Hz), 7.11(d, 1H, J=7.9 Hz), 2.68–3.07(m, 9H), 2.10–2.16(m, 1H), 1.75–1.82(m, 5H) |
| B-3 | 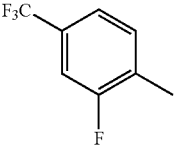 | H | 12.56(bs, 2H), 7.74–7.91(m, 4H), 7.65(s, 1H), 7.34(t, 1H, J=7.6 Hz), 7.28(d, 1H, J=8.2 Hz), 7.15(d, 1H, J=7.3 Hz), 2.86–3.06(m, 4H), 2.61–2.77(m, 3H), 2.12–2.16(m, 1H), 1.73–1.86(m, 1H), 1.55–1.65(m, 2H), 1.29–1.40(m, 2H), 0.92(t, 3H, J=7.3 Hz) |
| B-4 | 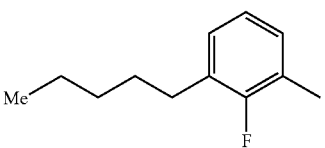 | H | 12.73(bs, 1H), 12.40(bs, 1H), 8.34(t, 1H, J=8.2 Hz), 7.72–7.91(m, 5H), 7.29(d, 1H, J=7.3 Hz), 2.86–3.08(m, 4H), 2.69–2.77(m, 1H), 2.11(m, 1H), 1.73–1.86(m, 1H) |
| B-5 | 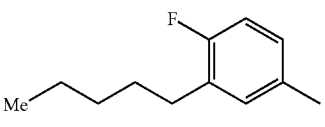 | H | 12.66(bs, 1H), 12.37(bs, 1H), 7.84–7.97(m, 3H), 7.57(d, 1H, J=2.4 Hz), 7.19–7.30(m, 3H), 2.86–3.08(m, 4H), 2.65–2.78(m, 3H), 2.11–2.16(m, 1H), 1.72–1.82(m, 1H), 1.30–1.34(m, 4H), 0.85–0.90(m, 3H) |
| B-6 | 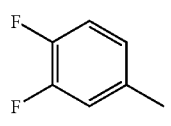 | H | 12.60(bs, 2H), 7.64–7.90(m, 4H), 7.64(s, 1H), 7.28(d, 1H, J=8.2 Hz), 7.20(dd, 1H, J=9.4 Hz, 0.9 Hz), 2.88–3.06(m, 4H), 2.62–2.78(m, 3H), 2.12–2.16(m, 1H), 1.73–1.86(m, 1H), 1.56–1.63(m, 2H), 1.30–1.34(m, 4H), 0.85–0.90(m, 3H) |
| B-7 | 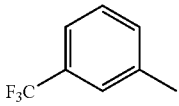 | H | 12.70(s, 1H), 12.35(bs, 1H), 7.97(m, 1H), 7.89(s, 1H), 7.84(dd, 1H, J=8.0, 1.8 Hz), 7.82(m, 1H), 7.79(s, 1H), 7.53(m, 1H), 7.29(d, 1H, J=8.0 Hz), 2.60–3.10(m, 5H), 2.10(m, 1H), 1.90(m, 1H) |

TABLE 6

| Compound No. | R¹ | R² | ¹H-NMR (DMSO d-6) |
|---|---|---|---|
| B-8 | 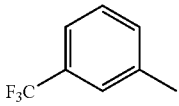 | H | 12.67(s, 1H), 12.36(bs, 1H). 8.32(s, 1H), 8.25(m, 1H), 7.94(s, 1H), 7.91(s, 1H), 7.85(dd, 1H, J=7.9, 1.8 Hz), 7.70(d, 2H, J=5.2 Hz), 7.29(d, 1H, J=7.9 Hz), 2.60–3.10(m, 5H), 2.10(m, 1H), 1.80(m, 1H) |

TABLE 6-continued

| Compound No. | R¹ | R² | ¹H-NMR (DMSO d-6) |
|---|---|---|---|
| B-9 | 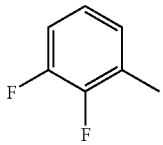 | H | 12.72(s, 1H), 12.38(bs, 1H), 7.80–7.95(m, 3H), 7.68(m, 1H), 7.20–7.50(m, 3H), 2.60–3.10(m, 5H), 2.10(m, 1H), 1.80(m, 1H) |
| B-10 | 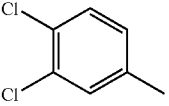 | F | 12.90(bs, 2/3H), 12.70(bs, 1/3H), 12.40(bs, 1H), 8.22(d, 1/3H, J=2.1 Hz), 8.15(d, 2/3H, J=2.1 Hz), 7.70–8.05(m, 4H), 7.29(d, 1H, J=7.9 Hz), 2.60–3.10(m, 5H), 2.10(m, 1H), 1.90(m, 1H) |
| B11 | 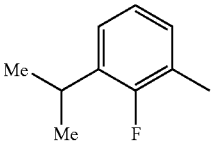 | H | 12.68(bs, 1H), 12.38(bs, 1H), 7.82–8.00(m, 3H), 7.58(d, 1H, J=2.4 Hz), 7.22–7.38(m, 3H), 3.30(m, 1H), 2.65–3.10(m, 5H), 2.17(m, 1H), 1.80(m, 1H), 1.26(d, 6H, J=7.0 Hz) |
| B12 | 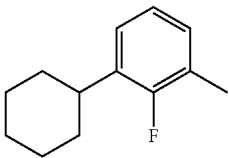 | H | 12.69(s, 1H), 12.39(bs, 1H), 7.82–8.00(m, 3H), 7.58(d, 1H, J=2.4 Hz), 7.20–7.36(m, 3H), 2.60–3.10(m, 6H), 2.15(m, 1H), 1.20–1.90(m, 11H) |
| B13 | 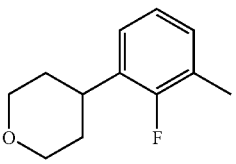 | H | 12.60(bs, 2H), 7.97(dt, 1H, J=1.8, 7.6 Hz), 7.91(s, 1H), 7.86(d, 1H, J=8.2 Hz), 7.58(d, 1H, J=2.4 Hz), 7.22–7.40(m, 3H), 3.97(dd, 2H, J=2.7, 10.7 Hz), 2.65–3.60(m, 8H), 2.15(m, 1H), 1.65–1.85(m, 5H) |
| B-14 | 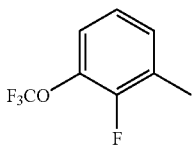 | H | 12.76(brs. 1H), 12.37(brs, 1H), 8.10–8.15(m, 1H), 7.91(brs, 1H), 7.85–7.88(m, 1H), 7.72(d, 1H, J=2.7 Hz), 7.55–7.60(m, 1H), 7.42–7.47(m, 1H), 7.29(d, 1H, J=7.9 Hz), 2.86–3.08(m, 1H), 2.67–2.78(m, 1H), 2.10–2.15(m, 1H), 1.72–1.91(m, 1H) |
| B-15 | 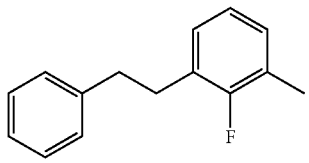 | H | 12.76(s. 1H), 12.37(s, 1H), 7.95(dt, 1H, J=5.6 Hz, 1.9 Hz), 7.90(brs, 1H), 7.84–7.88(m, 1H), 7.57(d, 1H, J=2.5 Hz), 7.16–7.32(m, 8H), 2.86–3.01(m, 8H), 2.68–2.78(m, 1H), 2.10–2.18(m, 1H), 1.73–1.85(m, 1H) |

TABLE 7

| Compound No. | R¹ | R² | ¹H-NMR (DMSO d-6) |
|---|---|---|---|
| B-16 | 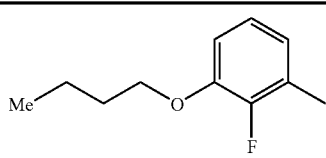 | H | 12.69(bs. 1H), 12.38(bs, 1H), 7.85–7.90(m, 2H), 7.61–7.66(m, 1H), 7.58(d, 1H, J=2.5 Hz), 7.28(d, 1H, J=8.3 Hz), 7.12–7.23(m, 1H), 4.08(t, 2H, J=6.4 Hz), 2.87–3.05(m, 1H), 2.70–2.75(m, 1H), 2.10–2.15(m, 1H), 1.72–1.85(m, 3H), 1.41–1.53(m, 2H), 0.96(t, 3H, J=7.4 Hz) |

TABLE 7-continued

| Compound No. | R¹ | R² | ¹H-NMR (DMSO d-6) |
|---|---|---|---|
| B-17 | 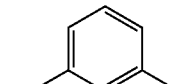 | CH₃ | 12.49(bs. 1H), 8.05(s, 1H), 7.97–8.01(m, 1H), 7.88(s, 1H), 7.82–7.86(m, 1H), 7.68–7.73(m, 2H), 7.27(d, 1H, J=8.1 Hz), 2.85–3.06(m, 4H), 2.67–2.76(m, 1H), 2.55(s, 3H), 2.10–2.15(m, 1H), 1.71–1.84(m, 1H) |
| B-18 | 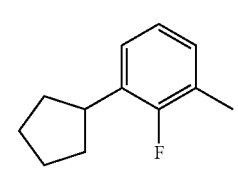 | H | 12.68(s, 1H), 12.38(bs, 1H), 7.83–7.98(m, 3H), 7.57(d, 1H, J=2.7 Hz), 7.20–7.38(m, 3H), 3.20–3.42(m, 2H), 2.65–3.10(m, 5H), 1.55–2.20(m, 9H) |
| B-19 | 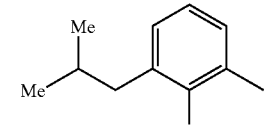 | H | 12.68(s, 1H), 12.38(bs, 1H), 7.96(m, 1H), 7.90(s, 1H), 7.85(d, 1H, J=8.2 Hz), 7.57(d, 1H, J=2.7 Hz), 7.20–7.52(m, 3H), 2.60–3.10(m, 5H), 2.57(d, 2H, J=6.4 Hz), 1.70–2.20(m, 3H), 0.91(d, 6H, J=6.7 Hz) |
| B-20 | 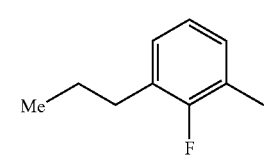 | H | 12.67(bs, 1H), 12.39(bs, 1H), 7.85–7.99(m, 3H), 7.58(d, 1H, J=3.0 Hz), 7.20–7.30(m, 3H), 2.86–3.08(m, 4H), 2.64–2.78(3H, m), 2.08–2.18(m, 1H), 1.72–1.86(m, 1H), 1.64(sext, 2H, J=7.5 Hz), 0.94(t, 3H, J=7.2 Hz) |
| B-21 | 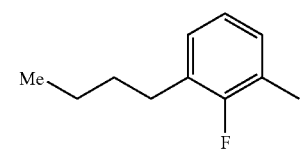 | H | 12.67(bs, 1H), 12.42(bs, 1H), 7.84–7.97(m, 3H), 7.57(d, 1H, J=2.7 Hz), 7.19–7.30(3H, m), 2.85–3.08(m, 4H), 2.66–2.78(m, 3H), 2.08–2.18(m, 1H), 1.72–1.86(m, 1H), 1.59(quint, 2H, J=7.2 Hz), 1.35(sext, 2H, J=7.5 Hz), 0.92(t, 3H, J=7.2 Hz) |
| B-22 | 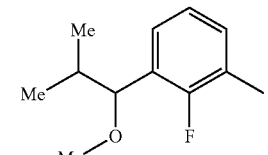 | H | 12.70(s, 1H), 12.40(bs, 1H), 8.05(m, 1H), 7.91(s, 1H), 7.85(d, 1H, J=9.2 Hz), 7.59(d, 1H, J=2.1 Hz), 7.25–7.60(m, 3H), 4.29(d, 1H, J=6.7 Hz), 3.16(s, 3H), 2.60–3.10(m, 5H), 1.70–2.20(m, 3H), 0.96(d, 3H, J=6.5 Hz), 0.80(d, 3H, J=6.5 Hz) |

TABLE 8

| Compound No. | R¹ | R² | ¹H-NMR (DMSO d-6) |
|---|---|---|---|
| B-23 | 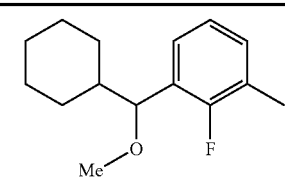 | H | 12.68(s, 1H), 12.39(bs, 1H), 8.04(m, 1H), 7.91(s, 1H), 7.86(d, 1H, J=7.9 Hz), 7.58(d, 1H, J=2.4 Hz), 7.26–7.38(m, 3H), 4.32(d, 1H, J=7.0 Hz), 3.15(s, 3H), 2.64–3.15(m, 5H), 0.95–2.20(m, 13H) |
| B-24 | 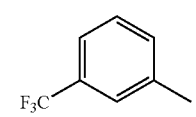 | F | 12.60(bs, 2H), 8.16(s, 1H), 8.13(m, 1H), 7.88(s, 1H), 7.84(dd, 1H, J=1.8, 7.9 Hz), 7.72–7.78(m, 2H), 7.27(d, 1H, J=7.9 Hz), 2.60–3.10(m, 5H), 2.15(m, 1H), 1.80(m, 1H) |

TABLE 8-continued

| Compound No. | R¹ | R² | ¹H-NMR (DMSO d-6) |
|---|---|---|---|
| B-25 | (Me, Me-CH-CH(OEt)-aryl with F, Me substituents) | H | 12.70(s, 1H), 12.40(bs, 1H), 8.03(m, 1H), 7.91(s, 1H), 7.86(d, 1H, J=9.5 Hz), 7.58(d, 1H, J=2.4 Hz), 7.25–7.38 (m, 3H), 4.38(d, 1H, J=7.0 Hz), 3.30 (q, 2H, J=7.0 Hz), 2.62–3.10(m, 5H), 1.70–2.20(m, 3H), 1.11(t, 3H, J=7.0 Hz), 0.96(d, 3H, J=6.7 Hz), 0.80(d, 3H, J=6.7 Hz) |
| B-26 | $C_7H_{15}$-aryl-F,Me | H | 12.66(bs, 1H), 12.37(bs, 1H), 7.84–7.97(m, 3H), 7.57(d, 1H, J=2.5 Hz), 7.17–7.30(m, 3H), 2.87–3.07(m, 4H), 2.65–2.74(m, 3H), 2.10–2.16(m, 1H), 1.74–1.85(m, 1H), 1.50–1.60(m, 2H), 1.26–1.32(m, 8H), 1.02–1.05(m, 3H) |
| B-27 | $C_8H_{17}$-aryl-F,Me | H | 12.67(bs, 1H), 12.40(bs, 1H), 7.84–7.97(m, 3H), 7.57(d, 1H, J=2.5 Hz), 7.18–7.30(m, 3H), 2.86–3.05(m, 4H), 2.64–2.78(m, 3H), 2.11–2.16(m, 1H), 1.74–1.82(m, 1H), 1.54–1.64(m, 2H), 1.24–1.30(m, 10H), 0.83–0.87(m, 3H) |
| B-28 | $C_{10}H_{21}$-aryl-F,Me | H | 12.67(bs. 1H), 7.84–7.98(m, 3H), 7.57 (d, 1H, J=2.5 Hz), 7.19–7.30(m, 3H), 2.85–3.07(m, 4H), 2.64–2.78(m, 3H), 2.11–2.16(m, 1H), 1.72–1.85(m, 1H), 1.57–1.59(m, 2H), 1.23–1.30(m, 14H), 0.82–0.86(m, 3H) |
| B-29 | Br, Me-propyl-aryl-F,Me | H | 12.70(bs, 1H), 12.38(bs, 1H), 7.84–7.93 (m, 3H), 7.62(d, 1H, J=2.7Hz), 7.58 (d, 1H, J=8.4Hz), 7.28(d, 1H, J=8.4 Hz), 2.68–3.07(m, 7H), 2.08–2.18 (m, 1H), 1.72–1.85(m, 1H), 1.60(sext, 2H, J=7.2 Hz), 0.98(t, 3H, J=7.2 Hz) |

TABLE 9

| Compound No. | R¹ | R² | ¹H-NMR (DMSO d-6) |
|---|---|---|---|
| B-30 | Me-CH₂-O-CH₂-CH₂-aryl-F,Me | H | 12.68(bs, 1H), 12.38(bs, 1H), 7.83–8.00(m, 3H), 7.57(d, 1H, J=2.7 Hz), 7.20–7.34(m, 3H), 3.62(t, 2H, J=6.9 Hz), 3.45(q, 2H, J=6.9 Hz), 2.87–3.07(m, 6H), 2.68–2.78(m, 1H), 2.08–2.18(m, 1H), 1.72–1.86(m, 1H), 1.10(t, 3H, J=7.2 Hz) |
| B-31 | phenyl-CH₂-aryl-F,Me | H | 12.67(bs, 1H), 12.38(1H, bs), 7.98 (dt, 1H, J=2.1, 7.2 Hz), 7.84–7.92 (m, 2H), 7.57(d, 1H, J=2.7 Hz), 7.16–7.34(m, 8H), 4.06(s, 2H), 2.85–3.07(m, 4H), 2.67–2.78(m, 1H), 2.08–2.18(m, 1H), 1.71–1.85(m, 1H) |
| B-32 | Me-CH₂-O-C(Me)(Me)-aryl-F,Me | H | 12.68(s, 1H), 12.37(bs, 1H), 8.02 (m, 1H), 7.91(s, 1H), 7.86(d, 1H, J=8.5 Hz), 7.58(s, 1H), 7.41(m, 1H), 7.24–7.34(m, 2H), 3.20–3.40(m, 2H), 2.60–3.10(m, 5H), 2.15(m, 1H), 1.80 (m, 1H), 1.58(s, 6H), 1.14(t, 3H, J=6.7 Hz) |

Example 3

Preparation of Compound (C-1)

(Step 1)

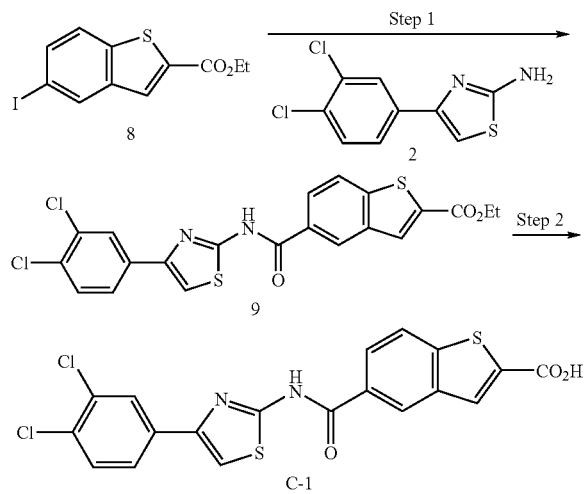

Compound (2) (166 mg) synthesized by Example 1-Step 1, 2-ethoxycarbonyl-5-iodobenzothiophen (8) (150 mg), triethylamine (137 mg), and bis(triphenylphosphine)-palladium (II) dichloride (16 mg) were dissolved in DMF (3 mL), and the reaction mixture was heated with stirring at 90° C. for 1 h. To the reaction mixture was added a aqueous potassium hydrogen sulfate solution and the mixture was extracted with ethyl acetate. The organic layer was washed with brine, dried over magnesium sulfate, and evaporated under reduced pressure. The obtained residue was purified by silica gel column chromatography to give a compound (9) (247 mg).

$^1$H NMR (CDCl$_3$, δ ppm) 10.36 (bs, 1H), 8.41 (s, 1H), 8.09 (s, 1H), 7.95 (s, 2H), 7.84 (d, 1H, J=2.1 Hz), 7.58 (dd, 1H, J=8.5 Hz, 2.1 Hz), 7.34 (d, 1H, J=8.5 Hz), 7.22 (s, 1H), 4.45 (q, 2H, J=7.1 Hz), 1.45 (t, 3H, J=7.1 Hz).

(Step 2)

Compound (9) (217 mg) was dissolved in methanol (5 mL) and dioxane (3 mL), and to the reaction mixture was added a 5 mol/L aqueous sodium hydroxide solution (0.4 mL). The reaction mixture was stirred at room temperature for 4 h, after adjusted to be acidic by addition of diluted hydrochloric acid, and extracted with THF. The organic layer was washed with brine, dried over magnesium sulfate, and evaporated under reduced pressure. The obtained residue was recrystallized from DMF to give a compound (C-1) (105 mg).

$^1$H NMR (DMSO-d$_6$, δ ppm) 13.69 (br, 1H), 12.94 (s, 1H), 8.81 (s, 1H), 8.21–8.26 (m, 3H), 8.19 (dd, 1H, J=8.6 Hz, 1.7 Hz) 7.96 (dd, 1H, J=8.5 Hz, 2.1 Hz), 7.94 (s, 1H), 7.73 (d, 1H, J=8.5 Hz).

By using a various bicyclic heterocycliccarboxylic acid ester halogenated compounds instead of 2-ethoxycarbonyl-5-iodobenzothiophen (8), compounds (C-2) to (C-8) were synthesized in a manner similar to Example 3. Their physical data were shown in Table 10.

TABLE 10

| Compound No. | A | $^1$H-NMR (DMSO d-6) |
|---|---|---|
| C-2 | 6-methylbenzothiophen-2-yl | 12.95(s, 1H), 8.86(s, 1H), 8.23(d, 1H, J=1.8 Hz), 8.21(s, 1H), 8.12–8.19(m, 2H), 7.97(dd, 1H, J=8.2 Hz, 1.8 Hz), 7.96(s, 1H), 7.74(d, 1H, J=8.2 Hz) |
| C-3 | 5-methylbenzofuran-2-yl | 12.88(bs, 1H), 8.62(d, 1H, J=1.8 Hz), 8.23 (dd, 1H, J=7.5 Hz, 1.8 Hz), 8.22(s, 1H), 7.95(dd, 1H, J=8.7 Hz, 2.4 Hz), 7.86(d, 1H, J=9.0 Hz), 7.92(s, 1H), 7.74(s, 1H), 7.72(d, 1H, J=8.4 Hz) |
| C-4 | 6-methylbenzofuran-2-yl | 12.92(s, 1H), 8.49(s, 1H), 8.21(s, 1H), 8.08 (d, 1H, J=8.4 Hz), 7.95(s, 1H), 7.92(bs, 2H), 7.76(s, 1H), 7.71(d, 1H, J=8.4 Hz) |
| C-5 | 5-methyl-3-methylbenzofuran-2-yl | 12.87(bs, 1H), 8.73(s, 1H), 8.23(dd, 1H, J=9.0 Hz, 1.8 Hz), 8.23(s, 1H), 7.95(dd, 1H, J=8.4 Hz, 1.8 Hz), 7.92(s, 1H), 7.81(d, 1H, J=9.0 Hz), 7.72(d, 1H, J=8.4 Hz), 2.62(s, 3H) |

TABLE 10-continued

[Structure: 3,4-dichlorophenyl-thiazole-NH-C(O)-A-C(O)OH]

| Compound No. | A | ¹H-NMR (DMSO d-6) |
|---|---|---|
| C-6 | [8-methyl-benzoxepine] | 12.88(bs, 1H), 8.41(s, 1H), 8.21(d, 1H, J=1.8 Hz), 8.05(dd, 1H, J=8.4, 1.5 Hz), 7.95(dd, 1H, J=8.4, 2.1 Hz), 7.93(s, 1H), 7.86(d, 1H, J=8.1Hz), 7.72(d, 1H, J=8.4 Hz), 7.63(d, 1H, J=15.9 Hz), 7.47(s, 1H), 6.54(d, 1H, J=15.9 Hz) |
| C-7 | [7-methyl-benzoxepine] | 12.83(s, 1H), 8.54(d, 1H, J=1.5 Hz), 8.22 (d, 1H, J=2.1 Hz), 8.17(dd, 1H, J=8.7, 1.8 Hz), 7.95(dd, 1H, J=8.4, 2.1 Hz), 7.92(s, 1H), 7.79(d, 1H, J=8.7 Hz), 7.73(d, 1H, J=8.7 Hz), 7.62(d, 1H, J=15.9 Hz), 7.52(s, 1H), 6.49(d, 1H, J=16.2 Hz) |
| C-8 | [7-methyl-tetrahydro-benzoxepine] | 12.64(bs, 1H), 12.23(brs, 1H), 8.21(d, 1H, J=2.4 Hz), 7.94(dd, 1H, J=8.1, 1.8 Hz), 7.90(s, 1H), 7.72(d, 1H, J=8.4 Hz), 7.63 (dd, 1H, J=7.5, 1.2 Hz), 7.46(s, 1H), 7.36 (d, 1H, J=7.8 Hz), 4.89(m, 1H), 3.39(m, 1H), 2.95(dd, 1H, J=16.2, 7.2 Hz), 2.41(t, 2H, J=7.2 Hz), 1.95(m, 2H) |

Example 4

Preparation of Compound (D-1)

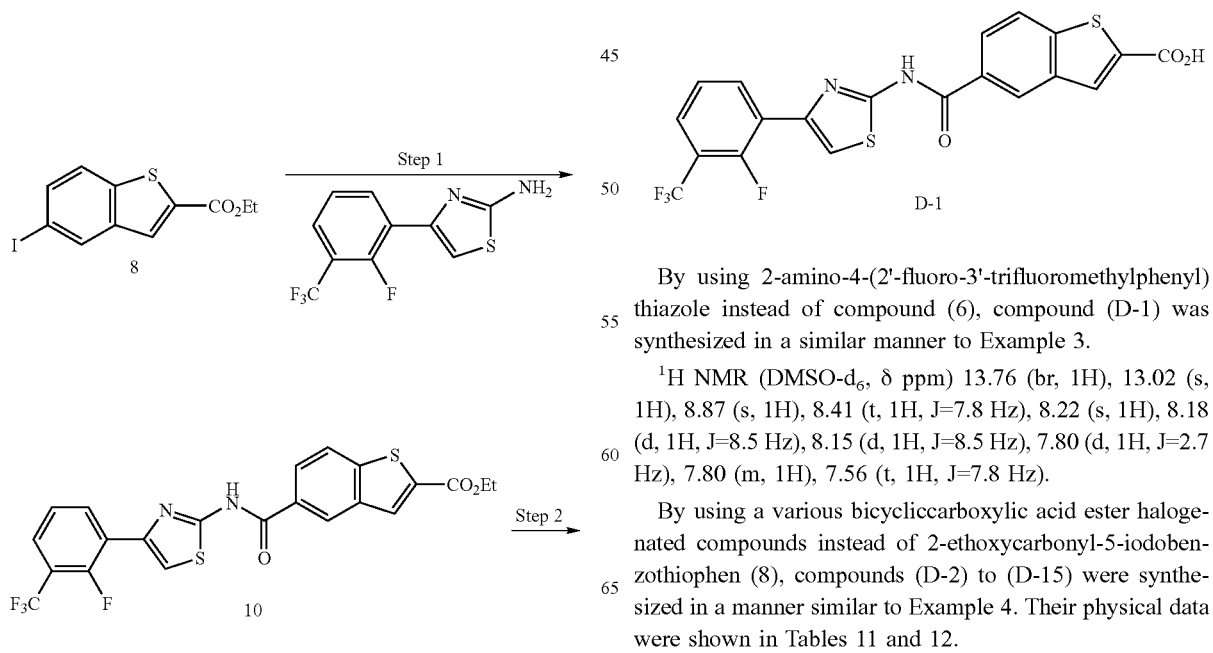

By using 2-amino-4-(2'-fluoro-3'-trifluoromethylphenyl) thiazole instead of compound (6), compound (D-1) was synthesized in a similar manner to Example 3.

¹H NMR (DMSO-$d_6$, δ ppm) 13.76 (br, 1H), 13.02 (s, 1H), 8.87 (s, 1H), 8.41 (t, 1H, J=7.8 Hz), 8.22 (s, 1H), 8.18 (d, 1H, J=8.5 Hz), 8.15 (d, 1H, J=8.5 Hz), 7.80 (d, 1H, J=2.7 Hz), 7.80 (m, 1H), 7.56 (t, 1H, J=7.8 Hz).

By using a various bicycliccarboxylic acid ester halogenated compounds instead of 2-ethoxycarbonyl-5-iodobenzothiophen (8), compounds (D-2) to (D-15) were synthesized in a manner similar to Example 4. Their physical data were shown in Tables 11 and 12.

TABLE 11

| Compound No. | A | R⁷ | R²¹ | ¹H-NMR (DMSO d-6) |
|---|---|---|---|---|
| D-2 | naphthalene-2,6-diyl | $CF_3$ | H | 13.31(bs, 1H), 13.13(s, 1H), 8.89(s, 1H), 8.71(s, 1H), 8.20–8.46(m, 5H), 7.69–7.92 (m, 2H), 7.57(t, 1H, J=7.9 Hz) |
| D-3 | 2,3-dihydro-1H-indene-2,5-diyl | $CF_3$ | H | 12.78(s, 1H), 12.42(bs, 1H), 8.40(t, 1H, J=7.5 Hz), 8.00(s, 1H), 7.94(d, 1H, J=7.9 Hz), 7.79(m, 1H), 7.76(d, 1H, J=2.7 Hz), 7.55(t, 1H, J=7.9 Hz), 7.39(d, 1H, J=7.9 Hz), 3.10–3.40(m, 5H) |
| D-4 | 1H-indene-2,5-diyl | $CF_3$ | Et | 10.01(bs, 1H), 8.23(t, 1H, J=7.5 Hz), 8.06(s, 1H), 7.90(d, 1H, J=7.9 Hz), 7.74(s, 1H), 7.62(d, 1H, J=7.9 Hz), 7.56(d, 1H, J=2.4 Hz), 7.51(d, 1H, J=7.3 Hz), 7.29(d, 1H, J=7.6 Hz), 4.34(q, 2H, J=7.0 Hz), 3.77(s, 2H), 1.39(t, 3H, J=7.0 Hz) |
| D-5 | 1H-indene-2,5-diyl | $CF_3$ | H | 12.91(s, 1H), 12.73(bs, 1H), 8.28–8.46(m, 2H), 8.13(t, 1H, J=7.3 Hz), 7.66–7.88(m, 4H), 7.56(t, 1H, J=7.9 Hz), 3.77(s, 2H) |
| D-6 | 1-oxo-2,3-dihydro-1H-indene-2,5-diyl | $CF_3$ | Et | 13.14(s, 1/7H), 12.96(s, 6/7H), 10.96(s, 1H), 8.40(t, 1H, J=7.0 Hz), 8.34(s, 1/7H), 8.28(s, 6/7H), 8.18(d, 6/7H, J=7.9 Hz), 8.12(d, 1/7H, J=7.9 Hz), 7.74–7.86(m, 3H), 7.56(t, 1H, J=7.6 Hz), 4.26(q, 12/7H, J=7.0 Hz), 4.16(q, 2/7H, J=7.0 Hz), 3.63(s, 2/7H), 3.40(s, 2/7H), 1.30(t, 18/7H, J=7.0 Hz), 1.22(t, 3/7H, J=7.0 Hz) (6:1 tautomer mixture) |
| D-7 | 1,2,3,4-tetrahydronaphthalene-2,6-diyl | $CF_3$ | H | 12.86(s, 1H), 12.67(bs, 1H), 8.40(t, 1H, J=7.8 Hz), 7.96–8.05(m, 2H), 7.79(t, 1H, J=6.7 Hz), 7.77(d, 1H, J=2.1 Hz), 7.48–7.60(m, 3H), 2.93(t, 2H, J=8.2 Hz), 2.55(t, 2H, J=8.2 Hz) |
| D-8 | 2-oxo-2H-chromene-3,7-diyl | $CF_3$ | Me | 13.14(bs, 1H), 8.85(s, 1H), 8.40(t, 1H, J=6.7 Hz), 8.13(s, 1H), 8.08(s, 2H), 7.75–7.84(m, 2H), 7.56(t, 1H, J=7.6 Hz), 3.86(s, 3H) |
| D-9 | 5,6,7,8-tetrahydronaphthalene-2,6-diyl | $CF_3$ | H | 12.99(bs, 1H), 12.59(s, 1H), 8.39(t, 1H, J=7.0 Hz), 7.70–7.88(m, 5H), 7.55(t, 1H, J=7.6 Hz), 7.42(d, 1H, J=7.6 Hz), 2.94(t, 2H, J=8.2 Hz), 2.67(t, 2H, J=8.2 Hz) |

TABLE 12

| Compound No. | A | R⁷ | R²¹ | ¹H-NMR (DMSO d-6) |
|---|---|---|---|---|
| D-10 | 1,2,3,4-tetrahydronaphthalene-2,6-diyl | 1-cyclohexyl-1-methoxymethyl | H | 12.79(bs, 2H), 7.96–8.08(m, 3H), 7.60(d, 1H, J=2.4 Hz), 7.55(s, 1H), 7.50(d, 1H, J=7.9 Hz), 7.26–7.38(m, 2H), 4.32(d, 1H, J=7.0 Hz), 3.15(s, 3H), 2.92(t, 2H, J=8.2 Hz), 2.55(t, 2H, J=8.2 Hz), 1.00–1.99(m, 11H) |

TABLE 12-continued

| Compound No. | A | $R^7$ | $R^{21}$ | $^1$H-NMR (DMSO d-6) |
|---|---|---|---|---|
| D-11 | 6-methyl-1,2,3,4-tetrahydronaphthalen-2-yl | $^t$BuCH$_2$—CH$_2$— | H | 12.78(s, 1H), 12.69(bs, 1H), 7.90–8.04(m, 3H), 7.60(d, 1H, J=2.7 Hz), 7.55(s, 1H), 7.50(d, 1H, J=7.9 Hz), 7.26(m, 1H), 7.22(t, 1H, J=7.5 Hz), 2.92(t, 2H, J=8.2 Hz), 2.60–2.68(m, 2H), 2.55(t, 2H, J=8.2 Hz), 1.43–1.52(m, 2H), 0.98(s, 9H) |
| D-12 | 6-methyl-1,2,3,4-tetrahydronaphthalen-2-yl | n-Pentyl | H | 12.80(bs, 2H), 7.90–8.04(m, 3H), 7.58(d, 1H, J=2.4 Hz), 7.51(s, 1H), 7.48(d, 1H, J=7.9 Hz), 7.19–7.31(m, 2H), 2.91(t, 2H, J=8.2 Hz), 2.68(t, 2H, J=8.2 Hz), 2.54(t, 2H, J=8.2 Hz), 1.58–1.64(m, 2H), 1.28–1.40(m, 4H), 0.88(t, 3H, J=6.7 Hz) |
| D-13 | 6-methyl-1,2,3,4-tetrahydronaphthalen-2-yl | iso-Pentyl | H | 12.80(bs, 2H), 7.90–8.06(m, 3H), 7.56(s, 1H), 7.47–7.56(m, 2H), 7.18–7.34(m, 2H), 2.92(t, 2H, J=8.2 Hz), 2.67(t, 2H, J=7.2 Hz), 2.55(t, 2H, J=8.2 Hz), 1.49–1.68(m, 3H), 1.19–1.35(m, 2H), 0.87(d, 6H, J=6.7 Hz) |
| D-14 | 6-methyl-1,2,3,4-tetrahydronaphthalen-2-yl | cyclo-hexyl | H | 12.77(s, 1H), 12.68(bs, 1H), 7.90–8.04(m, 3H), 7.59(d, 1H, J=2.4 Hz), 7.55(s, 1H), 7.50(d, 1H, J=7.9 Hz), 7.20–7.36(m, 2H), 2.82–2.99(m, 3H), 2.55(t, 2H, J=8.5 Hz), 1.20–1.90(m, 10H) |
| D-15 | 6-methyl-1,2,3,4-tetrahydronaphthalen-2-yl | n-Heptyl | H | 12.77(bs, 2H), 7.90–8.04(m, 3H), 7.59(d, 1H, J=2.1 Hz), 7.55(s, 1H), 7.51(d, 1H, J=7.6 Hz), 7.18–7.30(m, 2H), 2.92(t, 2H, J=8.2 Hz), 2.68(t, 2H, J=7.3 Hz), 2.55(t, 2H, J=8.2 Hz), 1.50–1.70(m, 2H), 1.20–1.40(m, 8H), 0.86(t, 3H, J=6.3 Hz) |

Example 5

Preparation of Compound (E-1)

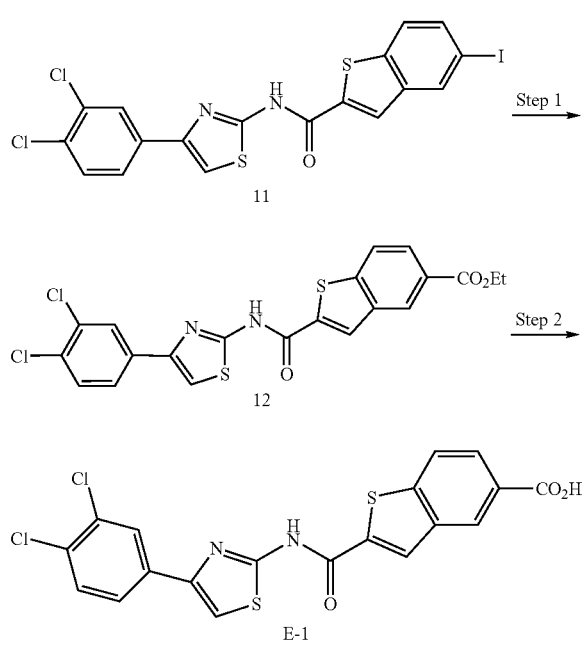

(Step 1)

Compound (11) (169 mg), triethylamine (96 mg), and bis(triphenylphosphine)palladium (II) chloride (11 mg) were dissolved in DMF (3 mL) and ethanol (0.5 mL), and the reaction mixture was heated with stirring at 90° C. for 4 h under carbon monooxide atmosphere. To the reaction mixture was added a aqueous potassium hydrogen sulfate and the mixture was extracted with ethyl acetate. The organic layer was washed with brine, dried over magnesium sulfate, and evaporated under reduced pressure. The obtained residue was purified by silica gel column chromatography to give a compound (12) (63 mg).

$^1$H NMR (CDCl$_3$, δ ppm) 10.00 (bs, 1H), 8.61 (1H, d, J=1.5 Hz), 8.16 (dd, 1H, J=8.5 Hz, 1.5 Hz), 8.06 (s, 1H), 7.96 (d, 1H, J=8.5 Hz), 7.92 (d, 1H, J=2.1 Hz), 7.63 (dd, 1H, J=8.5 Hz, 2.1 Hz), 7.45 (d, 1H, J=8.5 Hz), 7.25 (s, 1H), 4.46 (q, 2H, J=7.1 Hz), 1.46 (t, 3H, J=7.1 Hz).

(Step 2)

Compound (12) (40 mg) was dissolved in methanol (1 mL) and tetrahydrofuran (1 mL), and to the reaction mixture was added a aqueous 5 mol/L sodium hydroxide solution (0.2 mL). The reaction mixture was stirred at room temperature for 2 h, after adjusted to be acidic by a addition of diluted hydrochloric acid, extracted with THF and ethyl acetate. The organic layer was washed with brine, dried over magnesium sulfate, and evaporated under reduced pressure. The obtained residue was recrystallized from DMF to give a compound (E-1) (35 mg).

$^1$H NMR (DMSO-d$_6$, δ ppm) 13.31 (br, 1H), 13.22 (s, 1H), 8.74 (s, 1H), 8.59 (d, 1H, J=1.5 Hz), 8.23 (d, 1H, J=8.5

Hz), 8.23 (d, 1H, J=2.1 Hz), 8.04 (dd, 1H, J=8.5 Hz, 1.5 Hz), 7.97 (s, 1H), 7.96 (dd, 1H, J=8.5 Hz, 2.1 Hz), 7.74 (d, 1H, J=8.5 Hz).

By using a various bicyclic heterocyclic halogenated compounds instead of compound (11), compounds (E-2) and (E-3) were synthesized in a manner similar to Example 5. Their physical data were shown in Table 13.

TABLE 13

| Compound No. | A | $^1$H-NMR (DMSO d-6) |
|---|---|---|
| E-2 | ![structure] | 13.29(bs, 2H), 8.73(s, 1H), 8.70 (s, 1H), 8.23(d, 1H, J=1.8 Hz), 8.12(d, 1H, J=8.2 Hz), 8.01(dd, 1H, J=8.2 Hz, 1.8 Hz), 7.99(dd, 1H, J=8.2, 1.8 Hz), 7.96(d, 1H, J=1.8 Hz), 7.74(d, 1H, J=8.2 Hz) |
| E-3 | ![structure] | 13.15(bs, 1H), 12.89(s, 1H), 8.43 (s, 1H), 8.22(d, 1H, J=1.8 Hz), 8.14(d, 1H, J=8.7 Hz), 7.96 (s, 1H), 7.95(dd, 1H, J=8.1 Hz, 1.8 Hz), 7.75(d, 1H, J=8.7 Hz), 7.73(d, 1H, J=8.1 Hz), 2.67(s, 3H) |

All compounds of the general formula (XIII) to (XVII), having substituent of the following combination, can be synthesized.

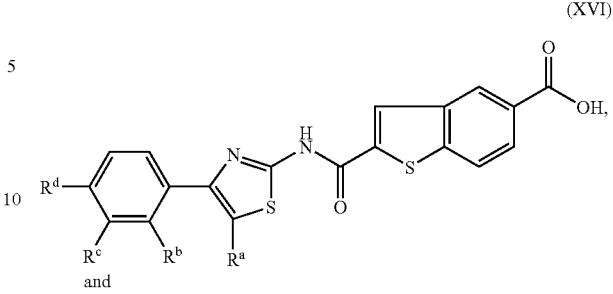

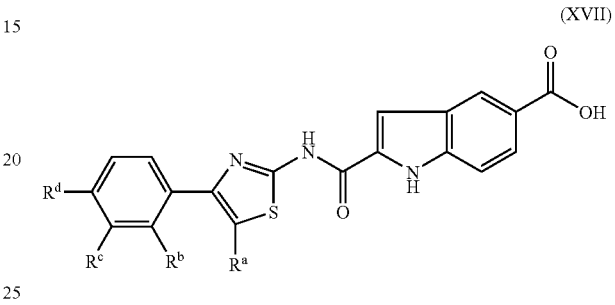

wherein $R^a$ is hydrogen atom, fluoro, or methyl; $R^b$ is hydrogen atom, fluoro, or chloro; $R^c$ is hydrogen atom, fluoro, chloro, methyl, ethyl, n-propyl, cyclopropyl, isopropyl, n-butyl, isobutyl, sec-butyl, n-pentyl, cyclopentyl, n-hexyl, cyclohexyl, hydroxy, methyloxy, ethyloxy, n-propyloxy, phenyloxy, benzyloxy, phenylethyloxy, trifluoromethyl, trifluoromethyloxy, phenyl, 4-fluorophenyl, 4-trifluoromethylphenyl, 4-dimethylaminophenyl, 4-hydroxyphenyl, 3,4-difluorophenyl, 4-carboxyphenyl, benzyl, 4-fluorobenzyl, 2-pyridyl, 3-pyridyl, 4-pyridyl, 2-thienyl, 3-thienyl, pyrazol-2-yl, pyrazol-3-yl, pyrimidin-2-yl, pyrimidin-4-yl, pyrimidin-5-yl, 3-carboxypropyl, 4-carboxybutyl, 4-dimethylaminocarbonylbutyl, 5-dimethylaminocarbonylpentyl, methyloxymethyl, ethyloxymethyl, ethyloxyethyl, methyloxyethyloxyethyl, methyloxyethyl, hydroxymethyl, hydroxyethyl, hydroxypropyl, hydroxybutyl, hydroxypentyl, dimethylamino, piperidin-4-ylmethyl, or cyclohexylmethyl; $R_d$ is hydrogen atom, fluoro, chloro, bromo, methyl, or trifluoromethyl;

($R^a$, $R^b$, $R^c$, $R^d$)=(H, H, H, H), (H, H, H, Cl), (H, H, H, F), (H, H, H, CF$_3$), (H, H, H, Br), (H, H, H, Me), (H, H, F, H), (H, H, F, Cl), (H, H, F, F), (H, H, F, CF$_3$), (H, H, F, Br), (H, H, F, Me), (H, H, Cl, H), (H, H, Cl, Cl), (H, H, Cl, F), (H, H, Cl, CF$_3$), (H, H, Cl, Br), (H, H, Cl, Me), (H, H, Me, H), (H, H, Me, Cl), (H, H, Me, F), (H, H, Me, CF$_3$), (H, H, Me, Br), (H, H, Me, Me), (H, H, Et, H), (H, H, Et, Cl), (H, H, Et, F), (H, H, Et, CF$_3$), (H, H, Et, Br), (H, H, Et, Me), (H, H, n-Pr, H), (H, H, n-Pr, Cl), (H, H, n-Pr, F), (H, H, n-Pr, CF$_3$), (H, H, n-Pr, Br), (H, H, n-Pr, Me), (H, H, c-Pr, H), (H, H, c-Pr, Cl), (H, H, c-Pr, F), (H, H, c-Pr, CF$_3$), (H, H, c-Pr, Br), (H, H, c-Pr, Me), (H, H, i-Pr, H), (H, H, i-Pr, Cl), (H, H, i-Pr, F), (H, H, i-Pr, CF$_3$), (H, H, i-Pr, Br), (H, H, i-Pr, Me), (H, H, n-Bu, H), (H, H, n-Bu, Cl), (H, H, n-Bu, F), (H, H, n-Bu, CF$_3$), (H, H, n-Bu, Br), (H, H, n-Bu, Me), (H, H, i-Bu, H), (H, H, i-Bu, Cl), (H, H, i-Bu, F), (H, H, i-Bu, CF$_3$), (H, H, i-Bu, Br), (H, H, i-Bu, Me), (H, H, sec-Bu, H), (H, H, sec-Bu, Cl), (H, H, sec-Bu, F), (H, H, sec-Bu, CF$_3$), (H, H, sec-Bu, Br), (H, H, sec-Bu, Me), (H, H, n-Pen, H), (H, H, n-Pen, Cl), (H, H, n-Pen, F), (H, H, n-Pen, CF$_3$), (H, H, n-Pen, Br), (H, H, n-Pen, Me), (H, H, c-Pen, H), (H, H, c-Pen, Cl), (H, H, c-Pen, F), (H, H, c-Pen, CF₃), (H, H, c-Pen, Br), (H, H, c-Pen, Me), (H, H, n-Hex, H), (H, H, n-Hex, Cl), (H, H, n-Hex, F), (H, H, n-Hex, CF₃), (H, H, n-Hex, Br), (H, H, n-Hex, Me), (H, H, c-Hex, H), (H, H, c-Hex, Cl), (H, H, c-Hex, F), (H, H, c-Hex, CF₃), (H, H, c-Hex, Br), (H, H, c-Hex, Me), (H, H, OH, H), (H, H, OH, Cl), (H, H, OH, F), (H, H, OH, CF₃), (H, H, OH, Br), (H, H, OH, Me), (H, H, MeO, H), (H, H, MeO, Cl), (H, H, MeO, F), (H, H, MeO, CF₃), (H, H, MeO, Br), (H, H, MeO, Me), (H, H, EtO, H), (H, H, EtO, Cl), (H, H, EtO, F), (H, H, EtO, CF₃), (H, H, EtO, Br), (H, H, EtO, Me), (H, H, n-PrO, H), (H, H, n-PrO, Cl), (H, H, n-PrO, F), (H, H, n-PrO, CF₃), (H, H, n-PrO, Br), (H, H, n-PrO, Me), (H, H, PhO, H), (H, H, PhO, Cl), (H, H, PhO, F), (H, H, PhO, CF₃), (H, H, PhO, Br), (H, H, PhO, Me), (H, H, BnO, H), (H, H, BnO, Cl), (H, H, BnO, F), (H, H, BnO, CF₃), (H, H, BnO, Br), (H, H, BnO, Me), (H, H, PhCH₂CH₂O, H), (H, H, PhCH₂CH₂O, Cl), (H, H, PhCH₂CH₂O, F), (H, H, PhCH₂CH₂O, CF₃), (H, H, PhCH₂CH₂O, Br), (H, H, PhCH₂CH₂O, Me), (H, H, CF₃, H), (H, H, CF₃, Cl), (H, H, CF₃, F), (H, H, CF₃, CF₃), (H, H, CF₃, Br), (H, H, CF₃, Me), (H, H, CF₃O, H), (H, H, CF₃O, Cl), (H, H, CF₃O, F), (H, H, CF₃O, CF₃), (H, H, CF₃O, Br), (H, H, CF₃O, Me), (H, H, Ph, H), (H, H, Ph, Cl), (H, H, Ph, F), (H, H, Ph, CF₃), (H, H, Ph, Br), (H, H, Ph, Me), (H, H, 4-F-Ph, H), (H, H, 4-F-Ph, Cl), (H, H, 4-F-Ph, F), (H, H, 4-F-Ph, CF₃), (H, H, 4-F-Ph, Br), (H, H, 4-F-Ph, Me), (H, H, 4-CF₃-Ph, H), (H, H, 4-CF₃-Ph, Cl), (H, H, 4-CF₃-Ph, F), (H, H, 4-CF₃-Ph, CF₃), (H, H, 4-CF₃-Ph, Br), (H, H, 4-CF₃-Ph, Me), (H, H, 4-(Me)₂N-Ph, H), (H, H, 4-(Me)₂N-Ph, Cl), (H, H, 4-(Me)₂N-Ph, F), (H, H, 4-(Me)₂N-Ph, CF₃), (H, H, 4-(Me)₂N-Ph, Br), (H, H, 4-(Me)₂N-Ph, Me), (H, H, 4-OH-Ph, H), (H, H, 4-OH-Ph, Cl), (H, H, 4-OH-Ph, F), (H, H, 4-OH-Ph, CF₃), (H, H, 4-OH-Ph, Br), (H, H, 4-OH-Ph, Me), (H, H, 3,4-di-F-Ph, H), (H, H, 3,4-di-F-Ph, Cl), (H, H, 3,4-di-F-Ph, F), (H, H, 3,4-di-F-Ph, CF₃), (H, H, 3,4-di-F-Ph, Br), (H, H, 3,4-di-F-Ph, Me), (H, H, 4-COOH-Ph, H), (H, H, 4-COOH-Ph, Cl), (H, H, 4-COOH-Ph, F), (H, H, 4-COOH-Ph, CF₃), (H, H, 4-COOH-Ph, Br), (H, H, 4-COOH-Ph, Me), (H, H, Bn, H), (H, H, Bn, Cl), (H, H, Bn, F), (H, H, Bn, CF₃), (H, H, Bn, Br), (H, H, Bn, Me), (H, H, 4-F-Bn, H), (H, H, 4-F-Bn, Cl), (H, H, 4-F-Bn, F), (H, H, 4-F-Bn, CF₃), (H, H, 4-F-Bn, Br), (H, H, 4-F-Bn, Me), (H, H, 2-Py, H), (H, H, 2-Py, Cl), (H, H, 2-Py, F), (H, H, 2-Py, CF₃), (H, H, 2-Py, Br), (H, H, 2-Py, Me), (H, H, 3-Py, H), (H, H, 3-Py, Cl), (H, H, 3-Py, F), (H, H, 3-Py, CF₃), (H, H, 3-Py, Br), (H, H, 3-Py, Me), (H, H, 4-Py, H), (H, H, 4-Py, Cl), (H, H, 4-Py, F), (H, H, 4-Py, CF₃), (H, H, 4-Py, Br), (H, H, 4-Py, Me), (H, H, 2-Th, H), (H, H, 2-Th, Cl), (H, H, 2-Th, F), (H, H, 2-Th, CF₃), (H, H, 2-Th, Br), (H, H, 2-Th, Me), (H, H, 3-Th, H), (H, H, 3-Th, Cl), (H, H, 3-Th, F), (H, H, 3-Th, CF₃), (H, H, 3-Th, Br), (H, H, 3-Th, Me), (H, H, Pyrazol-2-yl, H), (H, H, Pyrazol-2-yl, Cl), (H, H, Pyrazol-2-yl, F), (H, H, Pyrazol-2-yl, CF₃), (H, H, Pyrazol-2-yl, Br), (H, H, Pyrazol-2-yl, Me), (H, H, Pyrazol-3-yl, H), (H, H, Pyrazol-3-yl, Cl), (H, H, Pyrazol-3-yl, F), (H, H, Pyrazol-3-yl, CF₃), (H, H, Pyrazol-3-yl, Br), (H, H, Pyrazol-3-yl, Me), (H, H, pyrimidin-2-yl, H), (H, H, pyrimidin-2-yl, Cl), (H, H, pyrimidin-2-yl, F), (H, H, pyrimidin-2-yl, CF₃), (H, H, pyrimidin-2-yl, Br), (H, H, pyrimidin-2-yl, Me), (H, H, pyrimidin-4-yl, H), (H, H, pyrimidin-4-yl, Cl), (H, H, pyrimidin-4-yl, F), (H, H, pyrimidin-4-yl, CF₃), (H, H, pyrimidin-4-yl, Br), (H, H, pyrimidin-4-yl, Me), (H, H, pyrimidin-5-yl, H), (H, H, pyrimidin-5-yl, Cl), (H, H, pyrimidin-5-yl, F), (H, H, pyrimidin-5-yl, CF₃), (H, H, pyrimidin-5-yl, Br), (H, H, pyrimidin-5-yl, Me), (H, H, HOOCCH₂CH₂CH₂, H), (H, H, HOOCCH₂CH₂CH₂, Cl), (H, H, HOOCCH₂CH₂CH₂, F), (H, H, HOOCCH₂CH₂CH₂, CF₃), (H, H, HOOCCH₂CH₂CH₂, Br), (H, H, HOOCCH₂CH₂CH₂, Me), (H, H, HOOCCH₂CH₂CH₂CH₂, H), (H, H, HOOCCH₂CH₂CH₂CH₂, Cl), (H, H, HOOCCH₂CH₂CH₂CH₂, F), (H, H, HOOCCH₂CH₂CH₂CH₂, CF₃), (H, H, HOOCCH₂CH₂CH₂CH₂, Br), (H, H, HOOCCH₂CH₂CH₂CH₂, Me), (H, H, (Me)₂NCOCH₂CH₂CH₂, H), (H, H, (Me)₂NCOCH₂CH₂CH₂, Cl), (H, H, (Me)₂NCOCH₂CH₂CH₂, F), (H, H, (Me)₂NCOCH₂CH₂CH₂, CF₃), (H, H, (Me)₂NCOCH₂CH₂CH₂, Br), (H, H, (Me)₂NCOCH₂CH₂CH₂, Me), (H, H, (Me)₂NCOCH₂CH₂CH₂CH₂, H), (H, H, (Me)₂NCOCH₂CH₂CH₂CH₂, Cl), (H, H, (Me)₂NCOCH₂CH₂CH₂CH₂, F), (H, H, (Me)₂NCOCH₂CH₂CH₂CH₂, CF₃), (H, H, (Me)₂NCOCH₂CH₂CH₂CH₂, Br), (H, H, (Me)₂NCOCH₂CH₂CH₂CH₂, Me), (H, H, MeOCH₂, H), (H, H, MeOCH₂, Cl), (H, H, MeOCH₂, F), (H, H, MeOCH₂, CF₃), (H, H, MeOCH₂, Br), (H, H, MeOCH₂, Me), (H, H, EtOCH₂, H), (H, H, EtOCH₂, Cl), (H, H, EtOCH₂, F), (H, H, EtOCH₂, CF₃), (H, H, EtOCH₂, Br), (H, H, EtOCH₂, Me), (H, H, EtOCH₂CH₂, H), (H, H, EtOCH₂CH₂, Cl), (H, H, EtOCH₂CH₂, F), (H, H, EtOCH₂CH₂, CF₃), (H, H, EtOCH₂CH₂, Br), (H, H, EtOCH₂CH₂, Me), (H, H, MeOCH₂CH₂OCH₂CH₂, H), (H, H, MeOCH₂CH₂OCH₂CH₂, Cl), (H, H, MeOCH₂CH₂OCH₂CH₂, F), (H, H, MeOCH₂CH₂OCH₂CH₂, CF₃), (H, H, MeOCH₂CH₂OCH₂CH₂, Br); (H, H, MeOCH₂CH₂OCH₂CH₂, Me), (H, H, MeOCH₂CH₂, H), (H, H, MeOCH₂CH₂, Cl), (H, H, MeOCH₂CH₂, F), (H, H, MeOCH₂CH₂, CF₃), (H, H, MeOCH₂CH₂, Br), (H, H, MeOCH₂CH₂, Me), (H, H, HOCH₂, H), (H, H, HOCH₂, Ci), (H, H, HOCH₂, F), (H, H, HOCH₂, CF₃), (H, H, HOCH₂, Br), (H, H, HOCH₂, Me), (H, H, HOCH₂CH₂, H), (H, H, HOCH₂CH₂, Cl), (H, H, HOCH₂CH₂, F), (H, H, HOCH₂CH₂, CF₃), (H, H, HOCH₂CH₂, Br), (H, H, HOCH₂CH₂, Me), (H, H, HOCH₂CH₂CH₂, H), (H, H, HOCH₂CH₂CH₂, Cl), (H, H, HOCH₂CH₂CH₂, F), (H, H, HOCH₂CH₂CH₂, CF₃), (H, H, HOCH₂CH₂CH₂, Br), (H, H, HOCH₂CH₂CH₂, Me), (H, H, HOCH₂CH₂CH₂CH₂, H), (H, H, HOCH₂CH₂CH₂CH₂, Cl), (H, H, HOCH₂CH₂CH₂CH₂, F), (H, H, HOCH₂CH₂CH₂CH₂, CF₃), (H, H, HOCH₂CH₂CH₂CH₂, Br), (H, H, HOCH₂CH₂CH₂CH₂, Me), (H, H, HOCH₂CH₂CH₂CH₂CH₂, H), (H, H, HOCH₂CH₂CH₂CH₂CH₂, Cl), (H, H, HOCH₂CH₂CH₂CH₂CH₂, F), (H, H, HOCH₂CH₂CH₂CH₂CH₂, CF₃), (H, H, HOCH₂CH₂CH₂CH₂CH₂, Br), (H, H, HOCH₂CH₂CH₂CH₂CH₂, Me), (H, H, HOCH₂CH₂OCH₂CH₂, H), (H, H, HOCH₂CH₂OCH₂CH₂, Cl), (H, H, HOCH₂CH₂OCH₂CH₂, F), (H, H, HOCH₂CH₂OCH₂CH₂, CF₃), (H, H, HOCH₂CH₂OCH₂CH₂, Br), (H, H, HOCH₂CH₂OCH₂CH₂, Me), (H, H, (Me)₂N, H), (H, H, (Me)₂N, Cl), (H, H, (Me)₂N, F), (H, H, (Me)₂N, CF₃), (H, H, (Me)₂N, Br), (H, H, (Me)₂N, Me), (H, H, piperidin-4-yl-methyl, H), (H, H, piperidin-4-yl-methyl, Cl), (H, H, piperidin-4-yl-methyl, F), (H, H, piperidin-4-yl-methyl, CF₃), (H, H, piperidin-4-yl-methyl, Br), (H, H, piperidin-4-yl-methyl, Me), (H, H, cyclohexylmethyl, H), (H, H, cyclohexylmethyl, Cl), (H, H, cyclohexylmethyl, F), (H, H, cyclohexylmethyl, CF₃), (H, H, cyclohexylmethyl, Br), (H, H, cyclohexylmethyl, Me), (H, F, H, H), (H, F, H, Cl), (H, F, H, F), (H, F, H, CF₃), (H, F, H, Br), (H, F, H, Me), (H, F, F, H), (H, F, F, Cl), (H, F, F, F), (H, F, F, CF₃), (H, F, F, Br), (H, F, F, Me), (H, F, Cl, H), (H, F, Cl, Cl), (H, F, Cl, F), (H, F, Cl, CF₃), (H, F, Cl, Br), (H, F, Cl, Me), (H, F, Me, H), (H, F, Me, Cl), (H, F, Me, F), (H, F, Me, CF₃), (H, F, Me, Br), (H, F, Me, Me), (H, F, Et, H), (H, F, Et, Cl), (H, F, Et, F), (H, F, Et, CF₃), (H, F, Et, Br), (H, F, Et, Me), (H, F, n-Pr, H), (H, F, n-Pr, Cl), (H, F, n-Pr, F), (H, F, n-Pr, CF₃), (H, F, n-Pr, Br), (H, F, n-Pr, Me), (H, F, c-Pr, H), (H, F, c-Pr, Cl), (H, F, c-Pr, F), (H, F, c-Pr, CF₃), (H, F, c-Pr, Br), (H, F, c-Pr, Me), (H, F, i-Pr, H), (H, F, i-Pr, Cl), (H, F, i-Pr, F), (H, F, i-Pr, CF₃), (H, F, i-Pr, Br), (H, F, i-Pr, Me), (H, F, n-Bu, H), (H, F, n-Bu, Cl), (H, F, n-Bu, F), (H, F, n-Bu, CF₃), (H, F, n-Bu, Br), (H, F, n-Bu, Me), (H, F, i-Bu, H), (H, F, i-Bu, Cl), (H, F, i-Bu, F), (H, F, i-Bu, CF₃), (H, F, i-Bu, Br), (H, F, i-Bu, Me), (H, F, sec-Bu, H), (H, F, sec-Bu, Cl), (H, F, sec-Bu, F), (H, F, sec-Bu, CF₃), (H, F, sec-Bu, Br), (H, F, sec-Bu, Me), (H, F, n-Pen, H), (H, F, n-Pen, Cl), (H, F, n-Pen, F), (H, F, n-Pen, CF₃), (H, F, n-Pen, Br), (H, F, n-Pen, Me), (H, F, c-Pen, H), (H, F, c-Pen, Cl), (H, F, c-Pen, F), (H, F, c-Pen, CF₃), (H, F, c-Pen, Br), (H, F, c-Pen, Me), (H, F, n-Hex, H), (H, F, n-Hex, Cl), (H, F, n-Hex, F), (H, F, n-Hex, CF₃), (H, F, n-Hex, Br), (H, F, n-Hex, Me), (H, F, c-Hex, H), (H, F, c-Hex, Cl), (H, F, c-Hex, F), (H, F, c-Hex, CF₃), (H, F, c-Hex, Br), (H, F, c-Hex, Me), (H, F, OH, H), (H, F, OH, Cl), (H, F, OH, F), (H, F, OH, CF₃), (H, F, OH, Br), (H, F, OH, Me), (H, F, MeO, H), (H, F, MeO, Cl), (H, F, MeO, F), (H, F, MeO, CF₃), (H, F, MeO, Br), (H, F, MeO, Me), (H, F, EtO, H), (H, F, EtO, Cl), (H, F, EtO, F), (H, F, EtO, CF₃), (H, F, EtO, Br), (H, F, EtO, Me), (H, F, n-PrO, H), (H, F, n-PrO, Cl), (H, F, n-PrO, F), (H, F, n-PrO, CF₃), (H, F, n-PrO, Br), (H, F, n-PrO, Me), (H, F, PhO, H), (H, F, PhO, Cl), (H, F, PhO, F), (H, F, PhO, CF₃), (H, F, PhO, Br), (H, F, PhO, Me), (H, F, BnO, H), (H, F, BnO, Cl), (H, F, BnO, F), (H, F, BnO, CF₃), (H, F, BnO, Br), (H, F, BnO, Me), (H, F, PhCH₂CH₂O, H), (H, F, PhCH₂CH₂O, Cl), (H, F, PhCH₂CH₂O, F), (H, F, PhCH₂CH₂O, CF₃), (H, F, PhCH₂CH₂O, Br), (H, F, PhCH₂CH₂O, Me), (H, F, CF₃, H), (H, F, CF₃, Cl), (H, F, CF₃, F), (H, F, CF₃, CF₃), (H, F, CF₃, Br), (H, F, CF₃, Me), (H, F, CF₃O, H), (H, F, CF₃O, Cl), (H, F, CF₃O, F), (H, F, CF₃O, CF₃), (H, F, CF₃O, Br), (H, F, CF₃O, Me), (H, F, Ph, H), (H, F, Ph, Cl), (H, F, Ph, F), (H, F, Ph, CF₃), (H, F, Ph, Br), (H, F, Ph, Me), (H, F, 4-F-Ph, H), (H, F, 4-F-Ph, Cl), (H, F, 4-F-Ph, F), (H, F, 4-F-Ph, CF₃), (H, F, 4-F-Ph, Br), (H, F, 4-F-Ph, Me), (H, F, 4-CF₃-Ph, H), (H, F, 4-CF₃-Ph, Cl), (H, F, 4-CF₃-Ph, F), (H, F, 4-CF₃-Ph, CF₃), (H, F, 4-CF₃-Ph, Br), (H, F, 4-CF₃-Ph, Me), (H, F, 4-(Me)₂N-Ph, H), (H, F, 4-(Me)₂N-Ph, Cl), (H, F, 4-(Me)₂N-Ph, F), (H, F, 4-(Me)₂N-Ph, CF₃), (H, F, 4-(Me)₂N-Ph, Br), (H, F, 4-(Me)₂N-Ph, Me), (H, F, 4-OH-Ph, H), (H, F, 4-OH-Ph, Cl), (H, F, 4-OH-Ph, F), (H, F, 4-OH-Ph, CF₃), (H, F, 4-OH-Ph, Br), (H, F, 4-OH-Ph, Me), (H, F, 3,4-di-F-Ph, H), (H, F, 3,4-di-F-Ph, Cl), (H, F, 3,4-di-F-Ph, F), (H, F, 3,4-di-F-Ph, CF₃), (H, F, 3,4-di-F-Ph, Br), (H, F, 3,4-di-F-Ph, Me), (H, F, 4-COOH-Ph, H), (H, F, 4-COOH-Ph, Cl), (H, F, 4-COOH-Ph, F), (H, F, 4-COOH-Ph, CF₃), (H, F, 4-COOH-Ph, Br), (H, F, 4-COOH-Ph, Me), (H, F, Bn, H), (H, F, Bn, Cl), (H, F, Bn, F), (H, F, Bn, CF₃), (H, F, Bn, Br), (H, F, Bn, Me), (H, F, 4-F-Bn, H), (H, F, 4-F-Bn, Cl), (H, F, 4-F-Bn, F), (H, F, 4-F-Bn, CF₃), (H, F, 4-F-Bn, Br), (H, F, 4-F-Bn, Me), (H, F, 2-Py, H), (H, F, 2-Py, Cl), (H, F, 2-Py, F), (H, F, 2-Py, CF₃), (H, F, 2-Py, Br), (H, F, 2-Py, Me), (H, F, 3-Py, H), (H, F, 3-Py, Cl), (H, F, 3-Py, F), (H, F, 3-Py, CF₃), (H, F, 3-Py, Br), (H, F, 3-Py, Me), (H, F, 4-Py, H), (H, F, 4-Py, Cl), (H, F, 4-Py, F), (H, F, 4-Py, CF₃), (H, F, 4-Py, Br), (H, F, 4-Py, Me), (H, F, 2-Th, H), (H, F, 2-Th, Cl), (H, F, 2-Th, F), (H, F, 2-Th, CF₃), (H, F, 2-Th, Br), (H, F, 2-Th, Me), (H, F, 3-Th, H), (H, F, 3-Th, Cl), (H, F, 3-Th, F), (H, F, 3-Th, CF₃), (H, F, 3-Th, Br), (H, F, 3-Th, Me), (H, F, Pyrazol-2-yl, H), (H, F, Pyrazol-2-yl, Cl), (H, F, Pyrazol-2-yl, F), (H, F, Pyrazol-2-yl, CF₃), (H, F, Pyrazol-2-yl, Br), (H, F, Pyrazol-2-yl, Me), (H, F, Pyrazol-3-yl, H), (H, F, Pyrazol-3-yl, Cl), (H, F, Pyrazol-3-yl, F), (H, F, Pyrazol-3-yl, CF₃), (H, F, Pyrazol-3-yl, Br), (H, F, Pyrazol-3-yl, Me), (H, F, pyrimidin-2-yl, H), (H, F, pyrimidin-2-yl, Cl), (H, F, pyrimidin-2-yl, F), (H, F, pyrimidin-2-yl, CF₃), (H, F, pyrimidin-2-yl, Br), (H, F, pyrimidin-2-yl, Me), (H, F, pyrimidin-4-yl, H), (H, F, pyrimidin-4-yl, Cl), (H, F, pyrimidin-4-yl, F), (H, F, pyrimidin-4-yl, CF₃), (H, F, pyrimidin-4-yl, Br), (H, F, pyrimidin-4-yl, Me), (H, F, pyrimidin-5-yl, H), (H, F, pyrimidin-5-yl, Cl), (H, F, pyrimidin-5-yl, F), (H, F, pyrimidin-5-yl, CF₃), (H, F, pyrimidin-5-yl, Br), (H, F, pyrimidin-5-yl, Me), (H, F, HOOCCH₂CH₂CH₂, H), (H, F, HOOCCH₂CH₂CH₂, Cl), (H, F, HOOCCH₂CH₂CH₂, F), (H, F, HOOCCH₂CH₂CH₂, CF₃), (H, F, HOOCCH₂CH₂CH₂, Br), (H, F, HOOCCH₂CH₂CH₂, Me), (H, F, HOOCCH₂CH₂CH₂CH₂, H), (H, F, HOOCCH₂CH₂CH₂CH₂, Cl), (H, F, HOOCCH₂CH₂CH₂CH₂, F), (H, F, HOOCCH₂CH₂CH₂CH₂, CF₃), (H, F, HOOCCH₂CH₂CH₂CH₂, Br), (H, F, HOOCCH₂CH₂CH₂CH₂, Me), (H, F, (Me)₂NCOCH₂CH₂CH₂, H), (H, F, (Me)₂NCOCH₂CH₂CH₂, Cl), (H, F, (Me)₂NCOCH₂CH₂CH₂, F), (H, F, (Me)₂NCOCH₂CH₂CH₂, CF₃), (H, F, (Me)₂NCOCH₂CH₂CH₂, Br), (H, F, (Me)₂NCOCH₂CH₂CH₂, Me), (H, F, (Me)₂NCOCH₂CH₂CH₂CH₂, H), (H, F, (Me)₂NCOCH₂CH₂CH₂CH₂, Cl), (H, F, (Me)₂NCOCH₂CH₂CH₂CH₂, F), (H, F, (Me)₂NCOCH₂CH₂CH₂CH₂, CF₃), (H, F, (Me)₂NCOCH₂CH₂CH₂CH₂, Br), (H, F, (Me)₂NCOCH₂CH₂CH₂CH₂, Me), (H, F, MeOCH₂, H), (H, F, MeOCH₂, Cl), (H, F, MeOCH₂, F), (H, F, MeOCH₂, CF₃), (H, F, MeOCH₂, Br), (H, F, MeOCH₂, Me), (H, F, EtOCH₂, H), (H, F, EtOCH₂, Cl), (H, F, EtOCH₂, F), (H, F, EtOCH₂, CF₃), (H, F, EtOCH₂, Br), (H, F, EtOCH₂, Me), (H, F, EtOCH₂CH₂, H), (H, F, EtOCH₂CH₂, Cl), (H, F, EtOCH₂CH₂, F), (H, F, EtOCH₂CH₂, CF₃), (H, F, EtOCH₂CH₂, Br), (H, F, EtOCH₂CH₂, Me), (H, F, MeOCH₂CH₂OCH₂CH₂, H), (H, F, MeOCH₂CH₂OCH₂CH₂, Cl), (H, F, MeOCH₂CH₂OCH₂CH₂, F), (H, F, MeOCH₂CH₂OCH₂CH₂, CF₃), (H, F, MeOCH₂CH₂OCH₂CH₂, Br), (H, F, MeOCH₂CH₂OCH₂CH₂, Me), (H, F, MeOCH₂CH₂, H), (H, F, MeOCH₂CH₂, Cl), (H, F, MeOCH₂CH₂, F), (H, F, MeOCH₂CH₂, CF₃), (H, F, MeOCH₂CH₂, Br), (H, F, MeOCH₂CH₂, Me), (H, F, HOCH₂, H), (H, F, HOCH₂, Cl), (H, F, HOCH₂, F), (H, F, HOCH₂, CF₃), (H, F, HOCH₂, Br), (H, F, HOCH₂, Me), (H, F, HOCH₂CH₂, H), (H, F, HOCH₂CH₂, Cl), (H, F, HOCH₂CH₂, F), (H, F, HOCH₂CH₂, CF₃), (H, F, HOCH₂CH₂, Br), (H, F, HOCH₂CH₂, Me), (H, F, HOCH₂CH₂CH₂, H), (H, F, HOCH₂CH₂CH₂, Cl), (H, F, HOCH₂CH₂CH₂, F), (H, F, HOCH₂CH₂CH₂, CF₃), (H, F, HOCH₂CH₂CH₂, Br), (H, F, HOCH₂CH₂CH₂, Me), (H, F, HOCH₂CH₂CH₂CH₂, H), (H, F, HOCH₂CH₂CH₂CH₂, Cl), (H, F, HOCH₂CH₂CH₂CH₂, F), (H, F, HOCH₂CH₂CH₂CH₂, CF₃), (H, F, HOCH₂CH₂CH₂CH₂, Br), (H, F, HOCH₂CH₂CH₂CH₂, Me), (H, F, HOCH₂CH₂CH₂CH₂CH₂, H), (H, F, HOCH₂CH₂CH₂CH₂CH₂, Cl), (H, F, HOCH₂CH₂CH₂CH₂CH₂, F), (H, F, HOCH₂CH₂CH₂CH₂CH₂, CF₃), (H, F, HOCH₂CH₂CH₂CH₂CH₂, Br), (H, F, HOCH₂CH₂CH₂CH₂CH₂, Me), (H, F, HOCH₂CH₂OCH₂CH₂, H), (H, F, HOCH₂CH₂OCH₂CH₂, Cl), (H, F, HOCH₂CH₂OCH₂CH₂, F), (H, F, HOCH₂CH₂OCH₂CH₂, CF₃), (H, F, HOCH₂CH₂OCH₂CH₂, Br), (H, F, HOCH₂CH₂OCH₂CH₂, Me), (H, F, (Me)₂N, H), (H, F, (Me)₂N, Cl), (H, F, (Me)₂N, F), (H, F, (Me)₂N, CF₃), (H, F, (Me)₂N, Br), (H, F, (Me)₂N, Me), (H, F, piperidin-4-yl-methyl, H), (H, F, piperidin-4-yl-methyl, Cl), (H, F, piperidin-4-yl-methyl, F), (H, F, piperidin-4-yl-methyl, CF₃), (H, F, piperidin-4-yl-methyl, Br), (H, F, piperidin-4-yl-methyl, Me), (H, F, cyclohexylmethyl, H), (H, F, cyclohexylmethyl, Cl), (H, F, cyclohexylmethyl, F), (H, F, cyclohexylmethyl, CF₃), (H, F, cyclohexylmethyl, Br), (H, F, cyclohexylmethyl, Me), (H, Cl, H, H), (H, Cl, H, Cl), (H, Cl, H, F), (H, Cl, H, CF₃), (H, Cl, H, Br), (H, Cl, H, Me), (H, Cl, F, H), (H, Cl, F, Cl), (H, Cl, F, F), (H, Cl, F, CF₃), (H, Cl, F, Br), (H, Cl, F, Me), (H, Cl, Cl, H), (H, Cl, Cl, Cl), (H, Cl, Cl, F), (H, Cl, Cl, CF₃), (H, Cl, Cl, Br), (H, Cl, Cl, Me), (H, Cl, Me, H), (H, Cl, Me, Cl), (H, Cl, Me, F), (H, Cl, Me, CF₃), (H, Cl, Me, Br), (H, Cl, Me, Me), (H, Cl, Et, H), (H, Cl, Et, Cl), (H, Cl, Et, F), (H, Cl, Et, CF₃), (H, Cl, Et, Br), (H, Cl, Et, Me), (H, Cl, n-Pr, H), (H, Cl, n-Pr, Cl), (H, Cl, n-Pr, F), (H, Cl, n-Pr, CF₃), (H, Cl, n-Pr, Br), (H, Cl, n-Pr, Me), (H, Cl, c-Pr, H), (H, Cl, c-Pr, Cl), (H, Cl, c-Pr, F), (H, Cl, c-Pr, CF₃), (H, Cl, c-Pr, Br), (H, Cl, c-Pr, Me), (H, Cl, i-Pr, H), (H, Cl, i-Pr, Cl), (H, Cl, i-Pr, F), (H, Cl, i-Pr, CF₃), (H, Cl, i-Pr, Br), (H, Cl, i-Pr, Me), (H, Cl, n-Bu, H), (H, Cl, n-Bu, Cl), (H, Cl, n-Bu, F), (H, Cl, n-Bu, CF₃), (H, Cl, n-Bu, Br), (H, Cl, n-Bu, Me), (H, Cl, i-Bu, H), (H, Cl, i-Bu, Cl), (H, Cl, i-Bu, F), (H, Cl, i-Bu, CF₃), (H, Cl, i-Bu, Br), (H, Cl, i-Bu, Me), (H, Cl, sec-Bu, H), (H, Cl, sec-Bu, Cl), (H, Cl, sec-Bu, F), (H, Cl, sec-Bu, CF₃), (H, Cl, sec-Bu, Br), (H, Cl, sec-Bu, Me), (H, Cl, n-Pen, H), (H, Cl, n-Pen, Cl), (H, Cl, n-Pen, F), (H, Cl, n-Pen, CF₃), (H, Cl, n-Pen, Br), (H, Cl, n-Pen, Me), (H, Cl, c-Pen, H), (H, Cl, c-Pen, Cl), (H, Cl, c-Pen, F), (H, Cl, c-Pen, CF₃), (H, Cl, c-Pen, Br), (H, Cl, c-Pen, Me), (H, Cl, n-Hex, H), (H, Cl, n-Hex, Cl), (H, Cl, n-Hex, F), (H, Cl, n-Hex, CF₃), (H, Cl, n-Hex, Br), (H, Cl, n-Hex, Me), (H, Cl, c-Hex, H), (H, Cl, c-Hex, Cl), (H, Cl, c-Hex, F), (H, Cl, c-Hex, CF₃), (H, Cl, c-Hex, Br), (H, Cl, c-Hex, Me), (H, Cl, OH, H), (H, Cl, OH, Cl), (H, Cl, OH, F), (H, Cl, OH, CF₃), (H, Cl, OH, Br), (H, Cl, OH, Me), (H, Cl, MeO, H), (H, Cl, MeO, Cl), (H, Cl, MeO, F), (H, Cl, MeO, CF₃), (H, Cl, MeO, Br), (H, Cl, MeO, Me), (H, Cl, EtO, H), (H, Cl, EtO, Cl), (H, Cl, EtO, F), (H, Cl, EtO, CF₃), (H, Cl, EtO, Br), (H, Cl, EtO, Me), (H, Cl, n-PrO, H), (H, Cl, n-PrO, Cl), (H, Cl, n-PrO, F), (H, Cl, n-PrO, CF₃), (H, Cl, n-PrO, Br), (H, Cl, n-PrO, Me), (H, Cl, PhO, H), (H, Cl, PhO, Cl), (H, Cl, PhO, F), (H, Cl, PhO, CF₃), (H, Cl, PhO, Br), (H, Cl, PhO, Me), (H, Cl, BnO, H), (H, Cl, BnO, Cl), (H, Cl, BnO, F), (H, Cl, BnO, CF₃), (H, Cl, BnO, Br), (H, Cl, BnO, Me), (H, Cl, PhCH₂CH₂O, H), (H, Cl, PhCH₂CH₂O, Cl), (H, Cl, PhCH₂CH₂O, F), (H, Cl, PhCH₂CH₂O, CF₃), (H, Cl, PhCH₂CH₂O, Br), (H, Cl, PhCH₂CH₂O, Me), (H, Cl, CF₃, H), (H, Cl, CF₃, Cl), (H, Cl, CF₃, F), (H, Cl, CF₃, CF₃), (H, Cl, CF₃, Br), (H, Cl, CF₃, Me), (H, Cl, CF₃O, H), (H, Cl, CF₃O, Cl), (H, Cl, CF₃O, F), (H, Cl, CF₃O, CF₃), (H, Cl, CF₃O, Br), (H, Cl, CF₃O, Me), (H, Cl, Ph, H), (H, Cl, Ph, Cl), (H, Cl, Ph, F), (H, Cl, Ph, CF₃), (H, Cl, Ph, Br), (H, Cl, Ph, Me), (H, Cl, 4-F-Ph, H), (H, Cl, 4-F-Ph, Cl), (H, Cl, 4-F-Ph, F), (H, Cl, 4-F-Ph, CF₃), (H, Cl, 4-F-Ph, Br), (H, Cl, 4-F-Ph, Me), (H, Cl, 4-CF₃-Ph, H), (H, Cl, 4-CF₃-Ph, Cl), (H, Cl, 4-CF₃-Ph, F), (H, Cl, 4-CF₃-Ph, CF₃), (H, Cl, 4-CF₃-Ph, Br), (H, Cl, 4-CF₃-Ph, Me), (H, Cl, 4-(Me)₂N-Ph, H), (H, Cl, 4-(Me)₂N-Ph, Cl), (H, Cl, 4-(Me)₂N-Ph, F), (H, Cl, 4-(Me)₂N-Ph, CF₃), (H, Cl, 4-(Me)₂N-Ph, Br), (H, Cl, 4-(Me)₂N-Ph, Me), (H, Cl, 4-OH-Ph, H), (H, Cl, 4-OH-Ph, Cl), (H, Cl, 4-OH-Ph, F), (H, Cl, 4-OH-Ph, CF₃), (H, Cl, 4-OH-Ph, Br), (H, Cl, 4-OH-Ph, Me), (H, Cl, 3,4-di-F-Ph, H), (H, Cl, 3,4-di-F-Ph, Cl), (H, Cl, 3,4-di-F-Ph, F), (H, Cl, 3,4-di-F-Ph, CF₃), (H, Cl, 3,4-di-F-Ph, Br), (H, Cl, 3,4-di-F-Ph, Me), (H, Cl, 4-COOH-Ph, H), (H, Cl, 4-COOH-Ph, Cl), (H, Cl, 4-COOH-Ph, F), (H, Cl, 4-COOH-Ph, CF₃), (H, Cl, 4-COOH-Ph, Br), (H, Cl, 4-COOH-Ph, Me), (H, Cl, Bn, H), (H, Cl, Bn, Cl), (H, Cl, Bn, F), (H, Cl, Bn, CF₃), (H, Cl, Bn, Br), (H, Cl, Bn, Me), (H, Cl, 4-F-Bn, H), (H, Cl, 4-F-Bn, Cl), (H, Cl, 4-F-Bn, F), (H, Cl, 4-F-Bn, CF₃), (H, Cl, 4-F-Bn, Br), (H, Cl, 4-F-Bn, Me), (H, Cl, 2-Py, H), (H, Cl, 2-Py, Cl), (H, Cl, 2-Py, F), (H, Cl, 2-Py, CF₃), (H, Cl, 2-Py, Br), (H, Cl, 2-Py, Me), (H, Cl, 3-Py, H), (H, Cl, 3-Py, Cl), (H, Cl, 3-Py, F), (H, Cl, 3-Py, CF₃), (H, Cl, 3-Py, Br), (H, Cl, 3-Py, Me), (H, Cl, 4-Py, H), (H, Cl, 4-Py, Cl), (H, Cl, 4-Py, F), (H, Cl, 4-Py, CF₃), (H, Cl, 4-Py, Br), (H, Cl, 4-Py, Me), (H, Cl, 2-Th, H), (H, Cl, 2-Th, Cl), (H, Cl, 2-Th, F), (H, Cl, 2-Th, CF₃), (H, Cl, 2-Th, Br), (H, Cl, 2-Th, Me), (H, Cl, 3-Th, H), (H, Cl, 3-Th, Cl), (H, Cl, 3-Th, F), (H, Cl, 3-Th, CF₃), (H, Cl, 3-Th, Br), (H, Cl, 3-Th, Me), (H, Cl, Pyrazol-2-yl, H), (H, Cl, Pyrazol-2-yl, Cl), (H, Cl, Pyrazol-2-yl, F), (H, Cl, Pyrazol-2-yl, CF₃), (H, Cl, Pyrazol-2-yl, Br), (H, Cl, Pyrazol-2-yl, Me), (H, Cl, Pyrazol-3-yl, H), (H, Cl, Pyrazol-3-yl, Cl), (H, Cl, Pyrazol-3-yl, F), (H., Cl, Pyrazol-3-yl, CF₃), (H, Cl, Pyrazol-3-yl, Br), (H, Cl, Pyrazol-3-yl, Me), (H, Cl, pyrimidin-2-yl, H), (H, Cl, pyrimidin-2-yl, Cl), (H, Cl, pyrimidin-2-yl, F), (H, Cl, pyrimidin-2-yl, CF₃), (H, Cl, pyrimidin-2-yl, Br), (H, Cl, pyrimidin-2-yl, Me), (H, Cl, pyrimidin-4-yl, H), (H. Cl, pyrimidin-4-yl, Cl), (H, Cl, pyrimidin-4-yl, F), (H, Cl, pyrimidin-4-yl, CF₃), (H, Cl, pyrimidin-4-yl, Br), (H, Cl, pyrimidin-4-yl, Me), (H, Cl, pyrimidin-5-yl, H), (H, Cl, pyrimidin-5-yl, Cl), (H, Cl, pyrimidin-5-yl, F), (H, Cl, pyrimidin-5-yl, CF₃), (H, Cl, pyrimidin-5-yl, Br), (H, Cl, pyrimidin-5-yl, Me), (H, Cl, HOOCCH₂CH₂CH₂, H), (H, Cl, HOOCCH₂CH₂CH₂, Cl), (H, Cl, HOOCCH₂CH₂CH₂, F), (H, Cl, HOOCCH₂CH₂CH₂, CF₃), (H, Cl, HOOCCH₂CH₂CH₂, Br), (H, Cl, HOOCCH₂CH₂CH₂, Me), (H, Cl, HOOCCH₂CH₂CH₂CH₂, H), (H, Cl, HOOCCH₂CH₂CH₂CH₂, Cl), (H, Cl, HOOCCH₂CH₂CH₂CH₂, F), (H, Cl, HOOCCH₂CH₂CH₂CH₂, CF₃), (H, Cl, HOOCCH₂CH₂CH₂CH₂, Br), (H, Cl, HOOCCH₂CH₂CH₂CH₂, Me), (H, Cl, (Me)₂NCOCH₂CH₂CH₂, H), (H, Cl, (Me)₂NCOCH₂CH₂CH₂, Cl), (H, Cl, (Me)₂NCOCH₂CH₂CH₂, F), (H, Cl, (Me)₂NCOCH₂CH₂CH₂, CF₃), (H, Cl, (Me)₂NCOCH₂CH₂CH₂, Br), (H, Cl, (Me)₂NCOCH₂CH₂CH₂, Me), (H, Cl, (Me)₂NCOCH₂CH₂CH₂CH₂, H), (H, Cl, (Me)₂NCOCH₂CH₂CH₂CH₂, Cl), (H, Cl, (Me)₂NCOCH₂CH₂CH₂CH₂, F), (H, Cl, (Me)₂NCOCH₂CH₂CH₂CH₂, CF₃), (H, Cl, (Me)₂NCOCH₂CH₂CH₂CH₂, Br), (H, Cl, (Me)₂NCOCH₂CH₂CH₂CH₂, Me), (H, Cl, MeOCH₂, H), (H, Cl, MeOCH₂, Cl), (H, Cl, MeOCH₂, F), (H, Cl, MeOCH₂, CF₃), (H, Cl, MeOCH₂, Br), (H, Cl, MeOCH₂, Me), (H, Cl, EtOCH₂, H), (H, Cl, EtOCH₂, Cl), (H, Cl, EtOCH₂, F), (H, Cl, EtOCH₂, CF₃), (H, Cl, EtOCH₂, Br), (H, Cl, EtOCH₂, Me), (H, Cl, EtOCH₂CH₂, H), (H, Cl, EtOCH₂CH₂, Cl), (H, Cl, EtOCH₂CH₂, F), (H, Cl, EtOCH₂CH₂, CF₃), (H, Cl, EtOCH₂CH₂, Br), (H, Cl, EtOCH₂CH₂, Me), (H, Cl, MeOCH₂CH₂OCH₂CH₂, H), (H, Cl, MeOCH₂CH₂OCH₂CH₂, Cl), (H, Cl, MeOCH₂CH₂OCH₂CH₂, F), (H, Cl, MeOCH₂CH₂OCH₂CH₂, CF₃), (H, Cl, MeOCH₂CH₂OCH₂CH₂, Br), (H, Cl, MeOCH₂CH₂OCH₂CH₂, Me), (H, Cl, MeOCH₂CH₂, H), (H, Cl, MeOCH₂CH₂, Cl), (H, Cl, MeOCH₂CH₂, F), (H, Cl, MeOCH₂CH₂, CF₃), (H, Cl, MeOCH₂CH₂, Br), (H, Cl, MeOCH₂CH₂, Me), (H, Cl, HOCH₂, H), (H, Cl, HOCH₂, Cl), (H, Cl, HOCH₂, F), (H, Cl, HOCH₂, CF₃), (H, Cl, HOCH₂, Br), (H, Cl, HOCH₂, Me), (H, Cl, HOCH₂CH₂, H), (H, Cl, HOCH₂CH₂, Cl), (H, Cl, HOCH₂CH₂, F), (H, Cl, HOCH₂CH₂, CF₃), (H, Cl, HOCH₂CH₂, Br), (H, Cl, HOCH₂CH₂, Me), (H, Cl, HOCH₂CH₂CH₂, H), (H, Cl, HOCH₂CH₂CH₂, Cl), (H, Cl, HOCH₂CH₂CH₂, F), (H, Cl, HOCH₂CH₂CH₂, CF₃), (H, Cl, HOCH₂CH₂CH₂, Br), (H, Cl, HOCH₂CH₂CH₂, Me), (H, Cl, HOCH₂CH₂CH₂CH₂, H), (H, Cl, HOCH₂CH₂CH₂CH₂, Cl), (H, Cl, HOCH₂CH₂CH₂CH₂, F), (H, Cl, HOCH₂CH₂CH₂CH₂, CF₃), (H, Cl, HOCH₂CH₂CH₂CH₂, Br), (H, Cl, HOCH₂CH₂CH₂CH₂, Me), (H, Cl, HOCH₂CH₂CH₂CH₂CH₂, H), (H, Cl, HOCH₂CH₂CH₂CH₂CH₂, Cl), (H, Cl, HOCH₂CH₂CH₂CH₂CH₂, F), (H, Cl, HOCH₂CH₂CH₂CH₂CH₂, CF₃), (H, Cl, HOCH₂CH₂CH₂CH₂CH₂, Br), (H, Cl, HOCH₂CH₂CH₂CH₂CH₂, Me), (H, Cl, HOCH₂CH₂OCH₂CH₂, H), (H, Cl, HOCH₂CH₂OCH₂CH₂, Cl), (H, Cl, HOCH₂CH₂OCH₂CH₂, F), (H, Cl, HOCH₂CH₂OCH₂CH₂, CF₃), (H, Cl, HOCH₂CH₂OCH₂CH₂, Br), (H, Cl, HOCH₂CH₂OCH₂CH₂, Me), (H, Cl, (Me)₂N, H), (H, Cl, (Me)₂N, Cl), (H, Cl, (Me)₂N, F), (H, Cl, (Me)₂N, CF₃), (H, Cl, (Me)₂N, Br), (H, Cl, (Me)₂N, Me), (H, Cl, piperidin-4-yl-methyl, H), (H, Cl, piperidin-4-yl-methyl, Cl), (H, Cl, piperidin-4-yl-methyl, F), (H, Cl, piperidin-4-yl-methyl, CF₃), (H, Cl, piperidin-4-yl-methyl, Br), (H, Cl, piperidin-4-yl-methyl, Me), (H, Cl, cyclohexylmethyl, H), (H, Cl, cyclohexylmethyl, Cl), (H, Cl, cyclohexylmethyl, F), (H, Cl, cyclohexylmethyl, CF₃), (H, Cl, cyclohexylmethyl, Br), (H, Cl, cyclohexylmethyl, Me), (F, H, H, H), (F, H, H, Cl), (F, H, H, F), (F, H, H, CF₃), (F, H, H, Br), (F, H, H, Me), (F, H, F, H), (F, H, F, Cl), (F, H, F, F), (F, H, F, CF₃), (F, H, F, Br), (F, H, F, Me), (F, H, Cl, H), (F, H, Cl, Cl), (F, H, Cl, F), (F, H, Cl, CF₃), (F, H, Cl, Br), (F, H, Cl, Me), (F, H, Me, H), (F, H, Me, Cl), (F, H, Me, F), (F, H, Me, CF₃), (F, H, Me, Br), (F, H, Me, Me), (F, H, Et, H), (F, H, Et, Cl), (F, H, Et, F), (F, H, Et, CF₃), (F, H, Et, Br), (F, H, Et, Me), (F, H, n-Pr, H), (F, H, n-Pr, Cl), (F, H, n-Pr, F), (F, H, n-Pr, CF₃), (F, H, n-Pr, Br), (F, H, n-Pr, Me), (F, H, c-Pr, H), (F, H, c-Pr, Cl), (F, H, c-Pr, F), (F, H, c-Pr, CF₃), (F, H, c-Pr, Br), (F, H, c-Pr, Me), (F, H, i-Pr, H), (F, H, i-Pr, Cl), (F, H, i-Pr, F), (F, H, i-Pr, CF₃), (F, H, i-Pr, Br), (F, H, i-Pr, Me), (F, H, n-Bu, H), (F, H, n-Bu, Cl), (F, H, n-Bu, F), (F, H, n-Bu, CF₃), (F, H, n-Bu, Br), (F, H, n-Bu, Me), (F, H, i-Bu, H), (F, H, i-Bu, Cl), (F, H, i-Bu, F), (F, H, i-Bu, CF₃), (F, H, i-Bu, Br), (F, H, i-Bu, Me), (F, H, sec-Bu, H), (F, H, sec-Bu, Cl), (F, H, sec-Bu, F), (F, H, sec-Bu, CF₃), (F, H, sec-Bu, Br), (F, H, sec-Bu, Me), (F, H, n-Pen, H), (F, H, n-Pen, Cl), (F, H, n-Pen, F), (F, H, n-Pen, CF₃), (F, H, n-Pen, Br), (F, H, n-Pen, Me), (F, H, c-Pen, H), (F, H, c-Pen, Cl), (F, H, c-Pen, F), (F, H, c-Pen, CF₃), (F, H, c-Pen, Br), (F, H, c-Pen, Me), (F, H, n-Hex, H), (F, H, n-Hex, Cl), (F, H, n-Hex, F), (F, H, n-Hex, CF₃), (F, H, n-Hex, Br), (F, H, n-Hex, Me), (F, H, c-Hex, H), (F, H, c-Hex, Cl), (F, H, c-Hex, F), (F, H, c-Hex, CF₃), (F, H, c-Hex, Br), (F, H, c-Hex, Me), (F, H, OH, H), (F, H, OH, Cl), (F, H, OH, F), (F, H, OH, CF₃), (F, H, OH, Br), (F, H, OH, Me), (F, H, MeO, H), (F, H, MeO, Cl), (F, H, MeO, F), (F, H, MeO, CF₃), (F, H, MeO, Br), (F, H, MeO, Me), (F, H, EtO, H), (F, H, EtO, Cl), (F, H, EtO, F), (F, H, EtO, CF₃), (F, H, EtO, Br), (F, H, EtO, Me), (F, H, n-PrO, H), (F, H, n-PrO, Cl), (F, H, n-PrO, F), (F, H, n-PrO, CF₃), (F, H, n-PrO, Br), (F, H, n-PrO, Me), (F, H, PhO, H), (F, H, PhO, Cl), (F, H, PhO, F), (F, H, PhO, CF₃), (F, H, PhO, Br), (F, H, PhO, Me), (F, H, BnO, H), (F, H, BnO, Cl), (F, H, BnO, F), (F, H, BnO, CF₃), (F, H, BnO, Br), (F, H, BnO, Me), (F, H, PhCH₂CH₂O, H), (F, H, PhCH₂CH₂O, Cl), (F, H, PhCH₂CH₂O, F), (F, H, PhCH₂CH₂O, CF₃), (F, H, PhCH₂CH₂O, Br), (F, H, PhCH₂CH₂O, Me), (F, H, CF₃, H), (F, H, CF₃, Cl), (F, H, CF₃, F), (F, H, CF₃, CF₃), (F, H, CF₃, Br), (F, H, CF₃, Me), (F, H, CF₃O, H), (F, H, CF₃O, Cl), (F, H, CF₃O, F), (F, H, CF₃O, CF₃), (F, H, CF₃O, Br), (F, H, CF₃O, Me), (F, H, Ph, H), (F, H, Ph, Cl), (F, H, Ph, F), (F, H, Ph, CF₃), (F, H, Ph, Br), (F, H, Ph, Me), (F, H, 4-F-Ph, H), (F, H, 4-F-Ph, Cl), (F, H, 4-F-Ph, F), (F, H, 4-F-Ph, CF₃), (F, H, 4-F-Ph, Br), (F, H, 4-F-Ph, Me), (F, H, 4-CF₃-Ph, H), (F, H, 4-CF₃-Ph, Cl), (F, H, 4-CF₃-Ph, F), (F, H, 4-CF₃-Ph, CF₃), (F, H, 4-CF₃-Ph, Br), (F, H, 4-CF₃-Ph, Me), (F, H, 4-(Me)₂N-Ph, H), (F, H, 4-(Me)₂N-Ph, Cl), (F, H, 4-(Me)₂N-Ph, F), (F, H, 4-(Me)₂N-Ph, CF₃), (F, H, 4-(Me)₂N-Ph, Br), (F, H, 4-(Me)₂N-Ph, Me), (F, H, 4-OH-Ph, H), (F, H, 4-OH-Ph, Cl), (F, H, 4-OH-Ph, F), (F, H, 4-OH-Ph, CF₃), (F, H, 4-OH-Ph, Br), (F, H, 4-OH-Ph, Me), (F, H, 3,4-di-F-Ph, H), (F, H, 3,4-di-F-Ph, Cl), (F, H, 3,4-di-F-Ph, F), (F, H, 3,4-di-F-Ph, CF₃), (F, H, 3,4-di-F-Ph, Br), (F, H, 3,4-di-F-Ph, Me), (F, H, 4-COOH-Ph, H), (F, H, 4-COOH-Ph, Cl), (F, H, 4-COOH-Ph, F), (F, H, 4-COOH-Ph, CF₃), (F, H, 4-COOH-Ph, Br), (F, H, 4-COOH-Ph, Me), (F, H, Bn, H), (F, H, Bn, Cl), (F, H, Bn, F), (F, H, Bn, CF₃), (F, H, Bn, Br), (F, H, Bn, Me), (F, H, 4-F-Bn, H), (F, H, 4-F-Bn, Cl), (F, H, 4-F-Bn, F), (F, H, 4-F-Bn, CF₃), (F, H, 4-F-Bn, Br), (F, H, 4-F-Bn, Me), (F, H, 2-Py, H), (F, H, 2-Py, Cl), (F, H, 2-Py, F), (F, H, 2-Py, CF₃), (F, H, 2-Py, Br), (F, H, 2-Py, Me), (F, H, 3-Py, H), (F, H, 3-Py, Cl), (F, H, 3-Py, F), (F, H, 3-Py, CF₃), (F, H, 3-Py, Br), (F, H, 3-Py, Me), (F, H, 4-Py, H), (F, H, 4-Py, Cl), (F, H, 4-Py, F), (F, H, 4-Py, CF₃), (F, H, 4-Py, Br), (F, H, 4-Py, Me), (F, H, 2-Th, H), (F, H, 2-Th, Cl), (F, H, 2-Th, F), (F, H, 2-Th, CF₃), (F, H, 2-Th, Br), (F, H, 2-Th, Me), (F, H, 3-Th, H), (F, H, 3-Th, Cl), (F, H, 3-Th, F), (F, H, 3-Th, CF₃), (F, H, 3-Th, Br), (F, H, 3-Th, Me), (F, H, Pyrazol-2-yl, H), (F, H, Pyrazol-2-yl, Cl), (F, H, Pyrazol-2-yl, F), (F, H, Pyrazol-2-yl, CF₃), (F, H, Pyrazol-2-yl, Br), (F, H, Pyrazol-2-yl, Me), (F, H, Pyrazol-3-yl, H), (F, H, Pyrazol-3-yl, Cl), (F, H, Pyrazol-3-yl, F), (F, H, Pyrazol-3-yl, CF₃), (F, H, Pyrazol-3-yl, Br), (F, H, Pyrazol-3-yl, Me), (F, H, pyrimidin-2-yl, H), (F, H, pyrimidin-2-yl, Cl), (F, H, pyrimidin-2-yl, F), (F, H, pyrimidin-2-yl, CF₃), (F, H, pyrimidin-2-yl, Br), (F, H, pyrimidin-2-yl, Me), (F, H, pyrimidin-4-yl, H), (F, H, pyrimidin-4-yl, Cl), (F, H, pyrimidin-4-yl, F), (F, H, pyrimidin-4-yl, CF₃), (F, H, pyrimidin-4-yl, Br), (F, H, pyrimidin-4-yl, Me), (F, H, pyrimidin-5-yl, H), (F, H, pyrimidin-5-yl, Cl), (F, H, pyrimidin-5-yl, F), (F, H, pyrimidin-5-yl, CF₃), (F, H, pyrimidin-5-yl, Br), (F, H, pyrimidin-5-yl, Me), (F, H, HOOCCH₂CH₂CH₂, H), (F, H, HOOCCH₂CH₂CH₂, Cl), (F, H, HOOCCH₂CH₂CH₂, F), (F, H, HOOCCH₂CH₂CH₂, CF₃), (F, H, HOOCCH₂CH₂CH₂, Br), (F, H, HOOCCH₂CH₂CH₂, Me), (F, H, HOOCCH₂CH₂CH₂CH₂, H), (F, H, HOOCCH₂CH₂CH₂CH₂, Cl), (F, H, HOOCCH₂CH₂CH₂CH₂, F), (F, H, HOOCCH₂CH₂CH₂CH₂, CF₃), (F, H, HOOCCH₂CH₂CH₂CH₂, Br), (F, H, HOOCCH₂CH₂CH₂CH₂, Me), (F, H, (Me)₂NCOCH₂CH₂CH₂CH₂, H), (F, H, (Me)₂NCOCH₂CH₂CH₂CH₂, Cl), (F, H, (Me)₂NCOCH₂CH₂CH₂CH₂, F), (F, H, (Me)₂NCOCH₂CH₂CH₂CH₂, CF₃), (F, H, (Me)₂NCOCH₂CH₂CH₂CH₂, Br), (F, H, (Me)₂NCOCH₂CH₂CH₂CH₂, Me), (F, H, (Me)₂

NCOCH₂CH₂CH₂CH₂CH₂, H), (F, H, (Me)₂ Cl), (F, H, (Me)₂ NCOCH₂CH₂CH₂CH₂CH₂, F), (F, H, (Me)₂ NCOCH₂CH₂CH₂CH₂CH₂, CF₃), (F, H, (Me)₂ NCOCH₂CH₂CH₂CH₂CH₂, Br), (F, H, (Me)₂ NCOCH₂CH₂CH₂CH₂CH₂, Me), (F, H, MeOCH₂, H), (F, H, MeOCH₂, Cl), (F, H, MeOCH₂, F), (F, H, MeOCH₂, CF₃), (F, H, MeOCH₂, Br), (F, H, MeOCH₂, Me), (F, H, EtOCH₂, H), (F, H, EtOCH₂, Cl), (F, H, EtOCH₂, F), (F, H, EtOCH₂, CF₃), (F, H, EtOCH₂, Br), (F, H, EtOCH₂, Me), (F, H, EtOCH₂CH₂, H), (F, H, EtOCH₂CH₂, Cl), (F, H, EtOCH₂CH₂, F), (F, H, EtOCH₂CH₂, CF₃), (F, H, EtOCH₂CH₂, Br), (F, H, EtOCH₂CH₂, Me), (F, H, MeOCH₂CH₂OCH₂CH₂, H), (F, H, MeOCH₂CH₂OCH₂CH₂, Cl), (F, H, MeOCH₂CH₂OCH₂CH₂, F), (F, H, MeOCH₂CH₂OCH₂CH₂, CF₃), (F, H, MeOCH₂CH₂OCH₂CH₂, Br), (F, H, MeOCH₂CH₂OCH₂CH₂, Me), (F, H, MeOCH₂CH₂, H), (F, H, MeOCH₂CH₂, Cl), (F, H, MeOCH₂CH₂, F), (F, H, MeOCH₂CH₂, CF₃), (F, H, MeOCH₂CH₂, Br), (F, H, MeOCH₂CH₂, Me), (F, H, HOCH₂, H), (F, H, HOCH₂, Cl), (F, H, HOCH₂, F), (F, H, HOCH₂, CF₃), (F, H, HOCH₂, Br), (F, H, HOCH₂, Me), (F, H, HOCH₂CH₂, H), (F, H, HOCH₂CH₂, Cl), (F, H, HOCH₂CH₂, F), (F, H, HOCH₂CH₂, CF₃), (F. H, HOCH₂CH₂, Br), (F, H, HOCH₂CH₂, Me), (F, H, HOCH₂CH₂CH₂, H), (F, H, HOCH₂CH₂CH₂, Cl), (F, H, HOCH₂CH₂CH₂, F), (F, H, HOCH₂CH₂CH₂, CF₃), (F, H, HOCH₂CH₂CH₂, Br), (F, H, HOCH₂CH₂CH₂, Me), (F, H, HOCH₂CH₂CH₂CH₂, H), (F, H, HOCH₂CH₂CH₂CH₂, Cl), (F, H, HOCH₂CH₂CH₂CH₂, F), (F, H, HOCH₂CH₂CH₂CH₂, CF₃), (F, H, HOCH₂CH₂CH₂CH₂, Br), (F, H, HOCH₂CH₂CH₂CH₂, Me), (F, H, HOCH₂CH₂CH₂CH₂CH₂, H), (F, H, HOCH₂CH₂CH₂CH₂CH₂, Cl), (F, H, HOCH₂CH₂CH₂CH₂CH₂, F), (F, H, HOCH₂CH₂CH₂CH₂CH₂, CF₃), (F, H, HOCH₂CH₂CH₂CH₂CH₂, Br), (F, H, HOCH₂CH₂CH₂CH₂CH₂, Me), (F, H, HOCH₂CH₂OCH₂CH₂, H), (F, H, HOCH₂CH₂OCH₂CH₂, Cl), (F, H, HOCH₂CH₂OCH₂CH₂, F), (F, H, HOCH₂CH₂OCH₂CH₂, CF₃), (F, H, HOCH₂CH₂OCH₂CH₂, Br), (F, H, HOCH₂CH₂OCH₂CH₂, Me), (F, H, (Me)₂N, H), (F, H, (Me)₂N, Cl), (F, H, (Me)₂N, F), (F, H, (Me)₂N, CF₃), (F, H, (Me)₂N, Br), (F, H, (Me)₂N, Me), (F, H, piperidin-4-yl-methyl, H), (F, H, piperidin-4-yl-methyl, Cl), (F, H, piperidin-4-yl-methyl, F), (F, H, piperidin-4-yl-methyl, CF₃), (F, H, piperidin-4-yl-methyl, Br), (F, H, piperidin-4-yl-methyl, Me), (F, H, cyclohexylmethyl, H), (F, H, cyclohexylmethyl, Cl), (F, H, cyclohexylmethyl, F), (F, H, cyclohexylmethyl, CF₃), (F, H, cyclohexylmethyl, Br), (F, H, cyclohexylmethyl, Me), (F, F, H, H), (F, F, H, Cl), (F, F, H, F), (F, F, H, CF₃), (F, F, H, Br), (F, F, H, Me), (F, F, F, H), (F, F, F, Cl), (F, F, F, F), (F, F, F, CF₃), (F, F, F, Br), (F, F, F, Me), (F, F, Cl, H), (F, F, Cl, Cl), (F, F, Cl, F), (F, F, Cl, CF₃), (F, F, Cl, Br), (F, F, Cl, Me), (F, F, Me, H), (F, F, Me, Cl), (F, F, Me, F), (F, F, Me, CF₃), (F, F, Me, Br), (F, F, Me, Me), (F, F, Et, H), (F, F, Et, Cl), (F, F, Et, F), (F, F, Et, CF₃), (F, F, Et, Br), (F, F, Et, Me), (F, F, n-Pr, H), (F, F, n-Pr, Cl), (F, F, n-Pr, F), (F, F, n-Pr, CF₃), (F, F, n-Pr, Br), (F, F, n-Pr, Me), (F, F, c-Pr, H), (F, F, c-Pr, Cl), (F, F, c-Pr, F), (F, F, c-Pr, CF₃), (F, F, c-Pr, Br), (F, F, c-Pr, Me), (F, F, i-Pr, H), (F, F, i-Pr, Cl), (F, F, i-Pr, F), (F, F, i-Pr, CF₃), (F, F, i-Pr, Br), (F, F, i-Pr, Me), (F, F, n-Bu, H), (F, F, n-Bu, Cl), (F, F, n-Bu, F), (F, F, n-Bu, CF₃), (F, F, n-Bu, Br), (F, F, n-Bu, Me), (F, F, i-Bu, H), (F, F, i-Bu, Cl), (F, F, i-Bu, F), (F, F, i-Bu, CF₃), (F, F, i-Bu, Br), (F, F, i-Bu, Me), (F, F, sec-Bu, H), (F, F, sec-Bu, Cl), (F, F, sec-Bu, F), (F, F, sec-Bu, CF₃), (F, F, sec-Bu, Br), (F, F, sec-Bu, Me), (F, F, n-Pen, H), (F, F, n-Pen, Cl), (F, F, n-Pen, F), (F, F, n-Pen, CF₃), (F, F, n-Pen, Br), (F, F, n-Pen, Me), (F, F, c-Pen, H), (F, F, c-Pen, Cl), (F, F, c-Pen, F), (F, F, c-Pen, CF₃), (F, F, c-Pen, Br), (F, F, c-Pen, Me), (F, F, n-Hex, H), (F, F, n-Hex, Cl), (F, F, n-Hex, F), (F, F, n-Hex, CF₃), (F, F, n-Hex, Br), (F, F, n-Hex, Me), (F, F, c-Hex, H), (F, F, c-Hex, Cl), (F, F, c-Hex, F), (F, F, c-Hex, CF₃), (F, F, c-Hex, Br), (F, F, c-Hex, Me), (F, F, OH, H), (F, F, OH, Cl), (F, F, OH, F), (F, F, OH, CF₃), (F, F, OH, Br), (F, F, OH, Me), (F, F, MeO, H), (F, F, MeO, Cl), (F, F, MeO, F), (F, F, MeO, CF₃), (F, F, MeO, Br), (F, F, MeO, Me), (F, F, EtO, H), (F, F, EtO, Cl), (F, F, EtO, F), (F, F, EtO, CF₃), (F, F, EtO, Br), (F, F, EtO, Me), (F, F, n-PrO, H), (F, F, n-PrO, Cl), (F, F, n-PrO, F), (F, F, n-PrO, CF₃), (F, F, n-PrO, Br), (F, F, n-PrO, Me), (F, F, PhO, H), (F, F, PhO, Cl), (F, F, PhO, F), (F, F, PhO, CF₃), (F, F, PhO, Br), (F, F, PhO, Me), (F, F, BnO, H), (F, F, BnO, Cl), (F, F, BnO, F), (F, F, BnO, CF₃), (F, F, BnO, Br), (F, F, BnO, Me), (F, F, PhCH₂CH₂O, H), (F, F, PhCH₂CH₂O, Cl), (F, F, PhCH₂CH₂O, F), (F, F, PhCH₂CH₂O, CF₃), (F, F, PhCH₂CH₂O, Br), (F, F, PhCH₂CH₂O, Me), (F, F, CF₃, H), (F, F, CF₃, Cl), (F, F, CF₃, F), (F, F, CF₃, CF₃), (F, F, CF₃, Br), (F, F, CF₃, Me), (F, F, CF₃O, H), (F, F, CF₃O, Cl), (F, F, CF₃O, F), (F, F, CF₃O, CF₃), (F, F, CF₃O, Br), (F, F, CF₃O, Me), (F, F, Ph, H), (F, F, Ph, Cl), (F, F, Ph, F), (F, F, Ph, CF₃), (F, F, Ph, Br), (F, F, Ph, Me), (F, F, 4-F-Ph, H), (F, F, 4-F-Ph, Cl), (F, F, 4-F-Ph, F), (F, F, 4-F-Ph, CF₃), (F, F, 4-F-Ph, Br), (F, F, 4-F-Ph, Me), (F, F, 4-CF₃-Ph, H), (F, F, 4-CF₃-Ph, Cl), (F, F, 4-CF₃-Ph, F), (F, F, 4-CF₃-Ph, CF₃), (F, F, 4-CF₃-Ph, Br), (F, F, 4-CF₃-Ph, Me), (F, F, 4-(Me)₂N-Ph, H), (F, F, 4(Me)₂N-Ph, Cl), (F, F, 4-(Me)₂N-Ph, F), (F, F, 4-(Me)₂N-Ph, CF₃), (F, F, 4-(Me)₂N-Ph, Br), (F, F, 4-(Me)₂N-Ph, Me), (F, F, 4-OH-Ph, H), (F, F, 4-OH-Ph, Cl), (F, F, 4-OH-Ph, F), (F, F, 4-OH-Ph, CF₃), (F, F, 4-OH-Ph, Br), (F, F, 4-OH-Ph, Me), (F, F, 3,4-di-F-Ph, H), (F, F, 3,4-di-F-Ph, Cl), (F, F, 3,4-di-F-Ph, F), (F, F, 3,4-di-F-Ph, CF₃), (F, F, 3,4-di-F-Ph, Br), (F, F, 3,4-di-F-Ph, Me), (F, F, 4-COOH-Ph, H), (F, F, 4-COOH-Ph, Cl), (F, F, 4-COOH-Ph, F), (F, F, 4-COOH-Ph, CF₃), (F, F, 4-COOH-Ph, Br), (F, F, 4-COOH-Ph, Me), (F, F, Bn, H), (F, F, Bn, Cl), (F, F, Bn, F), (F, F, Bn, CF₃), (F, F, Bn, Br), (F, F, Bn, Me), (F, F, 4-F-Bn, H), (F, F, 4-F-Bn, Cl), (F, F, 4-F-Bn, F), (F, F, 4-F-Bn, CF₃), (F, F, 4-F-Bn, Br), (F, F, 4-F-Bn, Me), (F, F, 2-Py, H), (F, F, 2-Py, Cl), (F, F, 2-Py, F), (F, F, 2-Py, CF₃), (F, F, 2-Py, Br), (F, F, 2-Py, Me), (F, F, 3-Py, H), (F, F, 3-Py, Cl), (F, F, 3-Py, F), (F, F, 3-Py, CF₃), (F, F, 3-Py, Br), (F, F, 3-Py, Me), (F, F, 4-Py, H), (F, F, 4-Py, Cl), (F, F, 4-Py, F), (F, F, 4-Py, CF₃), (F, F, 4-Py, Br), (F, F, 4-Py, Me), (F, F, 2-Th, H), (F, F, 2-Th, Cl), (F, F, 2-Th, F), (F, F, 2-Th, CF₃), (F, F, 2-Th, Br), (F, F, 2-Th, Me), (F, F, 3-Th, H), (F, F, 3-Th, Cl), (F, F, 3-Th, F), (F, F, 3-Th, CF₃), (F, F, 3-Th, Br), (F, F, 3-Th, Me), (F, F, Pyrazol-2-yl, H), (F, F, Pyrazol-2-yl, Cl), (F, F, Pyrazol-2-yl, F), (F, F, Pyrazol-2-yl, CF₃), (F, F, Pyrazol-2-yl, Br), (F, F, Pyrazol-2-yl, Me), (F, F, Pyrazol-3-yl, H), (F, F, Pyrazol-3-yl, Cl), (F, F, Pyrazol-3-yl, F), (F, F, Pyrazol-3-yl, CF₃), (F, F, Pyrazol-3-yl, Br), (F, F, Pyrazol-3-yl, Me), (F, F, pyrimidin-2-yl, H), (F, F, pyrimidin-2-yl, Cl), (F, F, pyrimidin-2-yl, F), (F, F, pyrimidin-2-yl, CF₃), (F, F, pyrimidin-2-yl, Br), (F, F, pyrimidin-2-yl, Me), (F, F, pyrimidin-4-yl, H), (F, F, pyrimidin-4-yl, Cl), (F, F, pyrimidin-4-yl, F), (F, F, pyrimidin-4-yl, CF₃), (F, F, pyrimidin-4-yl, Br), (F, F, pyrimidin-4-yl, Me), (F, F, pyrimidin-5-yl, H), (F, F, pyrimidin-5-yl, Cl), (F, F, pyrimidin-5-yl, F), (F, F, pyrimidin-5-yl, CF₃), (F, F, pyrimidin-5-yl, Br), (F, F, pyrimidin-5-yl, Me), (F, F, HOOCCH₂CH₂, H), (F, F, HOOCCH₂CH₂, Cl), (F, F, HOOCCH₂CH₂, F), (F, F, HOOCCH₂CH₂, CF₃), (F., F, HOOCCH₂CH₂CH₂, Br), (F, F, HOOCCH₂CH₂CH₂, Me), (F, F, HOOCCH₂CH₂CH₂CH₂, H), (F, F, HOOCCH₂CH₂CH₂CH₂, Cl), (F, F, HOOCCH₂CH₂CH₂CH₂, F), (F, F, HOOCCH₂CH₂CH₂CH₂, CF₃), (F, F, HOOCCH₂CH₂CH₂CH₂, Br), (F, F, HOOCCH₂CH₂CH₂CH₂, Me), (F, F, (Me)₂NCOCH₂CH₂CH₂, H), (F, F, (Me)₂NCOCH₂CH₂CH₂, Cl), (F, F, (Me)₂NCOCH₂CH₂CH₂, F), (F, F, (Me)₂NCOCH₂CH₂CH₂, CF₃), (F, F, (Me)₂NCOCH₂CH₂CH₂, Br), (F, F, (Me)₂NCOCH₂CH₂CH₂, Me), (F, F, (Me)₂NCOCH₂CH₂CH₂CH₂, H), (F, F, (Me)₂NCOCH₂CH₂CH₂CH₂, Cl), (F, F, (Me)₂NCOCH₂CH₂CH₂CH₂, F), (F, F, (Me)₂NCOCH₂CH₂CH₂CH₂, CF₃), (F, F, (Me)₂NCOCH₂CH₂CH₂CH₂, Br), (F, F, (Me)₂NCOCH₂CH₂CH₂CH₂, Me), (F, F, MeOCH₂, H), (F, F, MeOCH₂, Cl), (F, F, MeOCH₂, F), (F, F, MeOCH₂, CF₃), (F, F, MeOCH₂, Br), (F, F, MeOCH₂, Me), (F, F, EtOCH₂, H), (F, F, EtOCH₂, Cl), (F, F, EtOCH₂, F), (F, F, EtOCH₂, CF₃), (F, F, EtOCH₂, Br), (F, F, EtOCH₂, Me), (F, F, EtOCH₂CH₂, H), (F, F, EtOCH₂CH₂, Cl), (F, F, EtOCH₂CH₂, F), (F, F, EtOCH₂CH₂, CF₃), (F, F, EtOCH₂CH₂, Br), (F, F, EtOCH₂CH₂, Me), (F, F, MeOCH₂CH₂OCH₂CH₂, H), (F, F, MeOCH₂CH₂OCH₂CH₂, Cl), (F, F, MeOCH₂CH₂OCH₂CH₂, F), (F, F, MeOCH₂CH₂OCH₂CH₂, CF₃), (F, F, MeOCH₂CH₂OCH₂CH₂, Br), (F, F, MeOCH₂CH₂OCH₂CH₂, Me), (F, F, MeOCH₂CH₂, H), (F, F, MeOCH₂CH₂, Cl), (F, F, MeOCH₂CH₂, F), (F, F, MeOCH₂CH₂, CF₃), (F, F, MeOCH₂CH₂, Br), (F, F, MeOCH₂CH₂, Me), (F, F, HOCH₂, H), (F, F, HOCH₂, Cl), (F, F, HOCH₂, F), (F, F, HOCH₂, CF₃), (F, F, HOCH₂, Br), (F, F, HOCH₂, Me), (F, F, HOCH₂CH₂, H), (F, F, HOCH₂CH₂, Cl), (F, F, HOCH₂CH₂, F), (F, F, HOCH₂CH₂, CF₃), (F, F, HOCH₂CH₂, Br), (F, F, HOCH₂CH₂, Me), (F, F, HOCH₂CH₂CH₂, H), (F, F, HOCH₂CH₂CH₂, Cl), (F, F, HOCH₂CH₂CH₂, F), (F, F, HOCH₂CH₂CH₂, CF₃), (F, F, HOCH₂CH₂CH₂, Br), (F, F, HOCH₂CH₂CH₂, Me), (F, F, HOCH₂CH₂CH₂CH₂, H), (F, F, HOCH₂CH₂CH₂CH₂, Cl), (F, F, HOCH₂CH₂CH₂CH₂, F), (F, F, HOCH₂CH₂CH₂CH₂, CF₃), (F, F, HOCH₂CH₂CH₂CH₂, Br), (F, F, HOCH₂CH₂CH₂CH₂, Me), (F, F, HOCH₂CH₂CH₂CH₂CH₂, H), (F, F, HOCH₂CH₂CH₂CH₂CH₂, Cl), (F, F, HOCH₂CH₂CH₂CH₂CH₂, F), (F, F, HOCH₂CH₂CH₂CH₂CH₂, CF₃), (F, F, HOCH₂CH₂CH₂CH₂CH₂, Br), (F, F, HOCH₂CH₂CH₂CH₂CH₂, Me), (F, F, HOCH₂CH₂OCH₂CH₂, H), (F, F, HOCH₂CH₂OCH₂CH₂, Cl), (F, F, HOCH₂CH₂OCH₂CH₂, F), (F, F, HOCH₂CH₂OCH₂CH₂, CF₃), (F, F, HOCH₂CH₂OCH₂CH₂, Br), (F, F, HOCH₂CH₂OCH₂CH₂, Me), (F, F, (Me)₂N, H), (F, F, (Me)₂N, Cl), (F, F, (Me)₂N, F), (F, F, (Me)₂N, CF₃), (F, F, (Me)₂N, Br), (F, F, (Me)₂N, Me), (F, F, piperidin-4-yl-methyl, H), (F, F, piperidin-4-yl-methyl, Cl), (F, F, piperidin-4-yl-methyl, F), (F, F, piperidin-4-yl-methyl, CF₃), (F, F, piperidin-4-yl-methyl, Br), (F, F, piperidin-4-yl-methyl, Me), (F, F, cyclohexylmethyl, H), (F, F, cyclohexylmethyl, Cl), (F, F, cyclohexylmethyl, F), (F, F, cyclohexylmethyl, CF₃), (F, F, cyclohexylmethyl, Br), (F, F, cyclohexylmethyl, Me), (F, Cl, H, H), (F, Cl, H, Cl), (F, Cl, H, F), (F, Cl, H, CF₃), (F, Cl, H, Br), (F, Cl, H, Me), (F, Cl, F, H), (F, Cl, F, Cl), (F, Cl, F, F), (F, Cl, F, CF₃), (F, Cl, F, Br), (F, Cl, F, Me), (F, Cl, Cl, H), (F, Cl, Cl, Cl), (F, Cl, Cl, F), (F, Cl, Cl, CF₃), (F, Cl, Cl, Br), (F, Cl, Cl, Me), (F, Cl, Me, H), (F, Cl, Me, Cl), (F, Cl, Me, F), (F, Cl, Me, CF₃), (F, Cl, Me, Br), (F, Cl, Me, Me), (F, Cl, Et, H), (F, Cl, Et, Cl), (F, Cl, Et, F), (F, Cl, Et, CF₃), (F, Cl, Et, Br), (F, Cl, Et, Me), (F, Cl, n-Pr, H), (F, Cl, n-Pr, Cl), (F, Cl, n-Pr, F), (F, Cl, n-Pr, CF₃), (F, Cl, n-Pr, Br), (F, Cl, n-Pr, Me), (F, Cl, c-Pr, H), (F, Cl, c-Pr, Cl), (F, Cl, c-Pr, F), (F, Cl, c-Pr, CF₃), (F, Cl, c-Pr, Br), (F, Cl, c-Pr, Me), (F, Cl, i-Pr, H), (F, Cl, i-Pr, Cl), (F, Cl, i-Pr, F), (F, Cl, i-Pr, CF₃), (F, Cl, i-Pr, Br), (F, Cl, i-Pr, Me), (F, Cl, n-Bu, H), (F, Cl, n-Bu, Cl), (F, Cl, n-Bu, F), (F, Cl, n-Bu, CF₃), (F, Cl, n-Bu, Br), (F, Cl, n-Bu, Me), (F, Cl, i-Bu, H), (F, Cl, i-Bu, Cl), (F, Cl, i-Bu, F), (F, Cl, i-Bu, CF₃), (F, Cl, i-Bu, Br), (F, Cl, i-Bu, Me), (F, Cl, sec-Bu, H), (F, Cl, sec-Bu, Cl), (F, Cl, sec-Bu, F), (F, Cl, sec-Bu, CF₃), (F, Cl, sec-Bu, Br), (F, Cl, sec-Bu, Me), (F, Cl, n-Pen, H), (F, Cl, n-Pen, Cl), (F, Cl, n-Pen, F), (F, Cl, n-Pen, CF₃), (F, Cl, n-Pen, Br), (F, Cl, n-Pen, Me), (F, Cl, c-Pen, H), (F, Cl, c-Pen, Cl), (F, Cl, c-Pen, F), (F, Cl, c-Pen, CF₃), (F, Cl, c-Pen, Br), (F, Cl, c-Pen, Me), (F, Cl, n-Hex, H), (F, Cl, n-Hex, Cl), (F, Cl, n-Hex, F), (F, Cl, n-Hex, CF₃), (F, Cl, n-Hex, Br), (F, Cl, n-Hex, Me), (F, Cl, c-Hex, H), (F, Cl, c-Hex, Cl), (F, Cl, c-Hex, F), (F, Cl, c-Hex, CF₃), (F, Cl, c-Hex, Br), (F, Cl, c-Hex, Me), (F, Cl, OH, H), (F, Cl, OH, Cl), (F, Cl, OH, F), (F, Cl, OH, CF₃), (F, Cl, OH, Br), (F, Cl, OH, Me), (F, Cl, MeO, H), (F, Cl, MeO, Cl), (F, Cl, MeO, F), (F, Cl, MeO, CF₃), (F, Cl, MeO, Br), (F, Cl, MeO, Me), (F, Cl, EtO, H), (F, Cl, EtO, Cl), (F, Cl, EtO, F), (F, Cl, EtO, CF₃), (F, Cl, EtO, Br), (F, Cl, EtO, Me), (F, Cl, n-PrO, H), (F, Cl, n-PrO, Cl), (F, Cl, n-PrO, F), (F, Cl, n-PrO, CF₃), (F, Cl, n-PrO, Br), (F, Cl, n-PrO, Me), (F, Cl, PhO, H), (F, Cl, PhO, Cl), (F, Cl, PhO, F), (F, Cl, PhO, CF₃), (F, Cl, PhO, Br), (F, Cl, PhO, Me), (F, Cl, BnO, H), (F, Cl, BnO, Cl), (F, Cl, BnO, F), (F, Cl, BnO, CF₃), (F, Cl, BnO, Br), (F, Cl, BnO, Me), (F, Cl, PhCH₂CH₂O, H), (F, Cl, PhCH₂CH₂O, Cl), (F, Cl, PhCH₂CH₂O, F), (F, Cl, PhCH₂CH₂O, CF₃), (F, Cl, PhCH₂CH₂O, Br), (F, Cl, PhCH₂CH₂O, Me), (F, Cl, CF₃, H), (F, Cl, CF₃, Cl), (F, Cl, CF₃, F), (F, Cl, CF₃, CF₃), (F, Cl, CF₃, Br), (F, Cl, CF₃, Me), (F, Cl, CF₃O, H), (F, Cl, CF₃O, Cl), (F, Cl, CF₃O, F), (F, Cl, CF₃O, CF₃), (F, Cl, CF₃O, Br), (F, Cl, CF₃O, Me), (F, Cl, Ph, H), (F, Cl, Ph, Cl), (F, Cl, Ph, F), (F, Cl, Ph, CF₃), (F, Cl, Ph, Br), (F, Cl, Ph, Me), (F, Cl, 4-F-Ph, H), (F, Cl, 4-F-Ph, Cl), (F, Cl, 4-F-Ph, F), (F, Cl, 4-F-Ph, CF₃), (F, Cl, 4-F-Ph, Br), (F, Cl, 4-F-Ph, Me), (F, Cl, 4-CF₃-Ph, H), (F, Cl, 4-CF₃-Ph, Cl), (F, Cl, 4-CF₃-Ph, F), (F, Cl, 4-CF₃-Ph, CF₃), (F, Cl, 4-CF₃-Ph, Br), (F, Cl, 4-CF₃-Ph, Me), (F, Cl, 4-(Me)₂N-Ph, H), (F, Cl, 4-(Me)₂N-Ph, Cl), (F, Cl, 4-(Me)₂N-Ph, F), (F, Cl, 4-(Me)₂N-Ph, CF₃), (F, Cl, 4-(Me)₂N-Ph, Br), (F, Cl, 4-(Me)₂N-Ph, Me), (F, Cl, 4-OH-Ph, H), (F, Cl, 4-OH-Ph, Cl), (F, Cl, 4-OH-Ph, F), (F, Cl, 4-OH-Ph, CF₃), (F, Cl, 4-OH-Ph, Br), (F, Cl, 4-OH-Ph, Me), (F, Cl, 3,4-di-F-Ph, H), (F, Cl, 3,4-di-F-Ph, Cl), (F, Cl, 3,4-di-F-Ph, F), (F, Cl, 3,4-di-F-Ph, CF₃), (F, Cl, 3,4-di-F-Ph, Br), (F, Cl, 3,4-di-F-Ph, Me), (F, Cl, 4-COOH-Ph, H), (F., Cl, 4-COOH-Ph, Cl), (F, Cl, 4-COOH-Ph, F), (F, Cl, 4-COOH-Ph, CF₃), (F, Cl, 4-COOH-Ph, Br), (F, Cl, 4-COOH-Ph, Me), (F, Cl, Bn, H), (F, Cl, Bn, Cl), (F, Cl, Bn, F), (F, Cl, Bn, CF₃), (F, Cl, Bn, Br), (F, Cl, Bn, Me), (F, Cl, 4-F-Bn, H), (F, Cl, 4-F-Bn, Cl), (F, Cl, 4-F-Bn, F), (F, Cl, 4-F-Bn, CF₃), (F, Cl, 4-F-Bn, Br), (F, Cl, 4-F-Bn, Me), (F, Cl, 2-Py, H), (F, Cl, 2-Py, Cl), (F, Cl, 2-Py, F), (F, Cl, 2-Py, CF₃), (F, Cl, 2-Py, Br), (F, Cl, 2-Py, Me), (F, Cl, 3-Py, H), (F, Cl, 3-Py, Cl), (F, Cl, 3-Py, F), (F, Cl, 3-Py, CF₃), (F, Cl, 3-Py, Br), (F, Cl, 3-Py, Me), (F, Cl, 4-Py, H), (F, Cl, 4-Py, Cl), (F, Cl, 4-Py, F), (F, Cl, 4-Py, CF₃), (F, Cl, 4-Py, Br), (F, Cl, 4-Py, Me), (F, Cl, 2-Th, H), (F, Cl, 2-Th, Cl), (F, Cl, 2-Th, F), (F, Cl, 2-Th, CF₃), (F, Cl, 2-Th, Br), (F, Cl, 2-Th, Me), (F, Cl, 3-Th, H), (F, Cl, 3-Th, Cl), (F, Cl, 3-Th, F), (F, Cl, 3-Th, CF₃), (F, Cl, 3-Th, Br), (F, Cl, 3-Th, Me), (F, Cl, Pyrazol-2-yl, H), (F, Cl, Pyrazol-2-yl, Cl), (F, Cl, Pyrazol-2-yl, F), (F, Cl, Pyrazol-2-yl, CF₃), (F, Cl, Pyrazol-2-yl, Br), (F, Cl, Pyrazol-2-yl, Me), (F, Cl, Pyrazol-3-yl, H), (F, Cl, Pyrazol-3-yl, Cl), (F, Cl, Pyrazol-3-yl, F), (F, Cl, Pyrazol-3-yl, CF₃), (F, Cl, Pyrazol-3-yl, Br), (F, Cl, Pyrazol-3-yl, Me), (F, Cl, pyrimidin-2-yl, H), (F, Cl, pyrimidin-2-yl, Cl), (F, Cl, pyrimidin-2-yl, F), (F, Cl, pyrimidin-2-yl, CF₃), (F, Cl, pyrimidin-2-yl, Br), (F, Cl, pyrimidin-2-yl, Me), (F, Cl, pyrimidin-4-yl, H), (F, Cl, pyrimidin-4-yl, Cl), (F, Cl, pyrimidin-4-yl, F), (F, Cl, pyrimidin-4-yl, CF₃), (F, Cl, pyrimidin-4-yl, Br), (F, Cl, pyrimidin-4-yl, Me), (F, Cl, pyrimidin-5-yl, H), (F, Cl, pyrimidin-5-yl, Cl), (F, Cl, pyrimidin-5-yl, F), (F, Cl, pyrimidin-5-yl, CF₃), (F, Cl, pyrimidin-5-yl, Br), (F, Cl, pyrimidin-5-yl, Me), (F, Cl, HOOCCH₂CH₂CH₂, H), (F, Cl, HOOCCH₂CH₂CH₂, Cl), (F, Cl, HOOCCH₂CH₂CH₂, F), (F, Cl, HOOCCH₂CH₂CH₂, CF₃), (F, Cl, HOOCCH₂CH₂CH₂, Br), (F, Cl, HOOCCH₂CH₂CH₂, Me), (F, Cl, HOOCCH₂CH₂CH₂CH₂, H), (F, Cl, HOOCCH₂CH₂CH₂CH₂, Cl), (F, Cl, HOOCCH₂CH₂CH₂CH₂, F), (F, Cl, HOOCCH₂CH₂CH₂CH₂, CF₃), (F, Cl, HOOCCH₂CH₂CH₂CH₂, Br), (F, Cl, HOOCCH₂CH₂CH₂CH₂, Me), (F, Cl, (Me)₂NCOCH₂CH₂CH₂, H), (F, Cl, (Me)₂NCOCH₂CH₂CH₂, Cl), (F, Cl, (Me)₂NCOCH₂CH₂CH₂, F), (F, Cl, (Me)₂NCOCH₂CH₂CH₂, CF₃), (F, Cl, (Me)₂NCOCH₂CH₂CH₂, Br), (F, Cl, (Me)₂NCOCH₂CH₂CH₂, Me), (F, Cl, (Me)₂NCOCH₂CH₂CH₂CH₂, H), (F, Cl, (Me)₂NCOCH₂CH₂CH₂CH₂, Cl), (F, Cl, (Me)₂NCOCH₂CH₂CH₂CH₂, F), (F, Cl, (Me)₂NCOCH₂CH₂CH₂CH₂, CF₃), (F, Cl, (Me)₂NCOCH₂CH₂CH₂CH₂, Br), (F, Cl, (Me)₂NCOCH₂CH₂CH₂CH₂, Me), (F, Cl, MeOCH₂, H), (F, Cl, MeOCH₂, Cl), (F, Cl, MeOCH₂, F), (F, Cl, MeOCH₂, CF₃), (F, Cl, MeOCH₂, Br), (F, Cl, MeOCH₂, Me), (F, Cl, EtOCH₂, H), (F, Cl, EtOCH₂, Cl), (F, Cl, EtOCH₂, F), (F, Cl, EtOCH₂, CF₃), (F, Cl, EtOCH₂, Br), (F, Cl, EtOCH₂, Me), (F, Cl, EtOCH₂CH₂, H), (F, Cl, EtOCH₂CH₂, Cl), (F, Cl, EtOCH₂CH₂, F), (F, Cl, EtOCH₂CH₂, CF₃), (F, Cl, EtOCH₂CH₂, Br), (F, Cl, EtOCH₂CH₂, Me), (F, Cl, MeOCH₂CH₂OCH₂CH₂, H), (F, Cl, MeOCH₂CH₂OCH₂CH₂, Cl), (F, Cl, MeOCH₂CH₂OCH₂CH₂, F), (F, Cl, MeOCH₂CH₂OCH₂CH₂, CF₃), (F, Cl, MeOCH₂CH₂OCH₂CH₂, Br), (F, Cl, MeOCH₂CH₂OCH₂CH₂, Me), (F, Cl, MeOCH₂CH₂, H), (F, Cl, MeOCH₂CH₂, Cl), (F, Cl, MeOCH₂CH₂, F), (F, Cl, MeOCH₂CH₂, CF₃), (F, Cl, MeOCH₂CH₂, Br), (F, Cl, MeOCH₂CH₂, Me), (F, Cl, HOCH₂, H), (F, Cl, HOCH₂, Cl), (F, Cl, HOCH₂, F), (F, Cl, HOCH₂, CF₃), (F, Cl, HOCH₂, Br), (F, Cl, HOCH₂, Me), (F, Cl, HOCH₂CH₂, H), (F, Cl, HOCH₂CH₂, Cl), (F, Cl, HOCH₂CH₂, F), (F, Cl, HOCH₂CH₂, CF₃), (F, Cl, HOCH₂CH₂, Br), (F, Cl, HOCH₂CH₂, Me), (F, Cl, HOCH₂CH₂CH₂, H), (F, Cl, HOCH₂CH₂CH₂, Cl), (F, Cl, HOCH₂CH₂CH₂, F), (F, Cl, HOCH₂CH₂CH₂, CF₃), (F, Cl, HOCH₂CH₂CH₂, Br), (F, Cl, HOCH₂CH₂CH₂, Me), (F, Cl, HOCH₂CH₂CH₂CH₂, H), (F, Cl, HOCH₂CH₂CH₂CH₂, Cl), (F, Cl, HOCH₂CH₂CH₂CH₂, F), (F, Cl, HOCH₂CH₂CH₂CH₂, CF₃), (F, Cl, HOCH₂CH₂CH₂CH₂, Br), (F, Cl, HOCH₂CH₂CH₂CH₂, Me), (F, Cl, HOCH₂CH₂CH₂CH₂CH₂, H), (F, Cl, HOCH₂CH₂CH₂CH₂CH₂, Cl), (F, Cl, HOCH₂CH₂CH₂CH₂CH₂, F), (F, Cl, HOCH₂CH₂CH₂CH₂CH₂, CF₃), (F, Cl, HOCH₂CH₂CH₂CH₂CH₂, Br), (F, Cl, HOCH₂CH₂CH₂CH₂CH₂, Me), (F, Cl, HOCH₂CH₂OCH₂CH₂, H), (F, Cl, HOCH₂CH₂OCH₂CH₂, Cl), (F, Cl, HOCH₂CH₂OCH₂CH₂, F), (F, Cl, HOCH₂CH₂OCH₂CH₂, CF₃), (F, Cl, HOCH₂CH₂OCH₂CH₂, Br), (F, Cl, HOCH₂CH₂OCH₂CH₂, Me), (F, Cl, (Me)₂N, H), (F, Cl, (Me)₂N, Cl), (F, Cl, (Me)₂N, F), (F, Cl, (Me)₂N, CF₃), (F, Cl, (Me)₂N, Br), (F, Cl, (Me)₂N, Me), (F, Cl, piperidin-4-yl-methyl, H), (F, Cl, piperidin-4-yl-methyl, Cl), (F, Cl, piperidin-4-yl-methyl, F), (F, Cl, piperidin-4-yl-methyl, CF₃), (F, Cl, piperidin-4-yl-methyl, Br), (F, Cl, piperidin-4-yl-methyl, Me), (F, Cl, cyclohexylmethyl, H), (F, Cl, cyclohexylmethyl, Cl), (F, Cl, cyclohexylmethyl, F), (F, Cl, cyclohexylmethyl, CF₃), (F, Cl, cyclohexylmethyl, Br), (F, Cl, cyclohexylmethyl, Me), (Me, H, H, H), (Me, H, H, Cl), (Me, H, H, F), (Me, H, H, CF₃), (Me, H, H, Br), (Me, H, H, Me), (Me, H, F, H), (Me, H, F, Cl), (Me, H, F, F), (Me, H, F, CF₃), (Me, H, F, Br), (Me, H, F, Me), (Me, H, Cl, H), (Me, H, Cl, Cl), (Me, H, Cl, F), (Me, H, Cl, CF₃), (Me, H, Cl, Br), (Me, H, Cl, Me), (Me, H, Me, H), (Me, H, Me, Cl), (Me, H, Me, F), (Me, H, Me, CF₃), (Me, H, Me, Br), (Me, H, Me, Me), (Me, H, Et, H), (Me, H, Et, Cl), (Me, H, Et, F), (Me, H, Et, CF₃), (Me, H, Et, Br), (Me, H, Et, Me), (Me, H, n-Pr, H), (Me, H, n-Pr, Cl), (Me, H, n-Pr, F), (Me, H, n-Pr, CF₃), (Me, H, n-Pr, Br), (Me, H, n-Pr, Me), (Me, H, c-Pr, H), (Me, H, c-Pr, Cl), (Me, H, c-Pr, F), (Me, H, c-Pr, CF₃), (Me, H, c-Pr, Br), (Me, H, c-Pr, Me), (Me, H, i-Pr, H), (Me, H, i-Pr, Cl), (Me, H, i-Pr, F), (Me, H, i-Pr, CF₃), (Me, H, i-Pr, Br), (Me, H, i-Pr, Me), (Me, H, n-Bu, H), (Me, H, n-Bu, Cl), (Me, H, n-Bu, F), (Me, H, n-Bu, CF₃), (Me, H, n-Bu, Br), (Me, H, n-Bu, Me), (Me, H, i-Bu, H), (Me, H, i-Bu, Cl), (Me, H, i-Bu, F), (Me, H, i-Bu, CF₃), (Me, H, i-Bu, Br), (Me, H, i-Bu, Me), (Me, H, sec-Bu, H), (Me, H, sec-Bu, Cl), (Me, H, sec-Bu, F), (Me, H, sec-Bu, CF₃), (Me, H, sec-Bu, Br), (Me, H, sec-Bu, Me), (Me, H, n-Pen, H), (Me, H, n-Pen, Cl), (Me, H, n-Pen, F), (Me, H, n-Pen, CF₃), (Me, H, n-Pen, Br), (Me, H, n-Pen, Me), (Me, H, c-Pen, H), (Me, H, c-Pen, Cl), (Me, H, c-Pen, F), (Me, H, c-Pen, CF₃), (Me, H, c-Pen, Br), (Me, H, c-Pen, Me), (Me, H, n-Hex, H), (Me, H, n-Hex, Cl), (Me, H, n-Hex, F), (Me, H, n-Hex, CF₃), (Me, H, n-Hex, Br), (Me, H, n-Hex, Me), (Me, H, c-Hex, H), (Me, H, c-Hex, Cl), (Me, H, c-Hex, F), (Me, H, c-Hex, CF₃), (Me, H, c-Hex, Br), (Me, H, c-Hex, Me), (Me, H, OH, H), (Me, H, OH, Cl), (Me, H, OH, F), (Me, H, OH, CF₃), (Me, H, OH, Br), (Me, H, OH, Me), (Me, H, MeO, H), (Me, H, MeO, Cl), (Me, H, MeO, F), (Me, H, MeO, CF₃), (Me, H, MeO, Br), (Me, H, MeO, Me), (Me, H, EtO, H), (Me, H, EtO, Cl), (Me, H, EtO, F), (Me, H, EtO, CF₃), (Me, H, EtO, Br), (Me, H, EtO, Me), (Me, H, n-PrO, H), (Me, H, n-PrO, Cl), (Me, H, n-PrO, F), (Me, H, n-PrO, CF₃), (Me, H, n-PrO, Br), (Me, H, n-PrO, Me), (Me, H, PhO, H), (Me, H, PhO, Cl), (Me, H, PhO, F), (Me, H, PhO, CF₃), (Me, H, PhO, Br), (Me, H, PhO, Me), (Me, H, BnO, H), (Me, H, BnO, Cl), (Me, H, BnO, F), (Me, H, BnO, CF₃), (Me, H, BnO, Br), (Me, H, BnO, Me), (Me, H, PhCH₂CH₂O, H), (Me, H, PhCH₂CH₂O, Cl), (Me, H, PhCH₂CH₂O, F), (Me, H, PhCH₂CH₂O, CF₃), (Me, H, PhCH₂CH₂O, Br), (Me, H, PhCH₂CH₂O, Me), (Me, H, CF₃, H), (Me, H, CF₃, Cl), (Me, H, CF₃, F), (Me, H, CF₃, CF₃), (Me, H, CF₃, Br), (Me, H, CF₃, Me), (Me, H, CF₃O, H), (Me, H, CF₃O, Cl), (Me, H, CF₃O, F), (Me, H, CF₃O, CF₃), (Me, H, CF₃O, Br), (Me, H, CF₃O, Me), (Me, H, Ph, H), (Me, H, Ph, Cl), (Me, H, Ph, F), (Me, H, Ph, CF₃), (Me, H, Ph, Br), (Me, H, Ph, Me), (Me, H, 4-F-Ph, H), (Me, H, 4-F-Ph, Cl), (Me, H, 4-F-Ph, F), (Me, H, 4-F-Ph, CF₃), (Me, H, 4-F-Ph, Br), (Me, H, 4-F-Ph, Me), (Me, H, 4-CF₃-Ph, H), (Me, H, 4-CF₃-Ph, Cl), (Me, H, 4-CF₃-Ph, F), (Me, H, 4-CF₃-Ph, CF₃), (Me, H, 4-CF₃-Ph, Br), (Me, H, 4-CF₃-Ph, Me), (Me, H, 4-(Me)₂N-Ph, H), (Me, H, 4-(Me)₂N-Ph, Cl), (Me, H, 4-(Me)₂N-Ph, F), (Me, H, 4(Me)₂N-Ph, CF₃), (Me, H, 4-(Me)₂N-Ph, Br), (Me, H. 4-(Me)₂N-Ph, Me), (Me, H, 4-OH-Ph, H), (Me, H, 4-OH-Ph, Cl), (Me, H, 4-OH-Ph, F), (Me, H, 4-OH-Ph, CF₃), (Me, H, 4-OH-Ph, Br), (Me, H, 4-OH-Ph, Me), (Me, H, 3,4-di-F-Ph, H), (Me, H, 3,4-di-F-Ph, Cl), (Me, H, 3,4-di-F-Ph, F), (Me, H, 3,4-di-F-Ph, CF₃), (Me, H, 3,4-di-F-Ph, Br), (Me, H, 3,4-di-F-Ph, Me), (Me, H, 4-COOH-Ph, H), (Me, H, 4-COOH-Ph, Cl), (Me, H, 4-COOH-Ph, F), (Me, H, 4-COOH-Ph, CF₃), (Me, H, 4-COOH-Ph, Br), (Me, H, 4-COOH-Ph, Me), (Me, H, Bn, H), (Me, H, Bn, Cl), (Me, H, Bn, F), (Me, H, Bn, CF₃), (Me, H, Bn, Br), (Me, H, Bn, Me), (Me, H, 4-F-Bn, H), (Me, H, 4-F-Bn, Cl), (Me, H, 4-F-Bn, F), (Me, H, 4-F-Bn, CF₃), (Me, H, 4-F-Bn, Br), (Me, H, 4-F-Bn, Me), (Me, H, 2-Py, H), (Me, H, 2-Py, Cl), (Me, H, 2-Py, F), (Me, H, 2-Py, CF₃), (Me, H, 2-Py, Br), (Me, H, 2-Py, Me), (Me, H, 3-Py, H), (Me, H, 3-Py, Cl), (Me, H, 3-Py, F), (Me, H, 3-Py, CF₃), (Me, H, 3-Py, Br), (Me, H, 3-Py, Me), (Me, H, 4-Py, H), (Me, H, 4-Py, Cl), (Me, H, 4-Py, F), (Me, H, 4-Py, CF₃), (Me, H, 4-Py, Br), (Me, H, 4-Py, Me), (Me, H, 2-Th, H), (Me, H, 2-Th, Cl), (Me, H, 2-Th, F), (Me, H, 2-Th, CF₃), (Me, H, 2-Th, Br), (Me, H, 2-Th, Me), (Me, H, 3-Th, H), (Me, H, 3-Th, Cl), (Me, H, 3-Th, F), (Me, H, 3-Th, CF₃), (Me, H, 3-Th, Br), (Me, H, 3-Th, Me), (Me, H, Pyrazol-2-yl, H), (Me, H, Pyrazol-2-yl, Cl), (Me, H, Pyrazol-2-yl, F), (Me, H, Pyrazol-2-yl, CF₃), (Me, H, Pyrazol-2-yl, Br), (Me, H, Pyrazol-2-yl, Me), (Me, H, Pyrazol-3-yl, H), (Me, H, Pyrazol-3-yl, Cl), (Me, H, Pyrazol-3-yl, F), (Me, H, Pyrazol-3-yl, CF₃), (Me, H, Pyrazol-3-yl, Br), (Me, H, Pyrazol-3-yl, Me), (Me, H, pyrimidin-2-yl, H), (Me, H, pyrimidin-2-yl, Cl), (Me, H, pyrimidin-2-yl, F), (Me, H, pyrimidin-2-yl, CF₃), (Me, H, pyrimidin-2-yl, Br), (Me, H, pyrimidin-2-yl, Me), (Me, H, pyrimidin-4-yl, H), (Me, H, pyrimidin-4-yl, Cl), (Me, H, pyrimidin-4-yl, F), (Me, H, pyrimidin-4-yl, CF₃), (Me, H, pyrimidin-4-yl, Br), (Me, H, pyrimidin-4-yl, Me), (Me, H, pyrimidin-5-yl, H), (Me, H, pyrimidin-5-yl, Cl), (Me, H, pyrimidin-5-yl, F), (Me, H, pyrimidin-5-yl, CF₃), (Me, H, pyrimidin-5-yl, Br), (Me, H, pyrimidin-5-yl, Me), (Me, H, HOOCCH₂CH₂CH₂, H), (Me, H, HOOCCH₂CH₂CH₂, Cl), (Me, H, HOOCCH₂CH₂CH₂, F), (Me, H, HOOCCH₂CH₂CH₂, CF₃), (Me, H, HOOCCH₂CH₂CH₂, Br), (Me, H, HOOCCH₂CH₂CH₂, Me), (Me, H, HOOCCH₂CH₂CH₂CH₂, H), (Me, H, HOOCCH₂CH₂CH₂CH₂, Cl), (Me, H, HOOCCH₂CH₂CH₂CH₂, F), (Me, H, HOOCCH₂CH₂CH₂CH₂, CF₃), (Me, H, HOOCCH₂CH₂CH₂CH₂, Br), (Me, H, HOOCCH₂CH₂CH₂CH₂, Me), (Me, H, (Me)₂NCOCH₂CH₂CH₂, H), (Me, H, (Me)₂NCOCH₂CH₂CH₂, Cl), (Me, H, (Me)₂NCOCH₂CH₂CH₂, F), (Me, H, (Me)₂NCOCH₂CH₂CH₂, CF₃), (Me, H, (Me)₂NCOCH₂CH₂CH₂, Br), (Me, H, (Me)₂NCOCH₂CH₂CH₂, Me), (Me, H, (Me)₂NCOCH₂CH₂CH₂CH₂, H), (Me, H, (Me)₂NCOCH₂CH₂CH₂CH₂, Cl), (Me, H, (Me)₂NCOCH₂CH₂CH₂CH₂, F), (Me, H, (Me)₂NCOCH₂CH₂CH₂CH₂, CF₃), (Me, H, (Me)₂NCOCH₂CH₂CH₂CH₂, Br), (Me, H, (Me)₂NCOCH₂CH₂CH₂CH₂, Me), (Me, H, MeOCH₂, H), (Me, H, MeOCH₂, Cl), (Me, H, MeOCH₂, F), (Me, H, MeOCH₂, CF₃), (Me, H, MeOCH₂, Br), (Me, H, MeOCH₂, Me), (Me, H, EtOCH₂, H), (Me, H, EtOCH₂, Cl), (Me, H, EtOCH₂, F), (Me, H, EtOCH₂, CF₃), (Me, H, EtOCH₂, Br), (Me, H, EtOCH₂, Me), (Me, H, EtOCH₂CH₂, H), (Me, H, EtOCH₂CH₂, Cl), (Me, H, EtOCH₂CH₂, F), (Me, H, EtOCH₂CH₂, CF₃), (Me, H, EtOCH₂CH₂, Br), (Me, H, EtOCH₂CH₂, Me), (Me, H, MeOCH₂CH₂OCH₂CH₂, H), (Me, H, MeOCH₂CH₂OCH₂CH₂, Cl), (Me, H, MeOCH₂CH₂OCH₂CH₂, F), (Me, H, MeOCH₂CH₂OCH₂CH₂, CF₃), (Me, H, MeOCH₂CH₂OCH₂CH₂, Br), (Me, H, MeOCH₂CH₂OCH₂CH₂, Me), (Me, H, MeOCH₂CH₂, H), (Me, H, MeOCH₂CH₂, Cl), (Me, H, MeOCH₂CH₂, F), (Me, H, MeOCH₂CH₂, CF₃), (Me, H, MeOCH₂CH₂, Br), (Me, H, MeOCH₂CH₂, Me), (Me, H, HOCH₂, H), (Me, H, HOCH₂, Cl), (Me, H, HOCH₂, F), (Me, H, HOCH₂, CF₃), (Me, H, HOCH₂, Br), (Me, H, HOCH₂, Me), (Me, H, HOCH₂CH₂, H), (Me, H, HOCH₂CH₂, Cl), (Me, H, HOCH₂CH₂, F), (Me, H, HOCH₂CH₂, CF₃), (Me, H, HOCH₂CH₂, Br), (Me, H, HOCH₂CH₂, Me); (Me, H, HOCH₂CH₂CH₂, H), (Me, H, HOCH₂CH₂CH₂, Cl), (Me, H, HOCH₂CH₂CH₂, F), (Me, H, HOCH₂CH₂CH₂, CF₃), (Me, H, HOCH₂CH₂CH₂, Br), (Me, H, HOCH₂CH₂CH₂, Me), (Me, H, HOCH₂CH₂CH₂CH₂, H), (Me, H, HOCH₂CH₂CH₂CH₂, Cl), (Me, H, HOCH₂CH₂CH₂CH₂, F), (Me, H, HOCH₂CH₂CH₂CH₂, CF₃), (Me, H, HOCH₂CH₂CH₂CH₂, Br), (Me, H, HOCH₂CH₂CH₂CH₂, Me), (Me, H, HOCH₂CH₂CH₂CH₂CH₂, H), (Me, H, HOCH₂CH₂CH₂CH₂CH₂, Cl), (Me, H, HOCH₂CH₂CH₂CH₂CH₂, F), (Me, H, HOCH₂CH₂CH₂CH₂CH₂, CF₃), (Me, H, HOCH₂CH₂CH₂CH₂CH₂, Br), (Me, H, HOCH₂CH₂CH₂CH₂CH₂, Me), (Me, H, HOCH₂CH₂OCH₂CH₂, H), (Me, H, HOCH₂CH₂OCH₂CH₂, Cl), (Me, H, HOCH₂CH₂OCH₂CH₂, F), (Me, H, HOCH₂CH₂OCH₂CH₂, CF₃), (Me, H, HOCH₂CH₂OCH₂CH₂, Br), (Me, H, HOCH₂CH₂OCH₂CH₂, Me), (Me, H, (Me)₂N, H), (Me, H, (Me)₂N, Cl), (Me, H, (Me)₂N, F), (Me, H, (Me)₂N, CF₃), (Me, H, (Me)₂N, Br), (Me, H, (Me)₂N, Me), (Me, H, piperidin-4-yl-methyl, H), (Me, H, piperidin-4-yl-methyl, Cl), (Me, H, piperidin-4-yl-methyl, F), (Me, H, piperidin-4-yl-methyl, CF₃), (Me, H, piperidin-4-yl-methyl, Br), (Me, H, piperidin-4-yl-methyl, Me), (Me, H, cyclohexylmethyl, H), (Me, H, cyclohexylmethyl, Cl), (Me, H, cyclohexylmethyl, F), (Me, H, cyclohexylmethyl, CF₃), (Me, H, cyclohexylmethyl, Br), (Me, H, cyclohexylmethyl, Me), (Me, F, H, H), (Me, F, H, Cl), (Me, F, H, F), (Me, F, H, CF₃), (Me, F, H, Br), (Me, F, H, Me), (Me, F, F, H), (Me, F, F, Cl), (Me, F, F, F), (Me, F, F, CF₃), (Me, F, F, Br), (Me, F, F, Me), (Me, F, Cl, H), (Me, F, Cl, Cl), (Me, F, Cl, F), (Me, F, Cl, CF₃), (Me, F, Cl, Br), (Me, F, Cl, Me), (Me, F, Me, H), (Me, F, Me, Cl), (Me, F, Me, F), (Me, F, Me, CF₃), (Me, F, Me, Br), (Me, F, Me, Me), (Me, F, Et, H), (Me, F, Et, Cl), (Me, F, Et, F), (Me, F, Et, CF₃), (Me, F, Et, Br), (Me, F, Et, Me), (Me, F, n-Pr, H), (Me, F, n-Pr, Cl), (Me, F, n-Pr, F), (Me, F, n-Pr, CF₃), (Me, F, n-Pr, Br), (Me, F, n-Pr, Me), (Me, F, c-Pr, H), (Me, F, c-Pr, Cl), (Me, F, c-Pr, F), (Me, F, c-Pr, CF₃), (Me, F, c-Pr, Br), (Me, F, c-Pr, Me), (Me, F, i-Pr, H), (Me, F, i-Pr, Cl), (Me, F, i-Pr, F), (Me, F, i-Pr, CF₃), (Me, F, i-Pr, Br), (Me, F, i-Pr, Me), (Me, F, n-Bu, H), (Me, F, n-Bu, Cl), (Me, F, n-Bu, F), (Me, F, n-Bu, CF₃), (Me, F, n-Bu, Br), (Me, F, n-Bu, Me), (Me, F, i-Bu, H), (Me, F, i-Bu, Cl), (Me, F, i-Bu, F), (Me, F, i-Bu, CF₃), (Me, F, i-Bu, Br), (Me, F, i-Bu, Me), (Me, F, sec-Bu, H), (Me, F, sec-Bu, Cl), (Me, F, sec-Bu, F), (Me, F, sec-Bu, CF₃), (Me, F, sec-Bu, Br), (Me, F, sec-Bu, Me), (Me, F, n-Pen, H), (Me, F, n-Pen, Cl), (Me, F, n-Pen, F), (Me, F, n-Pen, CF₃), (Me, F, n-Pen, Br), (Me, F, n-Pen, Me), (Me, F, c-Pen, H), (Me, F, c-Pen, Cl), (Me, F, c-Pen, F), (Me, F, c-Pen, CF₃), (Me, F, c-Pen, Br), (Me, F, c-Pen, Me), (Me, F, n-Hex, H), (Me, F, n-Hex, Cl), (Me, F, n-Hex, F), (Me, F, n-Hex, CF₃), (Me, F, n-Hex, Br), (Me, F, n-Hex, Me), (Me, F, c-Hex, H), (Me, F, c-Hex, Cl), (Me, F, c-Hex, F), (Me, F, c-Hex, CF₃), (Me, F, c-Hex, Br), (Me, F, c-Hex, Me), (Me, F, OH, H), (Me, F, OH, Cl), (Me, F, OH, F), (Me, F, OH, CF₃), (Me, F, OH, Br), (Me, F, OH, Me), (Me, F, MeO, H), (Me, F, MeO, Cl), (Me, F, MeO, F), (Me, F, MeO, CF₃), (Me, F, MeO, Br), (Me, F, MeO, Me), (Me, F, EtO, H), (Me, F, EtO, Cl), (Me, F, EtO, F), (Me, F, EtO, CF₃), (Me, F, EtO, Br), (Me, F, EtO, Me), (Me, F, n-PrO, H), (Me, F, n-PrO, Cl), (Me, F, n-PrO, F), (Me, F, n-PrO, CF₃), (Me, F, n-PrO, Br), (Me, F, n-PrO, Me), (Me, F, PhO, H), (Me, F, PhO, Cl), (Me, F, PhO, F), (Me, F, PhO, CF₃), (Me, F, PhO, Br), (Me, F, PhO, Me), (Me, F, BnO, H), (Me, F, BnO, Cl), (Me, F, BnO, F), (Me, F, BnO, CF₃), (Me, F, BnO, Br), (Me, F, BnO, Me), (Me, F, PhCH₂CH₂O, H), (Me, F, PhCH₂CH₂O, Cl), (Me, F, PhCH₂CH₂O, F), (Me, F, PhCH₂CH₂O, CF₃), (Me, F, PhCH₂CH₂O, Br), (Me, F, PhCH₂CH₂O, Me), (Me, F, CF₃, H), (Me, F, CF₃, Cl), (Me, F, CF₃, F), (Me, F, CF₃, CF₃), (Me, F, CF₃, Br), (Me, F, CF₃, Me), (Me, F, CF₃O, H), (Me, F, CF₃O, Cl), (Me, F, CF₃₀, F), (Me, F, CF₃O, CF₃), (Me, F, CF₃O, Br), (Me, F, CF₃O, Me), (Me, F, Ph, H), (Me, F, Ph, Cl), (Me, F, Ph, F), (Me, F, Ph, CF₃), (Me, F, Ph, Br), (Me, F, Ph, Me), (Me, F, 4-F-Ph, H), (Me, F, 4-F-Ph, Cl), (Me, F, 4-F-Ph, F), (Me, F, 4-F-Ph, CF₃), (Me, F, 4-F-Ph, Br), (Me, F, 4-F-Ph, Me), (Me, F. 4-CF₃-Ph. H), (Me, F, 4-CF₃-Ph, Cl), (Me, F, 4-CF₃-Ph, F), (Me, F, 4-CF₃-Ph, CF₃), (Me, F, 4-CF₃-Ph, Br), (Me, F, 4-CF₃-Ph, Me), (Me, F, 4-(Me)₂N-Ph, H), (Me, F, 4-(Me)₂N-Ph, Cl), (Me, F, 4-(Me)₂N-Ph, F), (Me, F, 4-(Me)₂N-Ph, CF₃), (Me, F, 4-(Me)₂N-Ph, Br), (Me, F, 4-(Me)₂N-Ph, Me), (Me, F, 4-OH-Ph, H), (Me, F, 4-OH-Ph, Cl), (Me, F, 4-OH-Ph, F), (Me, F, 4-OH-Ph, CF₃), (Me, F, 4-OH-Ph, Br), (Me, F, 4-OH-Ph, Me), (Me, F, 3,4-di-F-Ph, H), (Me, F, 3,4-di-F-Ph, Cl), (Me, F, 3,4-di-F-Ph, F), (Me, F, 3,4-di-F-Ph, CF₃), (Me, F, 3,4-di-F-Ph, Br), (Me, F, 3,4-di-F-Ph, Me), (Me, F, 4-COOH-Ph, H), (Me, F, 4-COOH-Ph, Cl), (Me, F, 4-COOH-Ph, F), (Me, F, 4-COOH-Ph, CF₃), (Me, F, 4-COOH-Ph, Br), (Me, F, 4-COOH-Ph, Me), (Me, F, Bn, H), (Me, F, Bn, Cl), (Me, F, Bn, F), (Me, F, Bn, CF₃), (Me, F, Bn, Br), (Me, F, Bn, Me), (Me, F, 4-F-Bn, H), (Me, F, 4-F-Bn, Cl), (Me, F, 4-F-Bn, F), (Me, F, 4-F-Bn, CF₃), (Me, F, 4-F-Bn, Br), (Me, F, 4-F-Bn, Me), (Me, F, 2-Py, H), (Me, F, 2-Py, Cl), (Me, F, 2-Py, F), (Me, F, 2-Py, CF₃), (Me, F, 2-Py, Br), (Me, F, 2-Py, Me), (Me, F, 3-Py, H), (Me, F, 3-Py, Cl), (Me, F, 3-Py, F), (Me, F, 3-Py, CF₃), (Me, F, 3-Py, Br), (Me, F, 3-Py, Me), (Me, F, 4-Py, H), (Me, F, 4-Py, Cl), (Me, F, 4-Py, F), (Me, F, 4-Py, CF₃), (Me, F, 4-Py, Br), (Me, F, 4-Py, Me), (Me, F, 2-Th, H), (Me, F, 2-Th, Cl), (Me, F, 2-Th, F), (Me, F, 2-Th, CF₃), (Me, F, 2-Th, Br), (Me, F, 2-Th, Me), (Me, F, 3-Th, H), (Me, F, 3-Th, Cl), (Me, F, 3-Th, F), (Me, F, 3-Th, CF₃), (Me, F, 3-Th, Br), (Me, F, 3-Th, Me), (Me, F, Pyrazol-2-yl, H), (Me, F, Pyrazol-2-yl, Cl), (Me, F, Pyrazol-2-yl, F), (Me, F, Pyrazol-2-yl, CF₃), (Me, F, Pyrazol-2-yl, Br), (Me, F, Pyrazol-2-yl, Me), (Me, F, Pyrazol-3-yl, H), (Me, F, Pyrazol-3-yl, Cl), (Me, F, Pyrazol-3-yl, F), (Me, F, Pyrazol-3-yl, CF₃), (Me, F, Pyrazol-3-yl, Br), (Me, F, Pyrazol-3-yl, Me), (Me, F, pyrimidin-2-yl, H), (Me, F, pyrimidin-2-yl, Cl), (Me, F, pyrimidin-2-yl, F), (Me, F, pyrimidin-2-yl, CF₃), (Me, F, pyrimidin-2-yl, Br), (Me, F, pyrimidin-2-yl, Me), (Me, F, pyrimidin-4-yl, H), (Me, F, pyrimidin-4-yl, Cl), (Me, F, pyrimidin-4-yl, F), (Me, F, pyrimidin-4-yl, CF₃), (Me, F, pyrimidin-4-yl, Br), (Me, F, pyrimidin-4-yl, Me), (Me, F, pyrimidin-5-yl, H), (Me, F, pyrimidin-5-yl, Cl), (Me, F, pyrimidin-5-yl, F), (Me, F, pyrimidin-5-yl, CF₃), (Me, F, pyrimidin-5-yl, Br), (Me, F, pyrimidin-5-yl, Me), (Me, F, HOOCCH₂CH₂CH₂, H), (Me, F, HOOCCH₂CH₂CH₂, Cl), (Me, F, HOOCCH₂CH₂CH₂, F), (Me, F, HOOCCH₂CH₂CH₂, CF₃), (Me, F, HOOCCH₂CH₂CH₂, Br), (Me, F, HOOCCH₂CH₂CH₂, Me), (Me, F, HOOCCH₂CH₂CH₂CH₂, H), (Me, F, HOOCCH₂CH₂CH₂CH₂, Cl), (Me, F, HOOCCH₂CH₂CH₂CH₂, F), (Me, F, HOOCCH₂CH₂CH₂CH₂, CF₃), (Me, F, HOOCCH₂CH₂CH₂CH₂, Br), (Me, F, HOOCCH₂CH₂CH₂CH₂, Me), (Me, F, (Me)₂NCOCH₂CH₂CH₂, H), (Me, F, (Me)₂NCOCH₂CH₂CH₂, Cl), (Me, F, (Me)₂NCOCH₂CH₂CH₂, F), (Me, F, (Me)₂NCOCH₂CH₂CH₂, CF₃), (Me, F, (Me)₂NCOCH₂CH₂CH₂, Br), (Me, F, (Me)₂NCOCH₂CH₂CH₂, Me), (Me, F, (Me)₂NCOCH₂CH₂CH₂CH₂, H), (Me, F, (Me)₂NCOCH₂CH₂CH₂CH₂, Cl), (Me, F, (Me)₂NCOCH₂CH₂CH₂CH₂, F), (Me, F, (Me)₂NCOCH₂CH₂CH₂CH₂, CF₃), (Me, F, (Me)₂NCOCH₂CH₂CH₂CH₂, Br), (Me, F, (Me)₂NCOCH₂CH₂CH₂CH₂, Me), (Me, F, MeOCH₂, H), (Me, F, MeOCH₂, Cl), (Me, F, MeOCH₂, F), (Me, F, MeOCH₂, CF₃), (Me, F, MeOCH₂, Br), (Me, F, MeOCH₂, Me), (Me, F, EtOCH₂, H), (Me, F, EtOCH₂, Cl), (Me, F, EtOCH₂, F), (Me, F, EtOCH₂, CF₃), (Me, F, EtOCH₂, Br), (Me, F, EtOCH₂, Me), (Me, F, EtOCH₂CH₂, H), (Me, F, EtOCH₂CH₂, Cl), (Me, F, EtOCH₂CH₂, F), (Me, F, EtOCH₂CH₂, CF₃), (Me, F, EtOCH₂CH₂, Br), (Me, F, EtOCH₂CH₂, Me), (Me, F, MeOCH₂CH₂OCH₂CH₂, H), (Me, F, MeOCH₂CH₂OCH₂CH₂, Cl), (Me, F, MeOCH₂CH₂OCH₂CH₂, F), (Me, F, MeOCH₂CH₂OCH₂CH₂, CF₃), (Me, F, MeOCH₂CH₂OCH₂CH₂, Br), (Me, F, MeOCH₂CH₂OCH₂CH₂, Me), (Me, F, MeOCH₂CH₂, H), (Me, F, MeOCH₂CH₂, Cl), (Me, F, MeOCH₂CH₂, F), (Me, F, MeOCH₂CH₂, CF₃), (Me, F, MeOCH₂CH₂, Br), (Me, F, MeOCH₂CH₂, Me), (Me, F, HOCH₂, H), (Me, F, HOCH₂, Cl), (Me, F, HOCH₂, F), (Me, F, HOCH₂, CF₃), (Me, F, HOCH₂, Br), (Me, F, HOCH₂, Me), (Me, F, HOCH₂CH₂, H), (Me, F, HOCH₂CH₂, Cl), (Me, F, HOCH₂CH₂, F), (Me, F, HOCH₂CH₂, CF₃), (Me, F, HOCH₂CH₂, Br), (Me, F, HOCH₂CH₂, Me), (Me, F, HOCH₂CH₂CH₂, H), (Me, F, HOCH₂CH₂CH₂, Cl), (Me, F, HOCH₂CH₂CH₂, F), (Me, F, HOCH₂CH₂CH₂, CF₃), (Me, F, HOCH₂CH₂CH₂, Br), (Me, F, HOCH₂CH₂CH₂, Me), (Me, F, HOCH₂CH₂CH₂CH₂, H), (Me, F, HOCH₂CH₂CH₂CH₂, Cl), (Me, F, HOCH₂CH₂CH₂CH₂, F), (Me, F, HOCH₂CH₂CH₂CH₂, CF₃), (Me, F, HOCH₂CH₂CH₂CH₂, Br), (Me, F, HOCH₂CH₂CH₂CH₂, Me), (Me, F, HOCH₂CH₂CH₂CH₂CH₂, H), (Me, F, HOCH₂CH₂CH₂CH₂CH₂, Cl), (Me, F, HOCH₂CH₂CH₂CH₂CH₂, F), (Me, F, HOCH₂CH₂CH₂CH₂CH₂, CF₃), (Me, F, HOCH₂CH₂CH₂CH₂CH₂, Br), (Me, F, HOCH₂CH₂CH₂CH₂CH₂, Me), (Me, F, HOCH₂CH₂OCH₂CH₂, H), (Me, F, HOCH₂CH₂OCH₂CH₂, Cl), (Me, F, HOCH₂CH₂OCH₂CH₂, F), (Me, F, HOCH₂CH₂OCH₂CH₂, CF₃), (Me, F, HOCH₂CH₂OCH₂CH₂, Br), (Me, F, HOCH₂CH₂OCH₂CH₂, Me), (Me, F, (Me)₂N, H), (Me, F, (Me)₂N, Cl), (Me, F, (Me)₂N, F), (Me, F, (Me)₂N, CF₃), (Me, F, (Me)₂N, Br), (Me, F, (Me)₂N, Me), (Me, F, piperidin-4-yl-methyl, H), (Me, F, piperidin-4-yl-methyl, Cl), (Me, F, piperidin-4-yl-methyl, F), (Me, F, piperidin-4-yl-methyl, CF₃), (Me, F, piperidin-4-yl-methyl, Br), (Me, F, piperidin-4-yl-methyl, Me), (Me, F, cyclohexylmethyl, H), (Me, F, cyclohexylmethyl, Cl), (Me, F, cyclohexylmethyl, F), (Me, F, cyclohexylmethyl, CF₃), (Me, F, cyclohexylmethyl, Br), (Me, F, cyclohexylmethyl, Me), (Me, Cl, H, H), (Me, Cl, H, Cl), (Me, Cl, H, F), (Me, Cl, H, CF₃), (Me, Cl, H, Br), (Me, Cl, H, Me), (Me, Cl, F, H), (Me, Cl, F, Cl), (Me, Cl, F, F), (Me, Cl, F, CF$_3$), (Me, Cl, F, Br), (Me, Cl, F, Me), (Me, Cl, Cl, H), (Me, Cl, Cl, Cl), (Me, Cl, Cl, F), (Me, Cl, Cl, CF$_3$), (Me, Cl, Cl, Br), (Me, Cl, Cl, Me), (Me, Cl, Me, H), (Me, Cl, Me, Cl), (Me, Cl, Me, F), (Me, Cl, Me, CF$_3$), (Me, Cl, Me, Br), (Me, Cl, Me, Me), (Me, Cl, Et, H), (Me, Cl, Et, Cl), (Me, Cl, Et, F), (Me, Cl, Et, CF$_3$), (Me, Cl, Et, Br), (Me, Cl, Et, Me), (Me, Cl, n-Pr, H), (Me, Cl, n-Pr, Cl), (Me, Cl, n-Pr, F), (Me, Cl, n-Pr, CF$_3$), (Me, Cl, n-Pr, Br), (Me, Cl, n-Pr, Me), (Me, Cl, c-Pr, H), (Me, Cl, c-Pr, Cl), (Me, Cl, c-Pr, F), (Me, Cl, c-Pr, CF$_3$), (Me, Cl, c-Pr, Br), (Me, Cl, c-Pr, Me), (Me, Cl, i-Pr, H), (Me, Cl, i-Pr, Cl), (Me, Cl, i-Pr, F), (Me, Cl, i-Pr, CF$_3$), (Me, Cl, i-Pr, Br), (Me, Cl, i-Pr, Me), (Me, Cl, n-Bu, H), (Me, Cl, n-Bu, Cl), (Me, Cl, n-Bu, F), (Me, Cl, n-Bu, CF$_3$), (Me, Cl, n-Bu, Br), (Me, Cl, n-Bu, Me), (Me, Cl, i-Bu, H), (Me, Cl, i-Bu, Cl), (Me, Cl, i-Bu, F), (Me, Cl, i-Bu, CF$_3$), (Me, Cl, i-Bu, Br), (Me, Cl, i-Bu, Me), (Me, Cl, sec-Bu, H), (Me, Cl, sec-Bu, Cl), (Me, Cl, sec-Bu, F), (Me, Cl, sec-Bu, CF$_3$), (Me, Cl, sec-Bu, Br), (Me, Cl, sec-Bu, Me), (Me, Cl, n-Pen, H), (Me, Cl, n-Pen, Cl), (Me, Cl, n-Pen, F), (Me, Cl, n-Pen, CF$_3$), (Me, Cl, n-Pen, Br), (Me, Cl, n-Pen, Me), (Me, Cl, c-Pen, H), (Me, Cl, c-Pen, Cl), (Me, Cl, c-Pen, F), (Me, Cl, c-Pen, CF$_3$), (Me, Cl, c-Pen, Br), (Me, Cl, c-Pen, Me), (Me, Cl, n-Hex, H), (Me, Cl, n-Hex, Cl), (Me, Cl, n-Hex, F), (Me, Cl, n-Hex, CF$_3$), (Me, Cl, n-Hex, Br), (Me, Cl, n-Hex, Me), (Me, Cl, c-Hex, H), (Me, Cl, c-Hex, Cl), (Me, Cl, c-Hex, F), (Me, Cl, c-Hex, CF$_3$), (Me, Cl, c-Hex, Br), (Me, Cl, c-Hex, Me), (Me, Cl, OH, H), (Me, Cl, OH, Cl), (Me, Cl, OH, F), (Me, Cl, OH, CF$_3$), (Me, Cl, OH, Br), (Me, Cl, OH, Me), (Me, Cl, MeO, H), (Me, Cl, MeO, Cl), (Me, Cl, MeO, F), (Me, Cl, MeO, CF$_3$), (Me, Cl, MeO, Br), (Me, Cl, MeO, Me), (Me, Cl, EtO, H), (Me, Cl, EtO, Cl), (Me, Cl, EtO, F), (Me, Cl, EtO, CF$_3$), (Me, Cl, EtO, Br), (Me, Cl, EtO, Me), (Me, Cl, n-PrO, H), (Me, Cl, n-PrO, Cl), (Me, Cl, n-PrO, F), (Me, Cl, n-PrO, CF$_3$), (Me, Cl, n-PrO, Br), (Me, Cl, n-PrO, Me), (Me, Cl, PhO, H), (Me, Cl, PhO, Cl), (Me, Cl, PhO, F), (Me, Cl, PhO, CF$_3$), (Me, Cl, PhO, Br), (Me, Cl, PhO, Me), (Me, Cl, BnO, H), (Me, Cl, BnO, Cl), (Me, Cl, BnO, F), (Me, Cl, BnO, CF$_3$), (Me, Cl, BnO, Br), (Me, Cl, BnO, Me), (Me, Cl, PhCH$_2$CH$_2$O, H), (Me, Cl, PhCH$_2$CH$_2$O, Cl), (Me, Cl, PhCH$_2$CH$_2$O, F), (Me, Cl, PhCH$_2$CH$_2$O, CF$_3$), (Me, Cl, PhCH$_2$CH$_2$O, Br), (Me, Cl, PhCH$_2$CH$_2$O, Me), (Me, Cl, CF$_3$, H), (Me, Cl, CF$_3$, Cl), (Me, Cl, CF$_3$, F), (Me, Cl, CF$_3$, CF$_3$), (Me, Cl, CF$_3$, Br), (Me, Cl, CF$_3$, Me), (Me, Cl, CF$_3$O, H), (Me, Cl, CF$_3$O, Cl), (Me, Cl, CF$_3$O, F), (Me, Cl, CF$_3$O, CF$_3$), (Me, Cl, CF$_3$O, Br), (Me, Cl, CF$_3$O, Me), (Me, Cl, Ph, H), (Me, Cl, Ph, Cl), (Me, Cl, Ph, F), (Me, Cl, Ph, CF$_3$), (Me, Cl, Ph, Br), (Me, Cl, Ph, Me), (Me, Cl, 4-F-Ph, H), (Me, Cl, 4-F-Ph, Cl), (Me, Cl, 4-F-Ph, F), (Me, Cl, 4-F-Ph, CF$_3$), (Me, Cl, 4-F-Ph, Br), (Me, Cl, 4-F-Ph, Me), (Me, Cl, 4-CF$_3$-Ph, H), (Me, Cl, 4-CF$_3$-Ph, Cl), (Me, Cl, 4-CF$_3$-Ph, F), (Me, Cl, 4-CF$_3$-Ph, CF$_3$), (Me, Cl, 4-CF$_3$-Ph, Br), (Me, Cl, 4-CF$_3$-Ph, Me), (Me, Cl, 4-(Me)$_2$N-Ph, H), (Me, Cl, 4-(Me)$_2$N-Ph, Cl), (Me, Cl, 4-(Me)$_2$N-Ph, F), (Me, Cl, 4-(Me)$_2$N-Ph, CF$_3$), (Me, Cl, 4-(Me)$_2$N-Ph, Br), (Me, Cl, 4-(Me)$_2$N-Ph, Me), (Me, Cl, 4-OH-Ph, H), (Me, Cl, 4-OH-Ph, Cl), (Me, Cl, 4-OH-Ph, F), (Me, Cl, 4-OH-Ph, CF$_3$), (Me, Cl, 4-OH-Ph, Br), (Me, Cl, 4-OH-Ph, Me), (Me, Cl, 3,4-di-F-Ph, H), (Me, Cl, 3,4-di-F-Ph, Cl), (Me, Cl, 3,4-di-F-Ph, F), (Me, Cl, 3,4-di-F-Ph, CF$_3$), (Me, Cl, 3,4-di-F-Ph, Br), (Me, Cl, 3,4-di-F-Ph, Me), (Me, Cl, 4-COOH-Ph, H), (Me, Cl, 4-COOH-Ph, Cl), (Me, Cl, 4-COOH-Ph, F), (Me, Cl, 4-COOH-Ph, CF$_3$), (Me, Cl, 4-COOH-Ph, Br), (Me, Cl, 4-COOH-Ph, Me), (Me, Cl, Bn, H), (Me, Cl, Bn, Cl), (Me, Cl, Bn, F), (Me, Cl, Bn, CF$_3$), (Me, Cl, Bn, Br), (Me, Cl, Bn, Me), (Me, Cl, 4-F-Bn, H), (Me, Cl, 4-F-Bn, Cl), (Me, Cl, 4-F-Bn, F), (Me, Cl, 4-F-Bn, CF$_3$), (Me, Cl, 4-F-Bn, Br), (Me, Cl, 4-F-Bn, Me), (Me, Cl, 2-Py, H), (Me, Cl, 2-Py, Cl), (Me, Cl, 2-Py, F), (Me, Cl, 2-Py, CF$_3$), (Me, Cl, 2-Py, Br), (Me, Cl, 2-Py, Me), (Me, Cl, 3-Py, H), (Me, Cl, 3-Py, Cl), (Me, Cl, 3-Py, F), (Me, Cl, 3-Py, CF$_3$), (Me, Cl, 3-Py, Br), (Me, Cl, 3-Py, Me), (Me, Cl, 4-Py, H), (Me, Cl, 4-Py, Cl), (Me, Cl, 4-Py, F), (Me, Cl, 4-Py, CF$_3$), (Me, Cl, 4-Py, Br), (Me, Cl, 4-Py, Me), (Me, Cl, 2-Th, H), (Me, Cl, 2-Th, Cl), (Me, Cl, 2-Th, F), (Me, Cl, 2-Th, CF$_3$), (Me, Cl, 2-Th, Br), (Me, Cl, 2-Th, Me), (Me, Cl, 3-Th, H), (Me, Cl, 3-Th, Cl), (Me, Cl, 3-Th, F), (Me, Cl, 3-Th, CF$_3$), (Me, Cl, 3-Th, Br), (Me, Cl, 3-Th, Me), (Me, Ci, Pyrazol-2-yl, H), (Me, Cl, Pyrazol-2-yl, Cl), (Me, Cl, Pyrazol-2-yl, F), (Me, Cl, Pyrazol-2-yl, CF$_3$), (Me, Cl, Pyrazol-2-yl, Br), (Me, Cl, Pyrazol-2-yl, Me), (Me, Cl, Pyrazol-3-yl, H), (Me, Cl, Pyrazol-3-yl, Cl), (Me, Cl, Pyrazol-3-yl, F), (Me, Cl, Pyrazol-3-yl, CF$_3$), (Me, Cl, Pyrazol-3-yl, Br), (Me, Cl, Pyrazol-3-yl, Me), (Me, Cl, pyrimidin-2-yl, H), (Me, Cl, pyrimidin-2-yl, Cl), (Me, Cl, pyrimidin-2-yl, F), (Me, Cl, pyrimidin-2-yl, CF$_3$), (Me, Cl, pyrimidin-2-yl, Br), (Me, Cl, pyrimidin-2-yl, Me), (Me, Cl, pyrimidin-4-yl, H), (Me, Cl, pyrimidin-4-yl, Cl), (Me, Cl, pyrimidin-4-yl, F), (Me, Cl, pyrimidin-4-yl, CF$_3$), (Me, Cl, pyrimidin-4-yl, Br), (Me, Cl, pyrimidin-4-yl, Me), (Me, Cl, pyrimidin-5-yl, H), (Me, Cl, pyrimidin-5-yl, Cl), (Me, Cl, pyrimidin-5-yl, F), (Me, Cl, pyrimidin-5-yl, CF$_3$), (Me, Cl, pyrimidin-5-yl, Br), (Me, Cl, pyrimidin-5-yl, Me), (Me, Cl, HOOCCH$_2$CH$_2$CH$_2$, H), (Me, Cl, HOOCCH$_2$CH$_2$CH$_2$, Cl), (Me, Cl, HOOCCH$_2$CH$_2$CH$_2$, F), (Me, Cl, HOOCCH$_2$CH$_2$CH$_2$, CF$_3$), (Me, Cl, HOOCCH$_2$CH$_2$CH$_2$, Br), (Me, Cl, HOOCCH$_2$CH$_2$CH$_2$, Me), (Me, Cl, HOOCCH$_2$CH$_2$CH$_2$CH$_2$, H), (Me, Cl, HOOCCH$_2$CH$_2$CH$_2$CH$_2$, Cl), (Me, Cl, HOOCCH$_2$CH$_2$CH$_2$CH$_2$, F), (Me, Cl, HOOCCH$_2$CH$_2$CH$_2$CH$_2$, CF$_3$), (Me, Cl, HOOCCH$_2$CH$_2$CH$_2$CH$_2$, Br), (Me, Cl, HOOCCH$_2$CH$_2$CH$_2$CH$_2$, Me), (Me, Cl, (Me)$_2$NCOCH$_2$CH$_2$CH$_2$, H), (Me, Cl, (Me)$_2$NCOCH$_2$CH$_2$CH$_2$, Cl), (Me, Cl, (Me)$_2$NCOCH$_2$CH$_2$CH$_2$, F), (Me, Cl, (Me)$_2$NCOCH$_2$CH$_2$CH$_2$, CF$_3$), (Me, Cl, (Me)$_2$NCOCH$_2$CH$_2$CH$_2$, Br), (Me, Cl, (Me)$_2$NCOCH$_2$CH$_2$CH$_2$, Me),(Me, Cl, (Me)$_2$NCOCH$_2$CH$_2$CH$_2$CH$_2$, H), (Me, Cl, (Me)$_2$NCOCH$_2$CH$_2$CH$_2$CH$_2$, Cl), (Me, Cl, (Me)$_2$NCOCH$_2$CH$_2$CH$_2$CH$_2$, F), (Me, Cl, (Me)$_2$NCOCH$_2$CH$_2$CH$_2$CH$_2$, CF$_3$), (Me, Cl, (Me)$_2$NCOCH$_2$CH$_2$CH$_2$CH$_2$, Br), (Me, Cl, (Me)$_2$NCOCH$_2$CH$_2$CH$_2$CH$_2$, Me), (Me, Cl, MeOCH$_2$, H), (Me, Cl, MeOCH$_2$, Cl), (Me, Cl, MeOCH$_2$, F), (Me, Cl, MeOCH$_2$, CF$_3$), (Me, Cl, MeOCH$_2$, Br), (Me, Cl, MeOCH$_2$, Me), (Me, Cl, EtOCH$_2$, H), (Me, Cl, EtOCH$_2$, Cl), (Me, Cl, EtOCH$_2$, F), (Me, Cl, EtOCH$_2$, CF$_3$), (Me, Cl, EtOCH$_2$, Br), (Me, Cl, EtOCH$_2$, Me), (Me, Cl, EtOCH$_2$CH$_2$, H), (Me, Cl, EtOCH$_2$CH$_2$, Cl), (Me, Cl, EtOCH$_2$CH$_2$, F), (Me, Cl, EtOCH$_2$CH$_2$, CF$_3$), (Me, Cl, EtOCH$_2$CH$_2$, Br), (Me, Cl, EtOCH$_2$CH$_2$, Me), (Me, Cl, MeOCH$_2$CH$_2$OCH$_2$CH$_2$, H), (Me, Cl, MeOCH$_2$CH$_2$OCH$_2$CH$_2$, Cl), (Me, Cl, MeOCH$_2$CH$_2$OCH$_2$CH$_2$, F), (Me, Cl, MeOCH$_2$CH$_2$OCH$_2$CH$_2$, CF$_3$), (Me, Cl, MeOCH$_2$CH$_2$OCH$_2$CH$_2$, Br), (Me, Cl, MeOCH$_2$CH$_2$OCH$_2$CH$_2$, Me), (Me, Cl, MeOCH$_2$CH$_2$, H), (Me, Cl, MeOCH$_2$CH$_2$, Cl), (Me, Cl, MeOCH$_2$CH$_2$, F), (Me, Cl, MeOCH$_2$CH$_2$, CF$_3$), (Me, Cl, MeOCH$_2$CH$_2$, Br), (Me, Cl, MeOCH$_2$CH$_2$, Me), (Me, Cl, HOCH$_2$, H), (Me, Cl, HOCH$_2$, Cl), (Me, Cl, HOCH$_2$, F), (Me, Cl, HOCH$_2$, CF$_3$), (Me, Cl, HOCH$_2$, Br), (Me, Cl, HOCH$_2$, Me), (Me, Cl, HOCH$_2$CH$_2$, H), (Me, Cl, HOCH$_2$CH$_2$, Cl), (Me, Cl, HOCH$_2$CH$_2$, F), (Me, Cl, HOCH$_2$CH$_2$, CF$_3$), (Me, Cl, HOCH$_2$CH$_2$, Br), (Me, Cl, HOCH$_2$CH$_2$, Me), (Me, Cl, HOCH$_2$CH$_2$CH$_2$, H), (Me, Cl, HOCH$_2$CH$_2$CH$_2$, Cl), (Me, Cl, HOCH$_2$CH$_2$CH$_2$, F), (Me, Cl, HOCH$_2$CH$_2$CH$_2$, CF$_3$), (Me, Cl, HOCH$_2$CH$_2$CH$_2$, Br), (Me, Cl, HOCH$_2$CH$_2$CH$_2$, Me), (Me, Cl, HOCH$_2$CH$_2$CH$_2$CH$_2$, H), (Me, Cl, HOCH$_2$CH$_2$CH$_2$CH$_2$, Cl), (Me, Cl, HOCH$_2$CH$_2$CH$_2$CH$_2$, F), (Me, Cl, HOCH$_2$CH$_2$CH$_2$CH$_2$, CF$_3$), (Me, Cl, HOCH$_2$CH$_2$CH$_2$CH$_2$, Br), (Me, Cl, HOCH$_2$CH$_2$CH$_2$CH$_2$, Me), (Me, Cl, HOCH$_2$CH$_2$CH$_2$CH$_2$CH$_2$, H), (Me, Cl, HOCH$_2$CH$_2$CH$_2$CH$_2$CH$_2$, Cl), (Me, Cl, HOCH$_2$CH$_2$CH$_2$CH$_2$CH$_2$, F), (Me, Cl, HOCH$_2$CH$_2$CH$_2$CH$_2$CH$_2$, CF$_3$), (Me, Cl, HOCH$_2$CH$_2$CH$_2$CH$_2$CH$_2$, Br), (Me, Cl, HOCH$_2$CH$_2$CH$_2$CH$_2$CH$_2$, Me), (Me, Cl, HOCH$_2$CH$_2$OCH$_2$CH$_2$, H), (Me, Cl, HOCH$_2$CH$_2$OCH$_2$CH$_2$, Cl), (Me, Cl, HOCH$_2$CH$_2$OCH$_2$CH$_2$, F), (Me, Cl, HOCH$_2$CH$_2$OCH$_2$CH$_2$, CF$_3$), (Me, Cl, HOCH$_2$CH$_2$OCH$_2$CH$_2$, Br), (Me, Cl, HOCH$_2$CH$_2$OCH$_2$CH$_2$, Me), (Me, Cl, (Me)$_2$N, H), (Me, Cl, (Me)$_2$N, Cl), (Me, Cl, (Me)$_2$N, F), (Me, Cl, (Me)$_2$N, CF$_3$), (Me, Cl, (Me)$_2$N, Br), (Me, Cl, (Me)$_2$N, Me), (Me, Cl, piperidin-4-yl-methyl, H), (Me, Cl, piperidin-4-yl-methyl, Cl), (Me, Cl, piperidin-4-yl-methyl, F), (Me, Cl, piperidin-4-yl-methyl, CF$_3$), (Me, Cl, piperidin-4-yl-methyl, Br), (Me, Cl, piperidin-4-yl-methyl, Me), (Me, Cl, cyclohexylmethyl, H), (Me, Cl, cyclohexylmethyl, Cl), (Me, Cl, cyclohexylmethyl, F). (Me, Cl, cyclohexylmethyl, CF$_3$), (Me, Cl, cyclohexylmethyl, Br), (Me, Cl, cyclohexylmethyl, Me)

Test Examples

Test Example 1

Isolation and Purification of Thrombopoietin (TPO)

Human TPO was purchased from R&D Systems.

Test Example 2

The Thrombopoietic Activity

The TPO dependent BaF/hTPOR cell line which was established by introducing human TPO receptor into BaF-B03 cells according to Collins et al (J. Cell. Physiol., 137:293–298 (1988)) was used to test the thrombopoietic activity of the present compound. The DNA sequences and encoded peptide sequences for human TPO receptor have been described by Vigon et al (Proc. Natl. Acad. Sci. USA, 89:5640–5644 (1992)). TPO dose not have any ability to support proliferation of interlukin-3 dependent parental cell line BaF-B03. BAF/hTPOR cells were maintained in RPMI medium and WEHI-3B conditioned medium as a source of murine interleukin-3 (IL-3). These cells were washed and resuspended in RPMI medium without a source of murine IL-3 and seeded into each well of 96-well microtiter plates at a density of 5×10$^4$ cells per well in the absence or presence of various concentration of hTPO or the present compound. After incubation at 37° C. for 20 hours in the 5% CO$_2$ incubator, 10% WST-1 reagent (Takara Biomedicals, Japan) was added to each wells and the cells were further incubated for 4 hours. The absorbance at 450 nm was measured. Table 14 exemplifies the ED$_{50}$ for tested compounds of the present invention, wherein the ED$_{50}$ is the half concentration of the concentration showing the maximum thrombopoietic activity.

TABLE 14

| Compound No. | ED$_{50}$ (μM) |
|---|---|
| A-1 | 0.040 |
| A-2 | 0.376 |
| A-3 | 0.965 |
| A-4 | 0.148 |
| A-5 | 0.165 |
| A-6 | 0.210 |
| A-7 | 0.250 |
| A-8 | 2.284 |
| A-9 | 0.306 |
| A-10 | 0.141 |
| A-11 | 0.552 |
| A-12 | 0.214 |
| A-13 | 0.270 |
| A-14 | 0.230 |
| A-15 | 0.240 |
| A-16 | 0.230 |
| A-17 | 0.023 |
| A-18 | 0.043 |
| A-20 | 1.580 |
| A-21 | 0.208 |
| A-22 | 0.190 |
| B-1 | 0.069 |
| B-2 | 0.214 |
| B-3 | 0.219 |
| B-4 | 0.110 |
| B-5 | 0.056 |
| B-6 | 0.066 |
| B-7 | 0.280 |
| B-8 | 0.120 |
| B-9 | 0.0281 |
| B-10 | 0.048 |
| B-11 | 0.066 |
| B-12 | 0.074 |
| B-13 | 0.342 |
| B-14 | 0.042 |
| B-15 | 0.059 |
| B-16 | 0.098 |
| B-17 | 0.146 |
| B-18 | 0.072 |
| B-19 | 0.048 |
| B-20 | 0.068 |
| B-21 | 0.060 |
| B-22 | 0.064 |
| B-23 | 0.045 |
| B-24 | 0.053 |
| B-25 | 0.038 |
| B-26 | 0.025 |
| B-27 | 0.024 |
| B-28 | 0.023 |
| B-29 | 0.049 |
| B-30 | 0.142 |
| B-31 | 0.104 |
| B-32 | 0.096 |
| C-1 | 0.595 |
| C-2 | 0.071 |
| C-3 | 0.995 |
| C-4 | 0.567 |
| C-5 | 0.880 |
| C-6 | 1.71 |
| C-7 | 5.67 |
| C-8 | 16.6 |
| D-1 | 0.021 |
| D-2 | 0.019 |
| D-3 | 0.37 |
| D-4 | 0.25 |
| D-5 | 0.21 |
| D-6 | 2.54 |
| D-7 | 0.045 |
| D-8 | 1.93 |
| D-9 | 0.054 |
| E-1 | 16.52 |
| E-2 | 0.960 |
| E-3 | 0.120 |

FORMULATION EXAMPLE

Formulation Example 1

Granules are prepared using the following ingredients.

| Ingredients | The compound represented by the formula (I) | 10 mg |
|---|---|---|
| | Lactose | 700 mg |
| | Corn starch | 274 mg |
| | HPC-L | 16 mg |
| | | 1000 mg |

The compound represented by the formula (I) and lactose are made pass through a 60 mesh sieve. Corn starch is made pass through a 120 mesh sieve. They are mixed by a twin shell blender. An aqueous solution of HPC-L (low mucosity hydroxypropylcellulose) is added to the mixture and the resulting mixture is kneaded, granulated (by the extrusion with pore size 0.5 to 1 mm mesh), and dried. The dried granules thus obtained are sieved by a swing sieve (12/60 mesh) to yield the granules.

Formulation 2

Powders for filling capsules are prepared using the following ingredients.

| Ingredients | The compound represented by the formula (I) | 10 mg |
|---|---|---|
| | Lactose | 79 mg |
| | Corn starch | 10 mg |
| | Magnesium stearate | 1 mg |
| | | 100 mg |

The compound represented by the formula (I) and lactose are made pass through a 60 mesh sieve. Corn starch is made pass through a 120 mesh sieve. These ingredients and magnesium stearate are mixed by a twin shell blender. 100 mg of the 10-fold trituration is filled into a No. 5 hard gelatin capsule.

Formulation 3

Granules for filling capsules are prepared using the following ingredients.

| Ingredients | The compound represented by the formula (I) | 15 mg |
|---|---|---|
| | Lactose | 90 mg |
| | Corn starch | 42 mg |
| | HPC-L | 3 mg |
| | | 150 mg |

The compound represented by the formula (I) and lactose are made pass through a 60 mesh sieve. Corn starch is made pass through a 120 mesh sieve. After mixing them, an aqueous solution of HPC-L is added to the mixture and the resulting mixture is kneaded, granulated, and dried. After the dried granules are lubricated, 150 mg of that are filled into a No. 4 hard gelatin capsule.

Formulation 4

Tablets are prepared using the following ingredients.

| Ingredients | The compound represented by the formula (I) | 10 mg |
|---|---|---|
| | Lactose | 90 mg |
| | Microcrystal cellulose | 30 mg |
| | CMC-Na | 15 mg |
| | Magnesium stearate | 5 mg |
| | | 150 mg |

The compound represented by the formula (I), lactose, microcrystal cellulose, and CMC-Na (carboxymethylcellulose sodium salt) are made pass through a 60 mesh sieve and then mixed. The resulting mixture is mixed with magnesium stearate to obtain the mixed powder for the tablet formulation. The mixed powder is compressed to yield tablets of 150 mg.

Formulation 5

Intravenous formulations are prepared using the following ingredients.

Ingredients The compound represented by the formula (I) 100 mg

Saturated fattyacid glyceride 1000 ml

Usually a solution of ingredients above described is administered intravenously to a patient by the speed of 1 ml/min.

INDUSTRIAL APPLICABILITY

The compounds of the present invention have thrombopoietin receptor agonism and are useful as the treating or preventing agent for hemopathy accompanied with unusual count of platelet, for example, thrombocytopenia and the like.

The invention claimed is:

1. A pharmaceutical composition exhibiting thrombopoietin receptor agonism comprising at least one of a pharmaceutically acceptable excipient, binder, penetrant, disintegrator, lubricant, or carrier, and at least one compound according to formula (I), its prodrugs, pharmaceutically acceptable salts, or solvates:

$$X^1-Y^1-Z^1 \quad (I)$$

wherein $X_1$ is

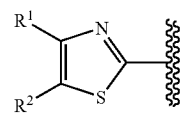

wherein $R^1$ and $R^2$ are each independently chosen from a hydrogen atom, optionally substituted lower alkyls, carboxy, lower alkyloxycarbonyls, halogen atoms, optionally substituted aminocarbonyls, optionally substituted heteroaryls, and optionally substituted aryls;

$Y^1$ is chosen from —NR$^A$CO—(CR$^C$R$^D$)$_{O\text{-}2}$, wherein $R^A$ is chosen from a hydrogen atom and lower alkyls; and $R^C$ and $R^D$ are each independently chosen from a hydrogen atom, halogen atoms, optionally substituted lower alkyls, optionally substituted lower alkyloxys, optionally substituted lower alkylthios, optionally substituted lower alkenyls, optionally substituted lower alkynyls, optionally substituted aryls, optionally substituted heteroaryls, optionally substituted cycloalkyls, optionally substituted aralkyls, optionally substituted heteroarylalkyls, optionally substituted non-aromatic heterocyclic groups, and optionally substituted amino groups; and $Z^1$ is

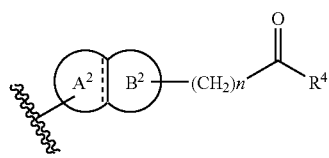

wherein $A^2$ ring and $B^2$ ring are each independently chosen from a cyclic group optionally substituted with one or more substituent(s) chosen from substituent A group, wherein the cyclic group is chosen from C5–C7 cycloalkanes, C5–C7 cycloalkenes, and benzene rings, and substituent A group consists of lower alkyls, halogen atoms, halo(lower)alkyls, hydroxy, lower alkyloxys, halo(lower)alkyloxys, methylene, and oxo;

$R^4$ is chosen from hydroxy, lower alkyloxys, and optionally substituted amino groups;

n is an integer of 0 to 4; and broken line (---) represents the presence or absence of a bond.

2. A pharmaceutical composition exhibiting thrombopoietin receptor agonism according to claim 1, wherein $Y^1$ is —NHCO— group.

3. A pharmaceutical composition exhibiting thrombopoietin receptor agonism according to claim 1, wherein the composition comprises the at least one compound of formula (I), its prodrugs, pharmaceutically acceptable salts or solvates thereof in an amount effective to be a platelet production modifier.

4. A pharmaceutical composition according to claim 1, wherein $X^1$ is chosen from:

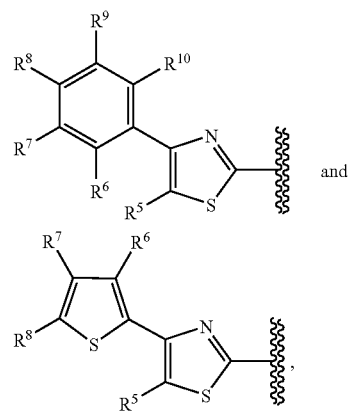

wherein $R^5$ is chosen from a hydrogen atom, optionally substituted lower alkyls, carboxy, lower alkyloxycarbonyls, halogen atoms, and optionally substituted aminocarbonyls;

$R^6$, $R^7$, $R^8$, $R^9$, and $R^{10}$ are each independently chosen from a hydrogen atom, alkyls optionally substituted with one or more substituent(s) chosen from substituent group B, cycloalkyls, alkyloxys optionally substituted with one or more substituent(s) chosen from substituent group B, alkylthios, halogen atoms, phenyl optionally substituted with one or more substituent(s) chosen from substituent group C, heteroaryls optionally substituted with one or more substituent(s) chosen from substituent group C, and non-aromatic heterocyclic groups optionally substituted with one or more substituent(s) chosen from substituent group C, substituent group B consists of cycloalkyls, hydroxy, alkyloxys, halogen atoms, carboxy, lower alkyloxycarbonyls, aryloxycarbonyls, optionally substituted amino groups, phenyl optionally substituted with one or more substituent(s) chosen from substituent group C, non-aromatic heterocyclic groups, and heteroaryls, and substituent group C consisits of hydroxy, alkyls, halogen atoms, halo(lower)alkyls, carboxy, lower alkyloxycarbonyls, alkyloxys, optionally substituted amino groups, non-aromatic heterocyclic groups, and heteroaryls; alternatively, $R^5$ and $R^6$ taken together may form —$CH_2$—, —$CH_2CH_2$—, —$CH_2CH_2CH_2$—, —$OCH_2$—, or —$SCH_2$—; and alternatively, $R^7$ and $R^8$ taken together may form —$(CH_2)_3$— or —$(CH_2)_4$—.

5. A pharmaceutical composition according to claim 1, wherein the $A^2$ ring and the $B^2$-ring of $Z^1$ are each independently chosen from benzene, cyclopentane, cyclohexane, cyclopentene, and cyclohexene.

6. A pharmaceutical composition comprising at least one of a pharmaceutically acceptable excipient, binder, penetrant, disintegrator, lubricant, or carrier, and at least one compound according to formula (III), its prod rugs, pharmaceutically acceptable salts, or solvates:

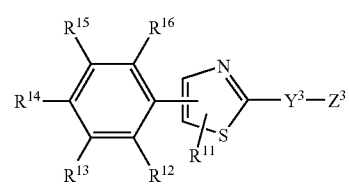

(III)

wherein $R^{11}$ is chosen from a hydrogen atom, optionally substituted lower alkyls, carboxy, lower alkyloxycarbonyls, halogen atoms, and optionally substituted aminocarbonyl;

$R^{12}$, $R^{13}$, $R^{14}$, $R^{15}$, and $R^{16}$ are each independently chosen from a hydrogen atom, alkyls optionally substituted with one or more substituent(s) chosen from substituent group B, cycloalkyls, alkyloxys optionally substituted with one or more substituent(s) chosen from substituent group B, alkylthios, halogen atoms, phenyl optionally substituted with one or more substituent(s) chosen from substituent group C, heteroaryls optionally substituted with one or more substituent(s) chosen from substituent group C, and non-aromatic heterocyclic groups optionally substituted with one or more substituent(s) chosen from substituent group C;

substituent group B consists of cycloalkyls, hydroxy, alkyloxys, halogen atoms, carboxy, lower alkyloxycarbonyls, aryloxycarbonyls, optionally substituted amino groups, phenyl optionally substituted with one or more substituent(s) chosen from substituent group C, non-aromatic heterocyclic groups, and heteroaryls, and substituent group C consists of hydroxy, alkyl, halogen atoms, halo(lower)alkyls, carboxy, lower alkyloxycarbonyls, alkyloxys, optionally substituted amino groups, non-aromatic heterocyclic groups, and heteroaryls;

alternatively, $R^{11}$ and $R^{12}$ taken together may form —$CH_2$—, —$CH_2CH_2$—, —$CH_2CH_2CH_2$—, —$OCH_2$—, or —$SCH_2$—; alternatively, $R^{13}$ and $R^{14}$ taken together may form —$(CH_2)_3$— or —$(CH_2)_4$—;

$Y^3$ is —NHCO—; and $Z^3$, which is optionally substituted with at least one substituent chosen from lower alkyls, halogen atoms, hydroxy, methylene, and oxo, is chosen from:

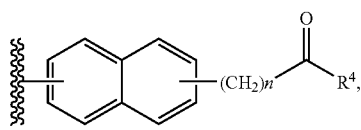

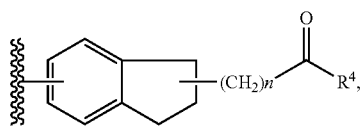

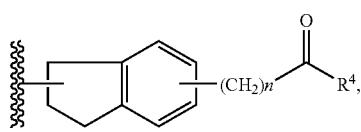

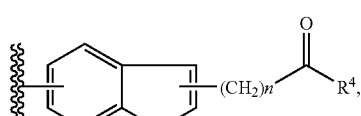

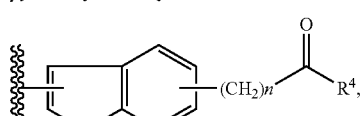

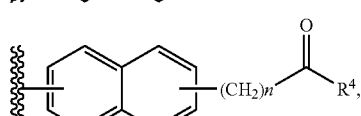

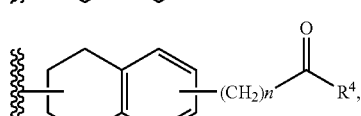

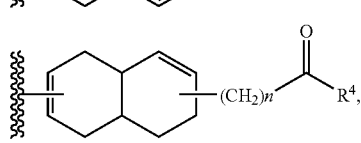

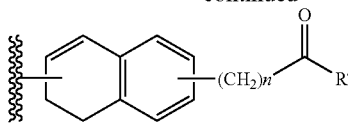

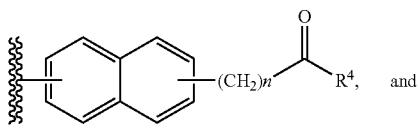

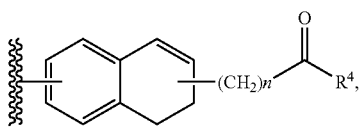

wherein $R^4$ is chosen from hydroxy, lower alkyloxys, and optionally substituted amino groups; and n is an integer of 0 to 4.

7. A compound according to formula (IV), its prodrugs, pharmaceutically acceptable salts, or solvates:

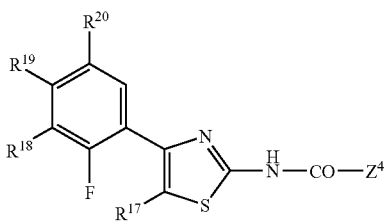

(IV)

wherein $R^{17}$ is chosen from a hydrogen atom, C1–C3 alkyls, trifluoromethyl, and halogen atoms;

$R^{18}$, $R^{19}$, and $R^{20}$ are each independently chosen from a hydrogen atom, alkyls optionally substituted with one or more substituent(s) chosen from substituent group B, cycloalkyls, alkyloxys optionally substituted with one or more substituent(s) chosen from substituent group B, alkylthios, halogen atoms, phenyl optionally substituted with one or more substituent(s) chosen from substituent group C, heteroaryls optionally substituted with one or more substituent(s) chosen from substituent group C, and non-aromatic heterocyclic groups optionally substituted with one or more substituent(s) chosen from substituent group C;

substituent group B consists of cycloalkyls, hydroxy, alkyloxys, halogen atoms, carboxy, lower alkyloxycarbonyls, aryloxycarbonyls, optionally substituted amino groups, phenyl optionally substituted with one or more substituent(s) chosen from substituent group C, non-aromatic heterocyclic groups, and heteroaryls, and substituent group C consists of hydroxy, alkyls, halogen atoms, halo(lower)alkyls, carboxy, lower alkyloxycarbonyls, alkyloxys, optionally substituted amino groups, non-aromatic heterocyclic groups, and heteroaryls; and $Z^4$ is a group represented by the formula:

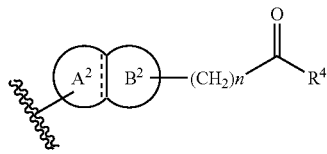

wherein
$A^2$ ring and $B^2$ ring are each independently chosen from a cyclic group optionally substituted with one or more substituent(s) chosen from substituent A group, wherein
the cyclic group is chosen from C5–C7 cycloalkanes. C5–C7 cycloalkenes, and benzene rings, and
substituent A group consists of lower alkyls, halogen atoms, halo(lower)alkyls, hydroxy, lower alkyloxys, halo(lower)alkyloxys, methylene, and oxo;
$R^4$ is chosen from hydroxy, lower alkyloxys, and optionally substituted amino groups:
n is an integer of 0 to 4; and
broken line (---) represents the presence or absence of a bond.

8. A compound according to claim 7, wherein $Z^4$, which is optionally substituted with at least one group chosen from lower alkyls, halogen atoms, hydroxy, methylene, and oxo, is chosen from:

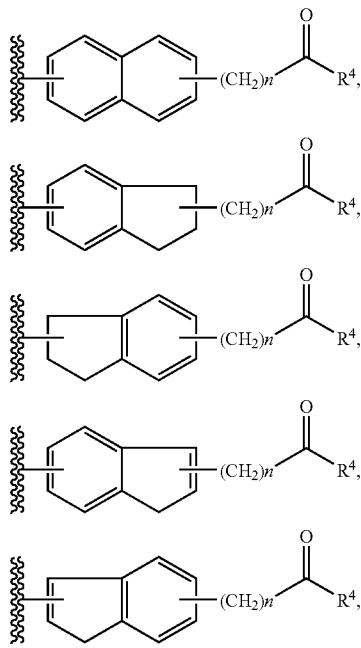

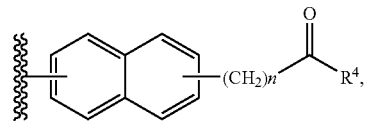

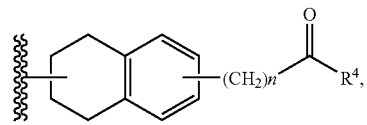

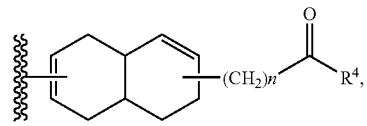

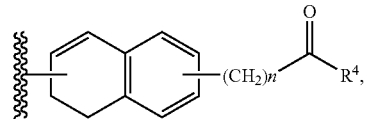

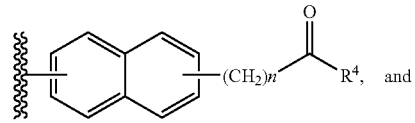 and

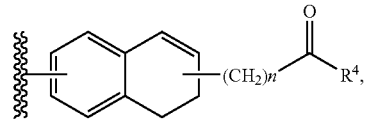

wherein
$R^4$ is chosen from hydroxy, lower alkyloxys, and optionally substituted amino groups;
and n is an integer of 0 to 4.

9. A pharmaceutical composition comprising as an active ingredient at least one compound according to any one of claims 7 and 8.

10. A pharmaceutical composition exhibiting thrombopoietin receptor agonism which comprises as an active ingredient a thrombopoietin effective amount of at least one compound pound according to any one of claims 7 and 8.

11. A platelet production modifier comprising as an active ingredient a platelet production modifying effective amount of at least one compound according to any one of claims 7 and 8.

12. A method for modifying platelet production of a mammal comprising administering to said mammal of a therapeutically effective amount of at least one compound according to any one of claims 7 and 8.

13. A method according to any one of claims 7 and 8, wherein the mammal is a human.

* * * * *

UNITED STATES PATENT AND TRADEMARK OFFICE
CERTIFICATE OF CORRECTION

PATENT NO. : 7,169,931 B2
APPLICATION NO. : 10/470002
DATED : January 30, 2007
INVENTOR(S) : Hiroshi Takemoto et al.

It is certified that error appears in the above-identified patent and that said Letters Patent is hereby corrected as shown below:

Col. 80, line 41, "prod rugs" should read --prodrugs--.

Col. 80, line 59, "R 15" should read --$R^{15}$--.

Signed and Sealed this

Eighth Day of May, 2007

JON W. DUDAS
*Director of the United States Patent and Trademark Office*